(12) United States Patent
Parton et al.

(10) Patent No.: US 9,029,392 B2
(45) Date of Patent: May 12, 2015

(54) QUINOLINE DERIVATIVES AS KINASE INHIBITORS

(75) Inventors: Andrew Harry Parton, Slough (GB); Mezher Hussein Ali, Slough (GB); Daniel Christopher Brookings, Slough (GB); Julien Alistair Brown, Slough (GB); Daniel James Ford, Slough (GB); Richard Jeremy Franklin, Slough (GB); Barry John Langham, Slough (GB); Judi Charlotte Neuss, Slough (GB); Joanna Rachel Quincey, Slough (GB); Jackalyn Hinkins, legal representative, Tubney (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 13/821,294

(22) PCT Filed: Sep. 2, 2011

(86) PCT No.: PCT/GB2011/051647
§ 371 (c)(1),
(2), (4) Date: Oct. 30, 2013

(87) PCT Pub. No.: WO2012/032334
PCT Pub. Date: Mar. 15, 2012

(65) Prior Publication Data
US 2013/0296338 A1 Nov. 7, 2013

(30) Foreign Application Priority Data

Sep. 8, 2010 (GB) .................................. 1014963.1
Jan. 21, 2011 (GB) .................................. 1101128.5

(51) Int. Cl.
*A61K 31/4709* (2006.01)
*C07D 215/12* (2006.01)
*C07D 471/04* (2006.01)
*A61K 31/519* (2006.01)

(52) U.S. Cl.
CPC ............ *C07D 471/04* (2013.01); *A61K 31/519* (2013.01)

(58) Field of Classification Search
CPC .......................... A61K 31/4709; C07D 215/12
USPC ........... 514/311; 544/279, 405; 546/167, 173, 546/268.1
See application file for complete search history.

(56) References Cited

FOREIGN PATENT DOCUMENTS

| CA | 2808959 | * | 3/2012 |
| WO | 2008/118454 A2 | | 10/2008 |
| WO | 2011/058108 A1 | | 5/2011 |

OTHER PUBLICATIONS

Vippagunta, et al. Advanced Drug Delivery Reviews, 48, 2001, 18.*
Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — McDonnell Boehnen Hulbert & Berghoff LLP

(57) ABSTRACT

Disclosed are a series of quinoline and quinoxaline derivatives comprising a fluorinated ethyl side-chain, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions. The compounds are of general formula (I):

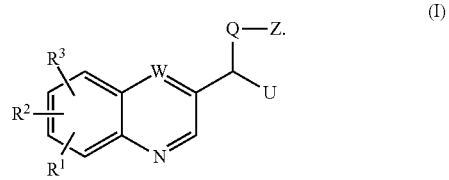

40 Claims, No Drawings

QUINOLINE DERIVATIVES AS KINASE INHIBITORS

CROSS-REFERENCE TO RELATED APPLICATIONS

This application is a US national phase of International Application No. PCT/GB2011/051647 filed on Sep. 2, 2011, which claims priority to United Kingdom Patent Application No. 1014963.1 filed on Sep. 8, 2010 and United Kingdom Patent Application No. 1101128.5 filed on Jan. 21, 2011, the disclosures of which are incorporated herein by reference in their entirety.

BACKGROUND OF THE INVENTION

1. Field of the Invention

The present invention relates to a class of quinoline and quinoxaline derivatives, and to their use in therapy. More particularly, the present invention provides quinoline and quinoxaline derivatives comprising a fluorinated ethyl sidechain. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

2. Description of the Related Art

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

BRIEF SUMMARY OF THE INVENTION

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe various series of quinoline and quinoxaline derivatives that are structurally related to each other and are stated to be useful to inhibit the biological activity of human PI3Kδ and to be of use in treating PI3K-mediated conditions or disorders.

WO 2009/081105, WO 2010/046639 and copending WO 2011/058108 (claiming priority from United Kingdom patent applications 0919829.2 and 1012102.8), published on 19 May 2011, describe separate classes of fused bicyclic heteroaryl derivatives as selective inhibitors of PI3K enzymes that are of benefit in the treatment of adverse inflammatory, autoimmune, cardiovascular, neurodegenerative, metabolic, ontological, nociceptive and ophthalmic conditions.

None of the prior art available to date, however, discloses or suggests the precise structural class of quinoline and quinoxaline derivatives comprising a fluorinated ethyl sidechain as provided by the present invention.

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The compounds of the invention possess notable advantages in terms of their high potency and selectivity, demonstrable efficacy, and valuable pharmacokinetic properties (including clearance and bioavailability).

DETAILED DESCRIPTION OF THE INVENTION

The present invention provides a compound of formula (I) or an N-oxide thereof, or a pharmaceutically acceptable salt or solvate thereof:

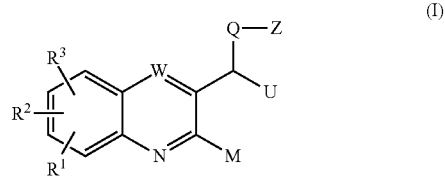

(I)

wherein

U represents —$CF_3$, —$CHF_2$ or —$CH_2F$;

Q represents oxygen, sulfur, N—$R^4$ or a covalent bond;

Z represents an optionally substituted bicyclic heteroaryl moiety consisting of two fused six-membered aromatic rings, the heteroaryl moiety Z containing at least one nitrogen atom and being linked to the remainder of the molecule through a carbon atom;

M represents aryl or heteroaryl, either of which groups may be optionally substituted by one or more substituents;

W represents C—$R^5$ or N;

$R^1$, $R^2$ and $R^3$ independently represent hydrogen, halogen, cyano, nitro, $C_{1-6}$ alkyl, trifluoromethyl, $C_{3-7}$ cycloalkyl($C_{1-6}$)alkyl, $C_{3-7}$ heterocycloalkyl($C_{1-6}$)alkyl, aryl($C_{1-6}$)-alkyl, heteroaryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^4$ represents hydrogen or $C_{1-6}$ alkyl; and $R^5$ represents hydrogen, halogen, $C_{1-6}$ alkyl or $C_{1-6}$ alkoxy.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydro-quinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=$O$) ↔ enol (CH=CHOH) tautomers or amide (NHC=O) ↔ hydroxyimine (N=COH) tautomers. Formula (I) and the formulae depicted hereinafter are intended to represent all individual tautomers and all possible mixtures thereof, unless stated or shown otherwise.

Advantageously, the absolute stereochemical configuration of the compounds of formula (I) above will be as depicted in formula (I-1):

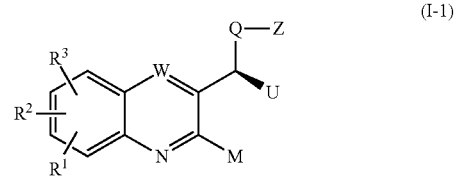

(I-1)

wherein U, Q, Z, M, W, $R^1$, $R^2$ and $R^3$ are as defined above.

In a selected embodiment, where U represents —$CF_3$, particular compounds of formula (I) as defined above include those wherein the carbon atom to which the -Q-Z and —$CF_3$ moieties are directly attached is in the (R) configuration.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a particular embodiment, U represents —$CF_3$. In another embodiment, U represents —$CHF_2$. In a further embodiment, U represents —$CH_2F$.

In one embodiment, W represents C—R⁵. In another embodiment, W represents N.

Specific sub-classes of compounds in accordance with the present invention are represented by the compounds of formula (IA) and (IB), especially (IA):

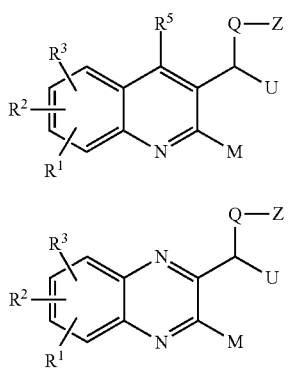

wherein U, Q, Z, M, R¹, R², R³ and R⁵ are as defined above.

Advantageously, the absolute stereochemical configuration of the compounds of formula (IA) above will be as depicted in formula (IA-1):

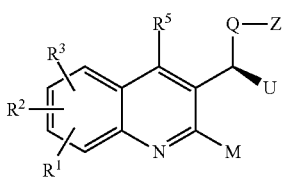

wherein U, Q, Z, M, R¹, R², R³ and R⁵ are as defined above.

Advantageously, the absolute stereochemical configuration of the compounds of formula (IB) above will be as depicted in formula (IB-1):

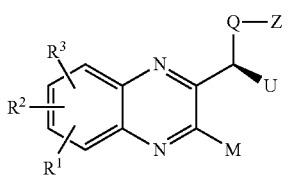

wherein U, Q, Z, M, R¹, R² and R³ are as defined above.

In a selected embodiment, where U represents —CF₃, particular compounds of formula (IA) and (IB) as defined above include those wherein the carbon atom to which the -Q-Z and —CF₃ moieties are directly attached is in the (R) configuration.

In one aspect of the invention, Q represents oxygen, sulfur or N—R⁴.

Suitable values of Q include oxygen and N—R⁴.

In one embodiment, Q represents oxygen. In another embodiment, Q represents sulfur. In a particular embodiment, Q represents N—R⁴. In a further embodiment, Q represents a covalent bond.

Generally, the bicyclic heteroaryl moiety Z contains one, two, three or four nitrogen atoms and no other heteroatoms. Typically, Z contains two, three or four nitrogen atoms. Suitably, Z contains two or three nitrogen atoms.

In one embodiment, Z contains one nitrogen atom. In another embodiment, Z contains two nitrogen atoms. In a particular embodiment, Z contains three nitrogen atoms. In a further embodiment, Z contains four nitrogen atoms.

Typical values for the heteroaryl moiety Z include quinolinyl, isoquinolinyl, cinnolinyl, quinazolinyl, quinoxalinyl, phthalazinyl, naphthyridinyl, pyrido-pyrimidinyl and pteridinyl, any of which groups may be optionally substituted by one or more substituents.

In one embodiment, Z represents optionally substituted pyrido-pyrimidinyl. In one aspect of that embodiment, Z represents optionally substituted pyridopyrimidin-4-yl. In another aspect of that embodiment, Z represents optionally substituted pyrido[3,2-d]-pyrimidinyl. In a more precise aspect of that embodiment, Z represents optionally substituted pyrido[3,2-d]pyrimidin-4-yl.

In a particular embodiment, the heteroaryl moiety Z is unsubstituted. In another embodiment, Z is substituted by one or more substituents. In one subset of that embodiment, Z is monosubstituted. In another subset of that embodiment, Z is disubstituted.

Typical examples of optional substituents on the heteroaryl moiety Z include one or more substituents independently selected from halogen, cyano, nitro, $C_{1-6}$ alkyl, trifluoromethyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, arylamino, $C_{1-6}$ alkoxyaryl($C_{1-6}$)alkylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional examples include $C_{2-6}$ alkoxycarbonylamino and ($C_{1-6}$)alkyl ($C_{3-6}$)heterocycloalkylcarbonyl.

Typical examples of specific substituents on Z include fluoro, chloro, bromo, cyano, nitro, methyl, isopropyl, trifluoromethyl, hydroxy, oxo, methoxy, difluoromethoxy, trifluoromethoxy, methylthio, methylsulfinyl, methylsulfonyl, amino, methylamino, tert-butylamino, dimethylamino, phenylamino, methoxybenzylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylamino sulfonyl.

One specific value of Z is pyrido[3,2-d]pyrimidin-4-yl.

Suitably, the moiety M represents a monocyclic aryl or heteroaryl group, either of which groups may be optionally substituted by one or more substituents.

In a particular embodiment, the aryl or heteroaryl moiety M is unsubstituted. In another embodiment, M is substituted by one or more substituents. In one subset of that embodiment, M is monosubstituted. In another subset of that embodiment, M is disubstituted. In a further subset of that embodiment, M is trisubstituted.

Typical values for the moiety M include phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents.

Selected values of M include phenyl, pyridinyl and pyrazinyl, any of which groups may be optionally substituted by one or more substituents.

Typical examples of optional substituents on the aryl or heteroaryl moiety M include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylamino carbonyl, di($C_{1-6}$)alkyl-aminocarbonyl, aminosulfonyl, $C_{1-6}$ alkylaminosulfonyl, di($C_{1-6}$)alkylaminosulfonyl, $C_{3-7}$ cycloalkyl, $C_{3-6}$ heterocycloalkyl, monocyclic aryl and monocyclic heteroaryl. Additional examples include $C_{2-6}$ alkoxycarbonylamino and ($C_{1-6}$)alkyl($C_{3-6}$)heterocycloalkyl.

Selected examples of optional substituents on M include one or more substituents independently selected from halogen, $C_{1-6}$ alkyl and $C_{1-6}$ alkoxy.

Typical examples of specific substituents on M include one or more substituents independently selected from fluoro, chloro, bromo, cyano, nitro, methyl, ethyl, isopropyl, trifluoromethyl, hydroxy, methoxy, isopropoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl, dimethylaminosulfonyl, cyclopropyl, azetidinyl, N-methylazetidinyl, tetrahydrofuranyl, pyrrolidinyl, N-methylpyrrolidinyl, imidazolidinyl, N-methylimidazolidinyl, tetrahydropyranyl, piperidinyl, N-methylpiperidinyl, piperazinyl, N-methylpiperazinyl, morpholinyl, thiomorpholinyl, phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl.

Selected examples of specific substituents on M include one or more substituents independently selected from chloro, methyl and methoxy.

Individual values of M include phenyl, pyridinyl, chloropyridinyl, methylpyridinyl, pyrazinyl and methoxypyrazinyl.

In a particular embodiment, M represents pyridinyl. In a particular aspect of that embodiment, M represents pyridin-3-yl.

In another embodiment, M represents methylpyridinyl. In a particular aspect of that embodiment, M represents 2-methylpyridin-3-yl.

Suitable values of $R^1$, $R^2$ and/or $R^3$ include hydrogen, halogen, $C_{1-6}$ alkyl, trifluoromethyl, aryl($C_{1-6}$)alkyl, $C_{1-6}$ alkoxy and $C_{1-6}$ alkylsulphonyl.

Typical values of $R^1$, $R^2$ and/or $R^3$ include hydrogen, halogen, $C_{1-6}$ alkyl, aryl($C_{1-6}$)alkyl and $C_{1-6}$ alkoxy.

Selected values of $R^1$, $R^2$ and/or $R^3$ include hydrogen, halogen, $C_{1-6}$ alkyl, trifluoromethyl and $C_{1-6}$ alkylsulphonyl.

Suitably, $R^1$, $R^2$ and $R^3$ independently represent hydrogen, fluoro, chloro, bromo, cyano, nitro, methyl, ethyl, trifluoromethyl, benzyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl or dimethylaminosulfonyl.

Suitably, $R^1$ represents hydrogen, halogen, $C_{1-6}$ alkyl, trifluoromethyl, aryl($C_{1-6}$)-alkyl, $C_{1-6}$ alkoxy or $C_{1-6}$ alkylsulphonyl.

Typically, $R^1$ represents hydrogen, halogen, $C_{1-6}$ alkyl, aryl($C_{1-6}$)alkyl or $C_{1-6}$ alkoxy.

Selected values of $R^1$ include hydrogen, halogen, $C_{1-6}$ alkyl, trifluoromethyl and $C_{1-6}$ alkylsulphonyl.

Illustrative values of $R^1$ include hydrogen, halogen and $C_{1-6}$ alkyl.

In one embodiment, $R^1$ represents hydrogen. In another embodiment, $R^1$ represents halogen, particularly fluoro or chloro. In one aspect of that embodiment, $R^1$ represents fluoro. In another aspect of that embodiment, $R^1$ represents chloro. In a further embodiment, $R^1$ represents $C_{1-6}$ alkyl, particularly methyl or ethyl. In one aspect of that embodiment, $R^1$ represents methyl. In another aspect of that embodiment, $R^1$ represents ethyl. In another embodiment, $R^1$ represents trifluoromethyl. In a still further embodiment, $R^1$ represents aryl($C_{1-6}$)alkyl, especially benzyl. In an additional embodiment, $R^1$ represents $C_{1-6}$ alkoxy, especially methoxy. In another embodiment, $R^1$ represents $C_{1-6}$ alkylsulphonyl. In one aspect of that embodiment, $R^1$ represents methyl-sulphonyl.

Suitably, $R^2$ represents hydrogen, halogen or $C_{1-6}$ alkyl.

Typically, $R^2$ represents hydrogen or halogen.

In one embodiment, $R^2$ represents hydrogen. In another embodiment, $R^2$ represents halogen, particularly fluoro or chloro. In one aspect of that embodiment, $R^2$ represents fluoro. In another aspect of that embodiment, $R^2$ represents chloro. In a further embodiment, $R^2$ represents $C_{1-6}$ alkyl. In one aspect of that embodiment, $R^2$ represents methyl.

Suitably, $R^3$ represents hydrogen or halogen.

Typically, $R^3$ represents hydrogen.

In one embodiment, $R^3$ represents hydrogen. In another embodiment, $R^3$ represents halogen. In one aspect of that embodiment, $R^3$ represents fluoro.

In a particular embodiment, $R^2$ and $R^3$ both represent hydrogen.

In one embodiment, $R^4$ represents hydrogen. In another embodiment, $R^4$ represents $C_{1-6}$ alkyl, especially methyl.

Suitable values of the group $R^4$ include hydrogen and methyl.

Typically, $R^5$ represents hydrogen or $C_{1-6}$ alkyl.

In one embodiment, $R^5$ represents hydrogen. In another embodiment, $R^5$ represents halogen, particularly fluoro or chloro. In one aspect of that embodiment, $R^5$ represents fluoro. In another aspect of that embodiment, $R^5$ represents chloro. In a further embodiment, $R^5$ represents $C_{1-6}$ alkyl, especially methyl. In an additional embodiment, $R^5$ represents $C_{1-6}$ alkoxy, especially methoxy.

Suitable values of the group $R^5$ include hydrogen, fluoro, chloro, bromo, methyl and methoxy. Suitably, $R^5$ represents hydrogen or methyl. Typically, $R^5$ represents hydrogen.

In a selected embodiment, the present invention provides an N-oxide derivative of a compound of formula (I) as defined above, or a pharmaceutically acceptable salt or solvate thereof.

One sub-class of compounds according to the invention is represented by the compounds of formula (IIA), and pharmaceutically acceptable salts and solvates thereof:

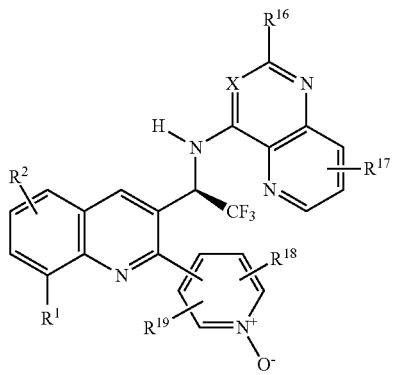

(IIA)

wherein $R^1$ and $R^2$ are as defined above;

X represents N or CH;

$R^{16}$ and $R^{17}$ independently represent hydrogen, halogen, cyano, $C_{1-6}$ alkyl, trifluoromethyl, amino, $C_{1-6}$ alkylamino or di($C_{1-6}$)alkylamino; and $R^{18}$ and $R^{19}$ independently represent hydrogen, halogen, cyano, $C_{1-6}$ alkyl, trifluoromethyl or aminocarbonyl.

In one embodiment, X is N. In another embodiment, X is CH.

Typical values of $R^{16}$ include hydrogen, fluoro, chloro, cyano, methyl, ethyl, isopropyl, trifluoromethyl, amino, methylamino, ethylamino, tert-butylamino and dimethylamino.

A particular value of $R^{16}$ is hydrogen.

Typical values of $R^{17}$ include hydrogen, fluoro, chloro, cyano, methyl, ethyl, isopropyl, trifluoromethyl, amino, methylamino, ethylamino, tert-butylamino and dimethylamino.

A particular value of $R^{17}$ is hydrogen.

Suitable values of $R^{18}$ include hydrogen and $C_{1-6}$ alkyl.

Typical values of $R^{18}$ include hydrogen, fluoro, chloro, cyano, methyl, trifluoromethyl and aminocarbonyl.

Selected values of $R^{18}$ include hydrogen and methyl.

In one embodiment, $R^{18}$ represents hydrogen. In another embodiment, $R^{18}$ represents halogen. In one aspect of that embodiment, $R^{18}$ represents fluoro. In another aspect of that embodiment, $R^{18}$ represents chloro. In a further embodiment, $R^{18}$ represents cyano. In another embodiment, $R^{18}$ represents $C_{1-6}$ alkyl. In one aspect of that embodiment, $R^{18}$ represents methyl. In a further embodiment, $R^{18}$ represents trifluoromethyl. In an additional embodiment, $R^{18}$ represents aminocarbonyl.

Typical values of $R^{19}$ include hydrogen, halogen, $C_{1-6}$ alkyl and trifluoromethyl.

A particular value of $R^{19}$ is hydrogen.

A particular subset of the compounds of formula (IIA) above is represented by the compounds of formula (IIB), and pharmaceutically acceptable salts and solvates thereof:

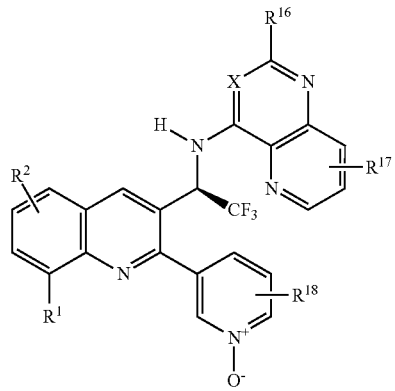

(IIB)

wherein $R^1$, $R^2$, X, $R^{16}$, $R^{17}$ and $R^{18}$ are as defined above.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein Q represents oxygen, sulfur or N—$R^4$ may be prepared by a process which comprises reacting a compound of formula $L^1$-Z with a compound of formula (III):

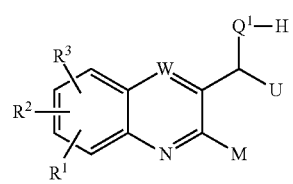

wherein $Q^1$ represents oxygen, sulfur or N—$R^4$, $L^1$ represents a suitable leaving group, and U, Z, M, W, $R^1$, $R^2$, $R^3$ and $R^4$ are as defined above.

The leaving group $L^1$ is typically a halogen atom, e.g. chloro. Alternatively, the leaving group $L^1$ may be 2,5-dioxopyrrolidin-1-yloxy.

The reaction is conveniently effected at an elevated temperature in a suitable solvent, e.g. a chlorinated solvent such as dichloromethane or chloroform, or a nitrile solvent such as acetonitrile. Optionally, the reaction may be performed in the presence of a reaction promoter such as 4-(dimethylamino)pyridine or p-toluenesulfonic acid.

Alternatively, the reaction may be performed at an elevated temperature in a suitable solvent, e.g. tetrahydrofuran, n-butanol, 1-methyl-2-pyrrolidinone (NMP) or 1,4-dioxane, typically in the presence of a suitable base, e.g. an organic base such as N,N-diisopropylethylamine.

The intermediates of formula (III) wherein $Q^1$ represents NH and U represents —$CF_3$ may be prepared by a three-step procedure which comprises: (i) treating a suitable compound of formula (IV):

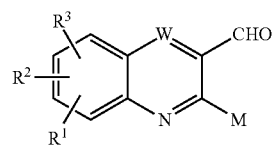

wherein M, W, $R^1$, $R^2$ and $R^3$ are as defined above; with 2-methyl-2-propanesulfinamide in the presence of titanium (IV) isopropoxide or potassium phosphate; (ii) reaction of the resulting compound with (trifluoromethyl)trimethylsilane in the presence of tetrabutylammonium difluorotriphenylsilicate or tetrabutylammonium acetate; and (iii) treatment of the resulting compound with a mineral acid, e.g. hydrochloric acid.

The intermediates of formula (IV) may be prepared by reacting a compound of formula M-$T^1$ with a compound of formula (V):

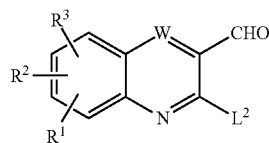

wherein $L^2$ represents a suitable leaving group, $T^1$ represents a boronic acid moiety —$B(OH)_2$ or a cyclic ester thereof formed with an organic diol, e.g. pinacol, 1,3-propane-diol or neopentyl glycol, or $T^1$ represents —$Sn(Alk^1)_3$ in which $Alk^1$ represents a $C_{1-6}$ alkyl group, typically n-butyl, or $T^1$ represents —$B(Alk^2)_2$ in which $Alk^2$ represents a $C_{1-6}$ alkyl group, typically ethyl, and M, W, $R^1$, $R^2$ and $R^3$ are as defined above; in the presence of a transition metal catalyst.

The leaving group $L^2$ is typically a halogen atom, e.g. chloro.

The transition metal catalyst is suitably tetrakis(triphenylphosphine)palladium(0), in which case the reaction is conveniently performed at an elevated temperature in a suitable solvent, e.g. an ethereal solvent such as ethylene glycol dimethyl ether or 1,4-dioxane, typically in the presence of sodium carbonate or sodium bicarbonate.

Alternatively, the intermediates of formula (IV) may be prepared by treating a compound of formula (VI):

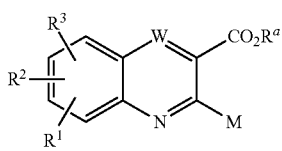
(VI)

wherein $R^a$ represents $C_{1-6}$ alkyl, e.g. ethyl, and M, W, $R^1$, $R^2$ and $R^3$ are as defined above; with a reducing agent, e.g. diisobutylaluminium hydride (DIBAL-H); followed by treatment of the compound thereby obtained with an oxidising agent such as manganese dioxide.

The intermediates of formula (VI) wherein W represents CH may be prepared by reacting a compound of formula (VII) with a compound of formula (VIII):

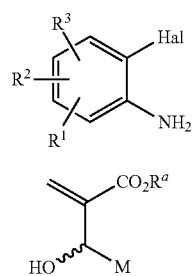
(VII)

(VIII)

wherein M, $R^1$, $R^2$, $R^3$ and $R^a$ are as defined above, and Hal represents halogen, e.g. bromo or iodo; in the presence of a transition metal catalyst, e.g. palladium(II) acetate; followed by treatment of the compound thereby obtained with an oxidising agent such as manganese dioxide.

The intermediates of formula (VIII) may be prepared by reacting a compound of formula M-CHO with a compound of formula (IX):

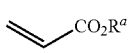
(IX)

wherein M and $R^a$ are as defined above.

The reaction is conveniently carried out in the presence of a base, ideally an organic base such as 1,4-diazabicyclo[2.2.2]octane (DABCO).

In another procedure, the intermediates of formula (IV) wherein W represents CH may be prepared by reacting a compound of formula M-CH=CH—CHO with a compound of formula (X):

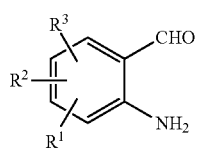
(X)

wherein M, $R^1$, $R^2$ and $R^3$ are as defined above; in the presence of a base, e.g. 2,5-dimethylpyrrolidine; followed by treatment of the compound thereby obtained with an oxidising agent such as manganese dioxide.

In a variant approach, the intermediates of formula (III) wherein $Q^1$ represents NH and U represents —$CF_3$ may be prepared by a four-step procedure which comprises: (i) treating a suitable compound of formula (V) as defined above with 2-methyl-2-propanesulfinamide in the presence of titanium (IV) isopropoxide or potassium phosphate; (ii) reacting the resulting compound with a compound of formula M-$T^1$, under conditions analogous to those described above for the reaction between M-$T^1$ and compound (V); (iii) reaction of the resulting compound with (trifluoromethyl)trimethylsilane in the presence of tetrabutylammonium difluorotriphenylsilicate or tetrabutylammonium acetate; and (iv) treatment of the resulting compound with a mineral acid, e.g. hydrochloric acid.

Where they are not commercially available, the starting materials of formula (V), (VII), (IX) and (IX) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of illustration, a compound of formula (I) wherein M represents pyridinyl may be converted into the corresponding compound wherein M is a pyridine-N-oxide moiety by treatment with a suitable oxidising agent, e.g. 3-chloroperoxybenzoic acid. Similarly, a compound of formula (I) wherein Z represents pyridopyrimidinyl may be converted into the corresponding compound wherein Z is a pyridopyrimidine-N-oxide moiety by treatment with a suitable oxidising agent, e.g. 3-chloroperoxybenzoic acid. A compound of formula (I) wherein $R^4$ represents hydrogen may be converted into the corresponding compound wherein $R^4$ represents $C_{1-6}$ alkyl, e.g. methyl, by treatment with a suitable alkylating agent, e.g. a methylating agent such as iodomethane, typically in the presence of a base such as sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the IC$_{50}$.

When tested in the above assay, the compounds of the accompanying Examples were all found to possess IC$_{50}$ values for inhibition of activity of human PI3Kα and/or PI3Kβ and/or PI3Kγ and/or PI3Kδ of 50 µM or better.

EXAMPLES

Abbreviations

DCM: dichloromethane
DMAP: 4-(dimethylamino)pyridine
EtOAc: ethyl acetate
MeOH: methanol
THF: tetrahydrofuran
DME: ethylene glycol dimethyl ether
DMSO: dimethylsulfoxide
MCPBA: 3-chloroperoxybenzoic acid
DABCO: 1,4-diazabicyclo[2.2.2]octane
DIBAL-H: diisobutylaluminium hydride
Rochelle salt: potassium sodium tartrate
DBU: 1,8-diazabicyclo[5.4.0]undec-7-ene
AcOH: acetic acid
DMF: N,N-dimethylformamide
r.t.: room temperature
RT: retention time
SiO$_2$: silica
h: hour
br: broad
M: mass
Pd(PPh$_3$)$_4$: tetrakis(triphenylphosphine)palladium(0)
PyBOP: (benzotriazol-1-yloxy)tripyrrolidinophosphonium hexafluorophosphate
brine: saturated aqueous sodium chloride solution
LCMS: Liquid Chromatography Mass Spectrometry
ES+: Electrospray Positive Ionisation Intermediate 1

8-Chloro-2-(pyridin-3-yl)quinoline-3-carbaldehyde

A mixture of 2,8-dichloroquinoline-3-carbaldehyde (5.0 g, 22.2 mmol), Na$_2$CO$_3$ (3.51 g, 33.2 mmol) and 3-pyridylboronic acid (2.72 g, 22.2 mmol) in DME (60 mL) and water (30 mL) was degassed by bubbling N$_2$ through it for 5 minutes. Pd(PPh$_3$)$_4$ (1.28 g, 1.11 mmol) was added and the mixture heated at 90° C. for 7 h. The mixture was allowed to cool to room temperature. The resultant precipitate was filtered off and washed with water (5×50 mL) and diethyl ether (5×50 mL) to give the title compound (5.4 g, 91%) as a tan solid. $\delta_H$ (DMSO-d$_6$) 10.15 (s, 1H), 9.15 (s, 1H), 8.94 (dd, J 2.3, 0.8 Hz, 1H), 8.77 (dd, J 4.9, 1.7 Hz, 1H), 8.31 (dd, J 8.3, 1.3 Hz, 1H), 8.20-8.19 (m, 1H), 8.18-8.16 (m, 1H), 7.75 (dd, J 7.9, 7.5 Hz, 1H), 7.62 (ddd, J 7.7, 4.9, 0.8 Hz, 1H). LCMS (ES+) 269 (M+H)$^+$, RT 1.82 minutes.

Alternative Procedure

To a solution of nicotinaldehyde (10.0 g, 93.4 mmol) in ethyl acrylate (20 mL, ~200 mmol) at room temperature was added DABCO (0.5 g, 4.5 mmol) and the mixture was stirred overnight. Excess ethyl acrylate was removed in vacuo to give a crude solid. This was washed with hexane to give 2-[(hydroxy)(pyridin-3-yl)methyl]acrylic acid ethyl ester (18.5 g, 95%) as an off white solid. $\delta_H$ (CDCl$_3$) 8.62 (d, J 1.7 Hz, 1H), 8.53 (dd, J 4.8, 1.3 Hz, 1H), 7.81 (d, J 7.9 Hz, 1H), 7.28 (s, 1H), 6.42 (s, 1H), 5.93 (s, 1H), 5.63 (s, 1H), 4.18 (m, 2H), 3.20 (br, 1H), 1.27 (t, J 7.1 Hz, 3H). LCMS (ES+) 208.2 (M+H)$^+$.

A degassed mixture of 2-[(hydroxy)(pyridin-3-yl)methyl] acrylic acid ethyl ester (8.2 g, 39.6 mmol), 6-chloro-2-iodoaniline (10.0 g, 39.5 mmol), triethylamine (9 mL, 122 mmol) and palladium(II) acetate (300 mg) in acetonitrile (80 mL) was heated at 70° C. overnight. The mixture was cooled to room temperature and partitioned between ethyl acetate (200 mL) and water (100 mL). The aqueous layer was separated and the organic layer was washed with brine (50 mL), filtered, dried (phase separator) and concentrated in vacuo to give a crude solid. This was washed with a minimum of ice-cold diethyl ether to yield 8-chloro-2-(pyridin-3-yl)-1,4-dihydroquinoline-3-carboxylic acid ethyl ester (10.8 g, 87%) as a white solid. $\delta_H$ (CDCl$_3$) 8.73 (m, 2H), 8.04 (m, 1H), 7.66 (dd, J 7.9, 5.5 Hz, 1H), 7.18 (m, 1H), 7.05 (m, 1H), 6.94 (m, 1H), 6.29 (s, 1H), 3.99 (m, 4H), 1.04 (t, J 7.1 Hz, 3H). LCMS (ES+) 315.0 (M+H)$^+$.

A suspension of 8-chloro-2-(pyridin-3-yl)-1,4-dihydroquinoline-3-carboxylic acid ethyl ester (10.7 g, 34 mmol) in chlorobenzene (60 mL) was treated with MnO$_2$ (10 g) and the mixture was heated to 60° C. for 3 h. The mixture was filtered through a celite plug and concentrated in vacuo. The residue was washed with diethyl ether to give 8-chloro-2-(pyridin-3-yl)quinoline-3-carboxylic acid ethyl ester (8.4 g, 79%) as a white solid. $\delta_H$ (CDCl$_3$) 8.96 (d, J 1.7 Hz, 1H), 8.83 (s, 1H), 8.75 (dd, J 5.0, 1.1 Hz, 1H), 8.27 (dt, J 7.9, 1.7 Hz, 1H), 8.00 (dd, J 7.5, 1.0 Hz, 1H), 7.92 (dd, J 8.2, 1.0 Hz, 1H), 7.60 (m, 2H), 4.32 (q, J 7.1 Hz, 2H), 1.24 (t, J 7.1 Hz, 3H). LCMS (ES+) 313.2 (M+H)$^+$.

To a suspension of 8-chloro-2-(pyridin-3-yl)quinoline-3-carboxylic acid ethyl ester (1.0 g, 3.2 mmol) in toluene at −78° C. was added a solution of DIBAL-H (10 mL, 1M in DCM) dropwise over 10 minutes. The mixture was stirred at this temperature for 2 h, then quenched by the addition of a saturated aqueous solution of Rochelle salt (5 mL). After warming to room temperature, extra Rochelle salt solution (5 mL) was added. The resulting solid was filtered, washed on the sinter with aqueous NaOH solution (2N) and water, and dried to give [8-chloro-2-(pyridin-3-yl)quinolin-3-yl]methanol (860 mg, quantitative) as a beige solid. $\delta_H$ (DMSO-d$_6$) 8.92 (d, J 1.7 Hz, 1H), 8.73 (dd, J 4.8, 1.6 Hz, 1H), 8.61 (s, 1H), 8.17 (dt, J 7.9, 1.9 Hz, 1H), 8.09 (dd, J 8.2, 1.1 Hz, 1H), 7.97 (dd, J 7.5, 1.2 Hz, 1H), 7.63 (m, 1H), 7.58 (ddd, J 7.8, 4.8, 0.6 Hz, 1H), 5.76 (s, 1H), 5.62 (t, J 5.2 Hz, 1H), 4.68 (d, J 4.9 Hz, 2H). LCMS (ES+) 271.0 (M+H)$^+$.

A mixture of [8-chloro-2-(pyridin-3-yl)quinolin-3-yl] methanol (0.6 g, 2.2 mmol) and MnO$_2$ (1.0 g) in chlorobenzene (30 mL) was heated at 70° C. overnight, filtered through a celite plug, concentrated in vacuo and washed with DCM to give the title compound (510 mg, 86%) as a white solid.

Intermediate 2

2-Methylpropane-2(S)-sulfinic acid N-[8-chloro-2-(pyridin-3-yl)quinolin-3-yl]meth-(E)-ylideneamide Titanium(IV) isopropoxide (3.17 g, 11.2 mmol) was added to a suspension of Intermediate 1 (1.5 g, 5.58 mmol) in anhydrous THF (30 mL). The mixture was stirred at r.t. for 10 minutes. (S)-2-Methyl-2-propanesulfinamide (0.74 g, 6.14 mmol) was added and the mixture stirred at 50° C. for 3 h. The reaction mixture was allowed to cool to r.t. then poured onto brine (50 mL) and filtered through Celite, washing with EtOAc. The filtrate was washed with brine, dried (Na$_2$SO$_4$) and concentrated in vacuo. Purification by column chromatography (SiO$_2$, 40-100% EtOAc in hexane) gave the title compound (1.88 g, 91%) as a tan solid. $\delta_H$ (DMSO-d$_6$) 9.20 (s, 1H), 8.85 (d, J 1.7 Hz, 1H), 8.77 (dd, J 4.9, 1.7 Hz, 1H), 8.61 (s, 1H), 8.29 (dd, J 8.3, 1.1 Hz, 1H), 8.13 (dd, J 7.5, 1.3 Hz, 1H), 8.12-8.08 (m, 1H), 7.72 (dd, J 8.1, 7.7 Hz, 1H), 7.64 (ddd, J 7.7, 4.9, 0.8 Hz, 1H), 1.21 (s, 9H). LCMS (ES+) 372 (M+H)$^+$, RT 2.37 minutes.

Intermediate 3

2-Methylpropane-2(S)-sulfinic acid {(R)-1-[8-chloro-2-(pyridin-3-yl)quinolin-3-yl]-2,2,2-trifluoroethyl}amide A mixture of Intermediate 2 (2.24 g, 6.03 mmol) and tetrabutylammonium difluorotriphenylsilicate (3.58 g, 6.64 mmol) in anhydrous THF (40 mL) was cooled to −40° C. (Trifluoromethyl)trimethylsilane (1.03 g, 7.24 mmol) was added and the mixture stirred at −40° C. for 1 h. Saturated aqueous ammonium chloride solution (5 mL) was added and the reaction mixture allowed to warm to r.t. The solvent was removed in vacuo and the residue was partitioned between EtOAc and water. The aqueous phase was extracted with further EtOAc and the combined organic fractions were washed with brine, then dried (Na$_2$SO$_4$) and evaporated in vacuo. The residue was purified by column chromatography (SiO$_2$, 40-100% EtOAc in hexane) to give the title compound (1.78 g, 67%) as a yellow gum. $\delta_H$ (DMSO-d$_6$) 9.02 (s, 1H), 8.80 (dd, J 4.9, 1.7 Hz, 1H), 8.78 (dd, J 2.3, 0.6 Hz, 1H), 8.15-8.09 (m, 2H), 8.04-7.99 (m, 1H), 7.77-7.71 (m, 1H), 7.67 (ddd, J 7.9, 4.9, 0.8 Hz, 1H), 6.65 (d, J 8.5 Hz, 1H), 5.12-5.00 (m, 1H), 1.15 (s, 9H). LCMS (ES+) 442 (M+H)$^+$, RT 2.39 minutes.

Intermediate 4

(R)-1-[8-Chloro-2-(pyridin-3-yl)quinolin-3-yl]-2,2,2-trifluoroethylamine

To a solution of Intermediate 3 (1.78 g, 4.04 mmol) in methanol (20 mL) was added a 4N solution of HCl in 1,4-dioxane (4 mL, 16.0 mmol). The mixture was stirred at r.t. for 1 h. The solvent was removed in vacuo and the residue triturated with diethyl ether (×2). The residue was then partitioned between DCM and saturated aqueous NaHCO$_3$ solution. The aqueous phase was extracted with further DCM and the combined organic fractions were washed with brine, then dried (Na$_2$SO$_4$) and evaporated in vacuo to give the title compound (1.28 g, 94%) as a yellow gum. $\delta_H$ (DMSO-d$_6$) 8.92 (s, 1H), 8.82 (d, J 2.1 Hz, 1H), 8.76 (dd, J 4.9, 1.5 Hz, 1H), 8.13-8.09 (m, 1H), 8.07-8.03 (m, 2H), 7.72-7.60 (m, 2H), 4.72-4.65 (m, 1H), 2.88-2.83 (m, 2H). LCMS (ES+) 338 (M+H)$^+$, RT 2.01 minutes.

Intermediate 5

8-Chloro-2-phenylquinoline-3-carbaldehyde

A mixture of 2,8-dichloroquinoline-3-carbaldehyde (2.0 g, 8.85 mmol), 2M aqueous Na$_2$CO$_3$ solution (8 mL), phenylboronic acid (1.5 g, 12.3 mmol) and tetrakis-(triphenylphosphine)palladium(0) (0.25 g, 0.216 mmol) in DME (30 mL) was degassed and the mixture heated at 110° C. for 4 h. The mixture was allowed to cool to room temperature, diluted with EtOAc and washed with brine. The organic layer was dried (MgSO$_4$) and the solvent was removed under reduced pressure. The resultant solid was triturated in ether, filtered, washed with small amount of ether, then light petroleum, and dried, to give the title compound (2.3 g, 97%) as an off-white solid. $\delta_H$ (CDCl$_3$) 10.25 (s, 1H), 8.86 (s, 1H), 7.95-8.02 (m, 2H), 7.78-7.14 (m, 2H), 7.54-7.62 (m, 4H). LCMS (ES+) 268 (M+H)$^+$, RT 1.98 minutes.

Intermediate 6

2-Methylpropane-2(S)-sulfinic acid N-(8-chloro-2-phenylquinolin-3-yl)meth-(E)-ylideneamide Titanium(IV) isopropoxide (5.1 mL, 17.24 mmol) was added to a stirred solution of Intermediate 5 (2.3 g, 8.6 mmol) in anhydrous THF (35 mL). The mixture was stirred at r.t. for 10 minutes, then (S)-2-methyl-2-propanesulfinamide (1.15 g, 9.5 mmol) was added and the mixture was stirred at 50° C. for 5.5 h. The heating was switched off and the reaction mixture was left stirring at room temperature overnight. Ice-water was added and the mixture was stirred for 10 minutes, diluted with EtOAc and filtered through Celite, washing with EtOAc. The filtrate was then washed with brine, dried (MgSO$_4$) and concentrated in vacuo. The crude solid was triturated with ether, then filtered, washed with ether and dried, to give the title compound (2.45 g, 77%) as a white solid. $\delta_H$ (DMSO-d$_6$) 9.14 (s, 1H), 8.61 (s, 1H), 8.27 (dd, J 4.9, 1.7 Hz, 1H), 8.10 (dd, J 8.3, 1.1 Hz, 1H), 7.59-7.69 (m, 6H), 1.24 (s, 9H). LCMS (ES+) 371 (M+H)$^+$, RT 2.1 minutes.

Intermediate 7

2-Methylpropane-2(S)-sulfinic acid [(R)-1-(8-chloro-2-phenylquinolin-3-yl)-2,2,2-trifluoroethyl]amide A mixture of Intermediate 6 (2.45 g, 6.61 mmol) and tetrabutylammonium difluorotriphenylsilicate (3.93 g, 7.28 mmol) in anhydrous THF (30 mL) was cooled to –70° C. (Trifluoromethyl)trimethylsilane (1.2 mL, 8.13 mmol) was added dropwise and the mixture was stirred for 2 h, allowing the temperature to rise slowly. LCMS showed some unreacted starting material, so the mixture was cooled again to –70° C. and more (trifluoromethyl)trimethylsilane (0.5 mL, 3.39 mmol) was added. The mixture was stirred for a further 2 h, allowing the temperature to rise slowly to 0° C. Saturated aqueous ammonium chloride solution (0.5 mL) was added and the reaction mixture was allowed to warm to room temperature. The reaction mixture was extracted twice using EtOAc, then dried (MgSO$_4$), and the solvent was evaporated in vacuo. The residue was purified by column chromatography (SiO$_2$, 10-60% EtOAc in hexane) to give the title compound (1.7 g, 58%) as pale yellow gum. $\delta_H$ (DMSO-d$_6$) 8.98 (s, 1H), 8.04-8.11 (m, 2H), 7.56-7.73 (m, 6H), 6.59 (d, J 8.63 Hz, 1H), 5.09-5.75 (m, 1H), 1.16 (s, 9H). LCMS (ES+) 441 (M+H)$^+$, RT 2.06 minutes.

Intermediate 8

(R)-1-(8-Chloro-2-phenylquinolin-3-yl)-2,2,2-trifluoroethylamine

To a solution of Intermediate 7 (0.75 g, 1.7 mmol) in DCM (2 mL) was added a 4N solution of HCl in 1,4-dioxane (10 mL). The mixture was stirred at r.t. for 20 minutes. The solvent was removed in vacuo and the residue was then partitioned between DCM and saturated aqueous NaHCO$_3$ solution. The aqueous phase was extracted with further DCM and the combined organic fractions were dried (MgSO$_4$) and evaporated in vacuo to give the title compound (0.55 g, 96%) as a yellow foam which was used without further purification. LCMS (ES+) 337 (M+H)$^+$, RT 1.99 minutes.

Intermediate 9

2-Methylpropane-2(S)-sulfinic acid N-(2,8-dichloro-quinolin-3-yl)meth-(E)-ylideneamide Potassium phosphate (16 g, 75.47 mmol) was dissolved in water (50 mL) and (S)-2-methyl-2-propanesulfinamide (10.5 g, 86.78 mmol) was added. The mixture was stirred for 10 minutes, then a solution of 2,8-dichloroquinoline-3-carbaldehyde (17.0 g, 75.22 mmol) in 2-propanol (50 mL) was added and the reaction mixture was stirred for two days. The solid was filtered, washed with water and dried in vacuo. The resulting solid was dissolved in DCM, washed with brine and dried (MgSO$_4$) and the solvent was removed under reduced pressure. The resulting solid was triturated in ether, filtered, washed with ether and dried to give the title compound (23.6 g, 95%) as a bright yellow solid. $\delta_H$ (CDCl$_3$) 9.12 (s, 1H), 8.83 (s, 1H), 7.90 (d, J 1.9 Hz, 1H), 7.87 (d, J 8.2 Hz, 1H), 7.55 (t, J 7.9 Hz, 1H), 1.33 (s, 9H). LCMS (ES+) 330 (M+H)$^+$, RT 1.94 minutes.

Intermediate 10

2-Methylpropane-2(S)-sulfinic acid N-[8-chloro-2-(4-methylpyridin-3-yl)quinolin-3-yl]-meth-(E)-ylideneamide A mixture of Intermediate 9 (5.0 g, 15.2 mmol), 4-methylpyridin-3-ylboronic acid (3.15 g, 21.43 mmol), tetrakis(triphenylphosphine)palladium(0) (0.17 g, 0.147 mmol) and 2M aqueous sodium bicarbonate solution (20 mL) in 1,4-dioxane (80 mL) was degassed and heated under reflux in a nitrogen atmosphere for 1 h. The reaction mixture was cooled to room temperature, then partitioned between EtOAc and brine, and the aqueous layer was extracted once more using EtOAc. The combined organic extracts were dried (MgSO$_4$) and the solvent was removed under reduced pressure. To a solution of the resulting material in 2-propanol (10 mL) was added a solution prepared by stirring potassium phosphate (2.8 g, 13.21 mmol) and (S)-2-methyl-2-propanesulfinamide (1.85 g, 15.3 mmol) in water (10 mL) for 15 minutes. The reaction mixture was left to stir over a weekend. Ice-water was added, and the resulting solid was collected by filtration, washed thoroughly with water and dried in air to give the title compound (5.84 g, 99%) as a brown solid. $\delta_H$ (CDCl$_3$) 8.91 (s, 1H), 8.58 (d, J 5.1 Hz, 1H), 8.52 (s, 1H), 8.50 (s, 1H), 7.96 (m, 2H), 7.58 (t, J 7.9 Hz, 1H), 7.29 (d, J 5.1 Hz, 1H), 2.29 (s, 3H), 1.24 (s, 9H). LCMS (ES+) 386 (M+H)$^+$, RT 1.88 minutes.

Intermediate 11

2-Methylpropane-2(S)-sulfinic acid {(R)-1-[8-chloro-2-(4-methylpyridin-3-yl)quinolin-3-yl]-2,2,2-trifluoroethyl}amide A solution of Intermediate 10 (5 g, 12.96 mmol) and tetrabutylammonium difluorotriphenylsilicate (7.7 g, 14.26 mmol) in anhydrous THF (100 mL) was cooled to –70° C. (Trifluoromethyl)trimethylsilane (2.3 mL, 15.58 mmol) was added dropwise and the mixture was stirred for 2 h, allowing the temperature to rise slowly. LCMS showed some unreacted starting material, so the mixture was cooled again to –70° C. and more (trifluoromethyl)trimethylsilane (2.3 mL, 15.58 mmol) was added. The mixture was stirred for a further 2.5 h, allowing the temperature to rise slowly to 0° C. Saturated aqueous ammonium chloride solution (0.5 mL) was added and the reaction mixture was allowed to warm to room temperature. The resulting material was extracted twice using EtOAc, then dried (MgSO$_4$), and the solvent was evaporated in vacuo. The residue was purified by column chromatography (SiO$_2$, 60% EtOAc in hexane). Fractions containing pure required isomer were bulked and the solvent was removed under reduced pressure to give the title compound (3.79 g, 32%) as a pale yellow gum. $\delta_H$ (DMSO-d$_6$ at 90° C.) 9.03 (s, 1H), 8.62 (d, J 5.0 Hz, 1H), 8.49 (br s, 1H), 8.06-8.11 (m, 2H), 7.73 (t, J 7.9 Hz, 1H), 7.49 (d, J 5.0 Hz, 1H), 6.29 (br s, 1H), 4.83 (br s, 1H), 2.18 (s, 3H), 1.18 (s, 9H). LCMS (ES+) 456 (M+H)$^+$, RT 1.93 minutes.

Intermediate 12

(R)-1-[8-Chloro-2-(4-methylpyridin-3-yl)quinolin-3-yl]-2,2,2-trifluoroethylamine To a solution of Intermediate 11 (1.8 g, 3.95 mmol) in 1,4-dioxane (2.5 mL) was added a 4N solution of HCl in 1,4-dioxane (15 mL). The mixture was stirred at r.t. for 20 minutes. The solvent was removed in vacuo and the residue was then partitioned between DCM and saturated aqueous NaHCO$_3$ solution. The aqueous phase was extracted with further DCM and the combined organic fractions were dried (MgSO$_4$), evaporated in vacuo and purified by column chromatography (SiO$_2$, 60% EtOAc in hexane) to give the title compound (1.25 g, 90%) as a pale yellow foam. $\delta_H$ (CDCl$_3$) 8.42-8.65 (m, 3H), 7.95 (d, J 7.1 Hz, 1H), 7.86 (d, J 8.2 Hz, 1H), 7.55 (t, J 7.8 Hz, 1H), 7.24-7.40 (m, 2H), 2.15-2.32 (br s, 2H), 1.50-1.80 (br s, 3H). LCMS (ES+) 352 (M+H)$^+$, RT 1.81 minutes.

Intermediate 13

2-Methylpropane-2(S)-sulfinic acid N-[8-chloro-2-(2-methylpyridin-3-yl)quinolin-3-yl]-meth-(E)-ylideneamide A mixture of Intermediate 9 (5.0 g, 15.2 mmol), 2-methylpyridin-3-ylboronic acid pinacol ester (5 g, 22.43 mmol), tetrakis(triphenylphosphine)palladium(0) (0.2 g, 0.17 mmol) and 2M aqueous sodium bicarbonate solution (20 mL) in 1,4-dioxane (80 mL) was degassed and heated under refluxed in a nitrogen atmosphere for 3 h. The reaction mixture was cooled to room temperature, partitioned between EtOAc and brine, and the aqueous layer was extracted once more using EtOAc. The combined organic extracts were dried (MgSO$_4$) and the solvent was removed under reduced pressure. To a solution of the resulting material in 2-propanol (10 mL) was added a solution prepared by stirring potassium phosphate (2.8 g, 13.21 mmol) and (S)-2-methyl-2-propanesulfinamide (1.85 g, 15.3 mmol) in water (10 mL) for 15 minutes. The reaction mixture was stirred for 1 h. Ice-water was added and the resulting material was extracted using DCM. The organic extract was dried (MgSO$_4$) and the solvent was removed in in vacuo. Column chromatography (SiO$_2$, 50-60% EtOAc in hexane) gave the title compound (4.3 g, 73%) as pale yellow foam. $\delta_H$ (CDCl$_3$) 8.91 (s, 1H), 8.66 (dd, J 5.0, 1.7 Hz, 1H), 8.55 (s, 1H), 7.97 (m, 2H), 7.67 (dd, J 7.7, 1.6 Hz, 1H), 7.60 (m, 1H), 7.33 (dd, J 7.6, 5.0 Hz, 1H), 2.30 (s, 3H), 1.24 (s, 9H). LCMS (ES+) 386 (M+H)$^+$, RT 1.49 minutes.

Intermediate 14

2-Methylpropane-2(S)-sulfinic acid {(R)-1-[8-chloro-2-(2-methylpyridin-3-yl)quinolin-3-yl]-2,2,2-trifluoroethyl}amide A solution of Intermediate 13 (4.3 g, 11.17 mmol) and tetrabutylammonium difluorotriphenylsilicate (7.5 g, 13.9 mmol) in anhydrous THF (60 mL) was cooled to −50° C. under nitrogen and (trifluoromethyl)trimethylsilane (4.5 mL, 30.5 mmol) was added dropwise. The mixture was stirred for 2 h, allowing the temperature to rise slowly to room temperature. The mixture was cooled down again to −20° C., saturated aqueous ammonium chloride solution was added and the reaction mixture was allowed to warm to room temperature. The reaction mixture was extracted twice using DCM, then the organic extracts were dried (MgSO$_4$) and filtered, and the solvent was evaporated in vacuo. The residue was purified by column chromatography (SiO$_2$, 60% EtOAc in hexane). Fractions containing pure required isomer were bulked and the solvent was removed under reduced pressure to give the title compound (3.2 g, 63%) as a pale yellow syrup. $\delta_H$ (DMSO-d$_6$) 8.98 (d, J 17.8 Hz, 1H), 8.59 (dd, J 4.9, 1.7 Hz, 1H), 8.04 (m, 2H), 7.66 (t, J 7.9 Hz, 1H), 7.47 (m, 2H), 6.52 (m, 1H), 4.55-4.78 (m, 1H), 2.43 (br s, 3H), 1.10 (br s, 9H). LCMS (ES+) 456 (M+H)$^+$, RT 1.5 minutes.

Intermediate 15

(R)-1-[8-Chloro-2-(2-methylpyridin-3-yl)quinolin-3-yl]-2,2,2-trifluoroethylamine To a solution of Intermediate 14 (3.5 g, 7.03 mmol) in 1,4-dioxane (8 mL) was added a 4N solution of HCl in 1,4-dioxane (15 mL). The mixture was stirred at room temperature for 1 h. The solvent was removed in vacuo and the residue was then partitioned between DCM and saturated aqueous NaHCO$_3$ solution. The organic extract was dried (MgSO$_4$). The solvent was removed under reduced pressure to give the title compound as a pale yellow gum. LCMS (ES+) 352 (M+H)$^+$, RT 1.36 minutes.

Intermediate 16

2-Methylpropane-2(S)-sulfinic acid N-[8-chloro-2-(5-methylpyridin-3-yl)quinolin-3-yl]-meth-(E)-ylideneamide A mixture of Intermediate 9 (2.0 g, 6.08 mmol), 5-methylpyridin-3-ylboronic acid pinacol ester (1.6 g, 7.31 mmol), tetrakis(triphenylphosphine)palladium(0) (0.35 g, 0.31 mmol) and 2M aqueous sodium bicarbonate solution (5 mL) in 1,4-dioxane (25 mL) was degassed and heated under reflux in a nitrogen atmosphere for 2 h. The reaction mixture was cooled to room temperature, partitioned between DCM and brine, and the aqueous layer was extracted once more using EtOAc. The combined organic extracts were dried (MgSO$_4$) and the solvent was removed under reduced pressure. To a solution of the resulting material in 2-propanol (10 mL) was added a solution prepared by stirring potassium phosphate (1.2 g, 5.66 mmol) and (S)-2-methyl-2-propanesulfinamide (0.75 g, 6.2 mmol) in water (10 mL) for 15 minutes. The reaction mixture was stirred overnight, then incubated at 60° C. for a further 24 h. DCM was added and washed with brine, the organic extract was dried (MgSO$_4$) and the solvent was removed in in vacuo. Column chromatography (SiO$_2$, 50-60% EtOAc in hexane) gave the title compound (2.28 g, 97%) as a pale yellow foam. $\delta_H$ (CDCl$_3$) 8.93 (s, 1H), 8.81 (s, 1H), 8.63 (m, 1H), 7.98 (m, 2H), 7.69 (m, 1H), 7.61 (m, 1H), 7.50 (m, 1H), 2.54 (s, 3H), 1.31 (s, 9H). LCMS (ES+) 386 (M+H)$^+$, RT 1.56 minutes.

Intermediate 17

2-Methylpropane-2(S)-sulfinic acid {(R)-1-[8-chloro-2-(5-methylpyridin-3-yl)quinolin-3-yl]-2,2,2-trifluoroethyl}amide A solution of Intermediate 16 (2.28 g, 5.91 mmol) and tetrabutylammonium difluorotriphenylsilicate (3.83 g, 7.09 mmol) in anhydrous THF (60 mL) was cooled to −50° C. under nitrogen and (trifluoromethyl)trimethylsilane (2.1 mL, 14.23 mmol) was added dropwise. The mixture was stirred for 2 h, allowing the temperature to rise slowly to 0° C. The reaction mixture was cooled down again to −10° C., saturated aqueous ammonium chloride solution was added and the reaction mixture was allowed to warm to room temperature. The reaction mixture was extracted twice using DCM, then the organic extracts were dried (MgSO$_4$) and the solvent was evaporated in vacuo. The residue was purified by column chromatography (SiO$_2$, 50-60% EtOAc in hexane). Crystallisation from ether/hexane gave the title compound (1.2 g, 44%) as a white crystalline solid. $\delta_H$ (DMSO-$d_6$) 9.00 (s, 1H), 8.65 (d, J 1.5 Hz, 1H), 8.59 (d, J 2.0 Hz, 1H), 8.12 (m, 2H), 7.84 (m, 1H), 7.73 (m, 1H), 6.66 (d, J 8.3 Hz, 1H), 5.04 (m, 1H), 2.45 (s, 3H), 1.16 (s, 9H). LCMS (ES+) 456 (M+H)$^+$, RT 1.55 minutes.

Intermediate 18

(R)-1-[8-Chloro-2-(5-methylpyridin-3-yl)quinolin-3-yl]-2,2,2-trifluoroethylamine To a solution of Intermediate 17 (1.2 g, 2.63 mmol) in DCM (3 mL) was added a 4N solution of HCl in 1,4-dioxane (10 mL). The mixture was stirred at room temperature for 20 minutes. The solvent was removed in vacuo and the residue was then partitioned between DCM and saturated aqueous NaHCO$_3$ solution. The aqueous phase was extracted once more using DCM and the combined organic extracts were dried (MgSO$_4$) and evaporated in vacuo to give the title compound (0.9 g, 97%) as a pale yellow gum. LCMS (ES+) 352 (M+H)$^+$, RT 1.41 minutes.

Intermediate 19

8-Chloro-2-(pyrazin-2-yl)quinoline-3-carbaldehyde

A mixture of 2,8-dichloroquinoline-3-carbaldehyde (2.3 g, 10.18 mmol), 2-(tributylstannanyl)pyrazine (4.5 g, 12.2 mmol) and tetrakis(triphenylphosphine)-palladium(0) (0.4 g, 0.35 mmol) in 1,4-dioxane (25 mL) was degassed and the mixture was heated under nitrogen at 110° C. for 5 h. The mixture was allowed to cool to room temperature overnight and the solidified product was collected by filtration and washed repeatedly with ether. The filtrate was concentrated and left in a refrigerator for 2 h to give a second crop, which was filtered, washed with ether and combined with the bulk material to give the title compound (2.74 g, 99%) as a yellow crystalline solid. LCMS (ES+) 270 (M+H)$^+$, RT 1.41 minutes.

Intermediate 20

2-Methylpropane-2(S)-sulfinic acid N-[8-chloro-2-(pyrazin-2-yl)quinolin-3-yl]meth-(E)-ylideneamide Titanium(IV) isopropoxide (6.1 mL, 20.62 mmol) was added to a stirred suspension of Intermediate 19 (2.74 g, 10.2 mmol) in anhydrous THF (30 mL). The mixture was stirred at room temperature for 10 minutes, then (S)-2-methyl-2-propanesulfinamide (1.35 g, 11.16 mmol) was added and the mixture was stirred at 50° C. for 2 h. Ice-water was added and the mixture was stirred for 10 minutes. The resulting solid was filtered, washed with water and dried in air. The solid was placed in a sintered funnel and extracted three times using hot DCM. The DCM extracts were concentrated under reduced pressure to give the title compound (1.1 g, 29%) as a brown gum. $\delta_H$ (DMSO-$d_6$) 9.18 (s, 1H), 8.91 (m, 1H), 8.28 (m, 2H), 8.13 (m, 2H), 7.74 (m, 2H), 1.26 (s, 9H). LCMS (ES+) 373 (M+H)$^+$, RT 1.58 minutes.

Intermediate 21

2-Methylpropane-2(S)-sulfinic acid {(R)-1-[8-chloro-2-(pyrazin-2-yl)quinolin-3-yl]-2,2,2-trifluoroethyl}amide A mixture of Intermediate 20 (1.1 g, 2.95 mmol) and tetrabutylammonium difluorotriphenylsilicate (1.9 g, 3.52 mmol) in anhydrous THF (25 mL) was stirred at −50° C. (Trifluoromethyl)trimethylsilane (1.1 mL, 7.45 mmol) was added dropwise and the mixture was stirred for 2 h, allowing the temperature to rise slowly. The reaction mixture was cooled again to −20° C., brine was added and the reaction mixture was allowed to warm over 30 minutes. The reaction mixture was extracted twice using DCM, then the organic extracts were dried (MgSO$_4$) and the solvent was evaporated in vacuo. The residue was purified by column chromatography (SiO$_2$, 50-60% EtOAc in hexane) to give the title compound (0.36 g, 28%) as a brown gum. $\delta_H$ (DMSO-$d_6$) 9.39 (s, 1H), 8.95 (s, 1H), 8.77 (m, 2H), 8.04 (m, 2H), 7.69 (m, 1H), 6.83 (m, 1H), 6.65 (d, J 9.5 Hz, 1H), 1.04 (s, 9H). LCMS (ES+) 443 (M+H)$^+$, RT 1.55 minutes.

Intermediate 22

(R)-1-[8-Chloro-2-(pyrazin-2-yl)quinolin-3-yl]-2,2,2-trifluoroethylamine

To a solution of Intermediate 21 (0.36 g, 0.8 mmol) in DCM (2 mL) was added a 4N solution of HCl in 1,4-dioxane (5 mL). The mixture was stirred at room temperature for 20 minutes. The solvent was removed in vacuo and the residue was then partitioned between DCM and saturated aqueous NaHCO$_3$ solution. The aqueous phase was extracted with further DCM and the combined organic fractions were dried (MgSO$_4$) and evaporated. The residue was purified by column chromatography (SiO$_2$, 50% EtOAc in hexane) to give the title compound (0.15 g, 28%) as a brown gum. $\delta_H$ (DMSO-$d_6$) 9.36 (d, J 1.4 Hz, 1H), 9.00 (s, 1H), 8.82 (m, 2H), 8.10 (m, 2H), 7.73 (m, 1H), 5.96 (q, J 7.8 Hz, 1H), 2.86 (br s, 2H). LCMS (ES+) 339 (M+H)$^+$, RT 1.41 minutes.

Intermediate 23

8-Chloro-2-(6-methoxypyrazin-2-yl)quinoline-3-carbaldehyde

A mixture of 2,8-dichloroquinoline-3-carbaldehyde (0.5 g, 2.21 mmol), 2-methoxy-6-(tributylstannanyl)pyrazine (1.0 g, 2.51 mmol) and tetrakis(triphenyl-phosphine)palladium(0) (0.2 g, 0.173 mmol) in 1,4-dioxane (10 mL) was degassed and heated at 110° C. overnight. The mixture was allowed to cool to room temperature and diluted with EtOAc. The resulting solid was collected by filtration, washed with EtOAc, then ether, and dried to give the title compound (0.42 g, 63%) as a yellow solid. $\delta_H$(DMSO-$d_6$) 10.58 (s, 1H), 9.24 (s, 1H), 8.93 (s, 1H), 8.53 (s, 1H), 8.27 (dd, J 8.3, 1.2 Hz, 1H), 8.17 (dd, J 7.5, 1.2 Hz, 1H), 7.75 (m, 1H), 3.96 (s, 3H). LCMS (ES+) 300 (M+H)$^+$, RT 1.51 minutes.

Intermediate 24

2-Methylpropane-2(S)-sulfinic acid N-[8-chloro-2-(6-methoxypyrazin-2-yl)quinolin-3-yl]-meth-(E)-ylideneamide Titanium(IV) isopropoxide (0.85 mL, 2.87 mmol) was added to a stirred suspension of Intermediate 23 (0.42 g, 1.4 mmol) in anhydrous THF (10 mL). The mixture was stirred at room temperature for 10 minutes, then (S)-2-methyl-2-propanesulfinamide (0.2 g, 1.65 mmol) was added and the mixture was stirred at 50° C. for 8 h. Ice-water was added and the mixture was stirred for 10 minutes, then filtered through Celite. The resulting solid was repeatedly washed with EtOAc. The filtrate was washed with brine, dried (MgSO$_4$)

and concentrated in vacuo. The crude material was purified by column chromatography (SiO$_2$, 25% EtOAc in hexane) to give the title compound (0.5 g, 49%) as an off-white solid. $\delta_H$ (DMSO-d$_6$) 9.35 (s, 1H), 9.17 (d, J 0.3 Hz, 1H), 9.13 (s, 1H), 8.50 (m, 1H), 8.29 (dd, J 8.3, 1.2 Hz, 1H), 8.13 (dd, J 7.5, 1.2 Hz, 1H), 7.73 (m, 1H), 4.00 (s, 3H), 1.26 (s, 9H). LCMS (ES+) 403 (M+H)$^+$, RT 1.69 minutes.

Intermediate 25

2-Methylpropane-2(S)-sulfinic acid {(R)-1-[8-chloro-2-(6-methoxypyrazin-2-yl)quinolin-3-yl]-2,2,2-trifluoroethyl}amide A solution of Intermediate 24 (0.5 g, 1.24 mmol) and tetrabutylammonium acetate (0.45 g, 1.5 mmol) in anhydrous THF (15 mL) was stirred at −50° C. under nitrogen and (trifluoromethyl)trimethylsilane (0.4 mL, 2.71 mmol) was added dropwise. The mixture was stirred for 2 h, allowing the temperature to rise slowly to room temperature. The reaction mixture was cooled down again to −10° C. and quenched with brine. The reaction mixture was allowed to warm to room temperature and extracted twice using EtOAc. The combined organic extracts were dried (MgSO$_4$) and the solvent was evaporated in vacuo. The residue was purified by column chromatography (SiO$_2$, 30-50% EtOAc in hexane) to give the title compound (120 mg, 20%) as a pale yellow foam. $\delta_H$ (DMSO-d$_6$) 9.07 (d, J 0.2 Hz, 1H), 9.01 (s, 1H), 8.53 (s, 1H), 8.11 (m, 2H), 7.75 (dd, J 8.1, 7.6 Hz, 1H), 7.07 (m, 1H), 6.80 (d, J 9.3 Hz, 1H), 4.06 (s, 3H), 1.08 (s, 9H). LCMS (ES+) 473 (M+H)$^+$, RT 1.62 minutes.

Intermediate 26

2-Methylpropane-2(S)-sulfinic acid N-[8-chloro-2-(6-methylpyridin-3-yl)quinolin-3-yl]-meth-(E)-ylideneamide A mixture of Intermediate 9 (3.0 g, 9.1 mmol), 2-methylpyridin-5-ylboronic acid (1.24 g, 9.1 mmol) and tetrakis(triphenylphosphine)palladium(0) (0.10 g, 0.1 mmol) in DME (60 mL) was treated with 2M aqueous Na$_2$CO$_3$ solution (11 mL). The reaction mixture was degassed and flushed three times with nitrogen gas, then heated at 90° C. for 20 h. The mixture was allowed to cool to room temperature, and diluted with EtOAc (50 mL). The organic solution was washed with water (50 mL) and brine (50 mL), then dried (MgSO$_4$), and evaporated in vacuo. The resulting crude material was then treated with a mixture of titanium(IV) isopropoxide (5.4 mL, 18.0 mmol) and (S)-2-methyl-2-propanesulfinamide (1.21 g, 10.0 mmol) in anhydrous THF (50 mL), according to the procedure described for Intermediate 2. The title compound (1.46 g, 41%) was obtained as a yellow gum. $\delta_H$ (DMSO-d$_6$) 9.17 (s, 1H), 8.70 (d, J 1.9 Hz, 1H), 8.61 (s, 1H), 8.28 (dd, J 8.3, 1.1 Hz, 1H), 8.11 (dd, J 7.5, 1.3 Hz, 1H), 8.00 (dd, J 7.9, 2.3 Hz, 1H), 7.71 (dd, J 8.1, 7.7 Hz, 1H), 7.50 (d, J 8.1 Hz, 1H), 2.60 (s, 3H), 1.22 (s, 9H). LCMS (ES+) 386 (M+H)$^+$, RT 1.65 minutes.

Intermediate 27

2-Methylpropane-2(S)-sulfinic acid {(R)-1-[8-chloro-2-(6-methylpyridin-3-yl)quinolin-3-yl]-2,2,2-trifluoroethyl}amide Prepared according to the procedure described for Intermediate 3, utilising Intermediate 26 (1.46 g, 3.79 mmol), tetrabutylammonium difluorotriphenylsilicate (2.25 g, 4.17 mmol), (trifluoromethyl)trimethylsilane (1.4 mL, 9.47 mmol) and anhydrous THF (40 mL). The title compound (0.94 g, 55%) was obtained as a yellow gum. $\delta_H$ (DMSO-d$_6$) 9.00 (s, 1H), 8.65 (d, J 1.7 Hz, 1H), 8.13-8.08 (m, 2H), 7.90 (dd, J 7.9, 2.3 Hz, 1H), 7.72 (dd, J 7.9, 7.9 Hz, 1H), 7.52 (d, J 8.1 Hz, 1H), 6.64 (d, J 8.5 Hz, 1H), 5.14-5.03 (m, 1H), 2.62 (s, 3H), 1.15 (s, 9H). LCMS (ES+) 456 (M+H)$^+$, RT 1.70 minutes.

Intermediate 28

(R)-1-[8-Chloro-2-(6-methylpyridin-3-yl)quinolin-3-yl]-2,2,2-trifluoroethylamine Prepared according to the procedure described for Intermediate 4, utilising Intermediate 27 (0.94 g, 2.07 mmol), a 4N solution of HCl in 1,4-dioxane (3 mL, 12.0 mmol) and methanol (18 mL). The title compound (1.28 g, 84%) was obtained as a colourless gum. $\delta_H$ (DMSO-d$_6$) 8.89 (s, 1H), 8.68 (d, J 1.9 Hz, 1H), 8.10 (dd, J 8.3, 1.3 Hz, 1H), 8.04 (dd, J 7.5, 1.3 Hz, 1H), 7.93 (dd, J 7.9, 2.4 Hz, 1H), 7.67 (dd, J 8.1, 8.1 Hz, 1H), 7.47 (d, J 7.9 Hz, 1H), 4.70 (tq, J 7.2, 7.2 Hz, 1H), 2.84 (d, J 7.0 Hz, 2H), 2.60 (s, 3H). LCMS (ES+) 352 (M+H)$^+$, RT 1.51 minutes.

Intermediate 29

4-(Benzotriazol-1-yloxy)pyrido[3,2-d]pyrimidine

In a reactor, under nitrogen charge, ethylene glycol (2.7 L) was heated at 45° C. 3-Aminopyridine-2-carboxylic acid (1.37 kg) and formamidine acetate (1.37 kg) were added. The mixture was heated to 50° C. to facilitate stirring. The mixture was progressively heated to 125° C. (about 1 h) until reaction was complete (2-3 h). After cooling the mixture to 50° C., water (7 L) was added slowly. The suspension was cooled to 20° C. and stirred overnight, then cooled to −5° C. and stirred for 1 h. The resulting solid was isolated by filtration. The cake was washed with cool water (1.5 L) and acetone (1.5 L), and dried under vacuum at 55° C., to give a solid (985 g, 67.5%; HPLC purity 99.25%).

A mixture of this material (10 g, 68.0 mmol) and PyBOP (38.9 g, 74.8 mmol) in acetonitrile (250 mL) was treated with DBU (12.2 mL, 81.6 mmol) and stirred for 2.5 h. The reaction mixture was filtered, and the precipitate was washed with diethyl ether (3×50 mL) and dried under vacuum. The title compound (13.51 g, 75%) was obtained as a cream-coloured solid. $\delta_H$ (DMSO-d$_6$) 9.28 (dd, J 4.2, 1.6 Hz, 1H), 8.82 (s, 1H), 8.59 (dd, J 8.6, 1.5 Hz, 1H), 8.24-8.18 (m, 2H), 7.88-7.85 (m, 1H), 7.69-7.64 (m, 1H), 7.60-7.54 (m, 1H). LCMS (ES+) 265 (M+H)$^+$, RT 1.23 minutes.

Intermediate 30

1-(Pyrido[3,2-d]pyrimidin-4-yloxy)pyrrolidine-2,5-dione

A mixture of Intermediate 29 (13.51 g, 51.0 mmol) and N-hydroxysuccimide (8.83 g, 77 mmol) in dichloromethane (350 mL) was stirred for 20 h. The reaction mixture was filtered, and the filtrate was washed with water, then brine, dried (MgSO$_4$), and evaporated in vacuo. The residue was triturated with diethyl ether, and the precipitate was dried under vacuum. The title compound (10.9 g, 87%) was obtained as a pale yellow solid. $\delta_H$ (DMSO-d$_6$) 9.18 (dd, J 4.1, 1.5 Hz, 1H), 8.94 (s, 1H), 8.52 (dd, J 8.7, 1.7 Hz, 1H), 8.13 (dd, J 8.7, 4.3 Hz, 1H), 2.97 (s, 4H). LCMS (ES+) 245 (M+H)$^+$, RT 0.51 minutes.

Intermediate 31

N-(o-Tolyl)acetamide

Acetic anhydride (33.0 mL, 350 mmol) was added to a stirred solution of o-toluidine (30.0 g, 280 mmol) in dichloromethane (500 mL) at 0° C. The reaction mixture was allowed to warm to room temperature and stirred for 20 h. The reaction mixture was partitioned between DCM and water. The organic phase was washed with brine, then dried (MgSO$_4$) and evaporated in vacuo. The residue was stirred in isohexane at 0° C. for 2 h, then filtered. The precipitate was washed with isohexane and dried under vacuum. The title compound (39.87 g, 95%) was obtained as a pale pink solid. $\delta_H$ (CDCl$_3$) 7.80-7.78 (m, 1H), 7.26-7.20 (m, 2H), 7.13-7.08 (m, 1H), 6.92 (br s, 1H), 2.29 (s, 3H), 2.23 (s, 3H). LCMS (ES+) 150 (M+H)$^+$, RT 0.85 minutes.

Intermediate 32

2-Chloro-8-methylquinoline-3-carbaldehyde

N,N-Dimethylformamide (51.8 mL, 668 mmol) was added portionwise over 15 minutes, with stirring, to phosphorus oxychloride (175 mL, 1.87 mol) at 0° C. The reaction mixture was allowed to warm to room temperature and treated with Intermediate 31 (39.8 g, 267 mmol), then heated to 80° C. and stirred for 72 h. The reaction mixture was cooled to room temperature, then carefully poured portionwise into a vigorously stirred mixture of ice-water. The ice-water mixture was allowed to warm to room temperature over 30 minutes, then filtered. The precipitate was washed with water and dried under vacuum. The title compound (37.3 g, 68%) was obtained as a cream-coloured solid. $\delta_H$ (CDCl$_3$) 10.50 (s, 1H), 8.73 (s, 1H), 7.83 (d, J 8.1 Hz, 1H), 7.76-7.72 (m, 1H), 7.55 (dd, J 7.9, 7.3 Hz, 1H), 2.81 (s, 3H). LCMS (ES+) 206 (M+H)$^+$, RT 1.54 minutes.

Intermediate 33

8-Methyl-2-(pyridin-3-yl)quinoline-3-carbaldehyde

Prepared according to the procedure described for Intermediate 1, utilising Intermediate 32 (10 g, 48.7 mmol), Na$_2$CO$_3$ (7.74 g, 73 mmol), 3-pyridylboronic acid (5.98 g, 48.7 mmol) and tetrakis(triphenylphosphine)palladium(0) (2.81 g, 2.43 mmol) in DME (150 mL) and water (40 mL). The title compound (11.36 g, 94%) was obtained as a brown solid. $\delta_H$ (CDCl$_3$) 10.20 (s, 1H), 9.02 (dd, J 2.3, 0.8 Hz, 1H), 8.86 (s, 1H), 8.80 (dd, J 4.9, 1.7 Hz, 1H), 8.10 (ddd, J 7.9, 2.3, 1.7 Hz, 1H), 7.90 (d, J 8.3 Hz, 1H), 7.78-7.75 (m, 1H), 7.58 (dd, J 8.1, 7.2 Hz, 1H), 7.53 (ddd, J 7.9, 4.9, 0.8 Hz, 1H), 2.88 (s, 3H). LCMS (ES+) 249 (M+H)$^+$, RT 1.41 minutes.

Intermediate 34

2-Methylpropane-2(S)-sulfinic acid N-[8-methyl-2-(pyridin-3-yl)quinolin-3-yl]meth-(E)-ylideneamide Prepared according to the procedure described for Intermediate 2, utilising Intermediate 33 (5 g, 20.2 mmol), titanium(IV) isopropoxide (11.9 mL, 40.3 mmol), (S)-2-methyl-2-propanesulfinamide (2.69 g, 22.0 mmol) and anhydrous THF (60 mL). The title compound (7.8 g, >99%) was obtained as a brown gum. $\delta_H$ (DMSO-d$_6$) 9.08 (s, 1H), 8.85 (dd, J 2.3, 0.8 Hz, 1H), 8.75 (dd, J 4.9, 1.7 Hz, 1H), 8.62 (s, 1H), 8.11-8.07 (m, 2H), 7.82-7.78 (m, 1H), 7.65-7.59 (m, 2H), 2.76 (s, 3H), 1.20 (s, 9H). LCMS (ES+) 352 (M+H)$^+$, RT 1.58 minutes.

Intermediate 35

2-Methylpropane-2(S)-sulfinic acid {(R)-1-[8-methyl-2-(pyridin-3-yl)quinolin-3-yl]-2,2,2-trifluoroethyl}amide Prepared according to the procedure described for Intermediate 3, utilising Intermediate 34 (7.8 g, 22.2 mmol), tetrabutylammonium difluorotriphenylsilicate (13.2 g, 24.4 mmol), (trifluoromethyl)trimethylsilane (3.9 mL, 26.7 mmol) and anhydrous THF (150 mL). The title compound (5.34 g, 57%) was obtained as a yellow gum. $\delta_H$ (DMSO-d$_6$) 8.89 (s, 1H), 8.80-8.77 (m, 2H), 8.03 (ddd, J 7.7, 1.9, 1.9 Hz, 1H), 7.94 (d, J 7.7 Hz, 1H), 7.78-7.75 (m, 1H), 7.68-7.61 (m, 2H), 6.62 (d, J 8.5 Hz, 1H), 5.05 (dq, J 7.9, 7.9 Hz, 1H), 3.17 (s, 3H), 1.15 (s, 9H). LCMS (ES+) 422 (M+H)$^+$, RT 1.56 minutes.

Intermediate 36

(R)-1-[8-Methyl-2-(pyridin-3-yl)quinolin-3-yl]-2,2,2-trifluoroethylamine

Prepared according to the procedure described for Intermediate 4, utilising Intermediate 35 (1.0 g, 2.4 mmol), a 4N solution of HCl in 1,4-dioxane (3.5 mL, 14.0 mmol) and methanol (18 mL). The title compound (611 g, 81%) was obtained as a yellow gum. $\delta_H$ (DMSO-d$_6$) 8.83-8.82 (m, 1H), 8.77 (s, 1H), 8.73 (dd, J 4.7, 1.5 Hz, 1H), 8.04 (ddd, J 7.7, 2.1, 2.1 Hz, 1H), 7.92 (d, J 7.9 Hz, 1H), 7.72-7.69 (m, 1H), 7.62-7.56 (m, 2H), 4.74-4.61 (m, 1H), 2.82 (d, J 7.0 Hz, 2H), 2.70 (s, 3H). LCMS (ES+) 318 (M+H)$^+$, RT 1.41 minutes.

Intermediate 37

7-Fluoro-8-methyl-2-(pyridin-3-yl)quinoline-3-carbaldehyde

Prepared according to the procedure described for Intermediate 1, utilising 2-chloro-7-fluoro-8-methylquinoline-3-carbaldehyde (5.0 g, 22.36 mmol), 3-pyridylboronic acid (3.02 g, 24.6 mmol), tetrakis(triphenylphosphine)palladium (0) (127 mg, 0.11 mmol) and Na$_2$CO$_3$ (3.55 g, 33.54 mmol) in water (30 mL) and DME (60 mL). The title compound (5.52 g, 93%) was obtained as a beige solid. $\delta_H$ (DMSO-d$_6$) 10.13 (s, 1H), 9.08 (s, 1H), 8.95 (dd, J 2.3, 0.8 Hz, 1H), 8.75 (dd, J 4.9, 1.7 Hz, 1H), 8.24 (dd, J 9.0, 6.4 Hz, 1H), 8.16-8.21 (m, 1H), 7.68 (t, J 9.2 Hz, 1H), 7.61 (ddd, J 7.9, 4.0, 0.8 Hz, 1H), 2.66 (d, J 2.4 Hz, 3H). LCMS (ES+) 267 (M+H)$^+$, RT 2.16 minutes.

Intermediate 38

2-Methylpropane-2(S)-sulfinic acid N-[7-fluoro-8-methyl-2-(pyridin-3-yl)quinolin-3-yl]-meth-(E)-ylideneamide Prepared according to the procedure described for Intermediate 2, utilising Intermediate 37 (4.52 g, 16.99 mmol), titanium(IV) isopropoxide (9.66 g, 33.98 mmol), (S)-2-methyl-2-propanesulfinamide (2.27 g, 18.69 mmol) and anhydrous THF (90 mL). The crude material was triturated in diethyl ether (20 mL), and the solid was filtered off and dried under vacuum, to give the title compound (4.37 g, 70%) as a beige solid. $\delta_H$ (DMSO-$d_6$) 9.14 (s, 1H), 8.85 (d, J 1.7 Hz, 1H), 8.76 (dd, J 4.9, 1.5 Hz, 1H), 8.60 (s, 1H), 8.23 (dd, J 9.4, 7.0 Hz, 1H), 8.10 (dt, J 7.9, 1.9 Hz, 1H), 7.59-7.71 (m, 2H), 2.65 (d, J 2.3 Hz, 3H), 1.21 (s, 9H). LCMS (ES+) 370 (M+H)$^+$, RT 1.62 minutes.

Intermediate 39

2-Methylpropane-2(S)-sulfinic acid {(R)-1-[7-fluoro-8-methyl-2-(pyridin-3-yl)quinolin-3-yl]-2,2,2-trifluoroethyl}amide A mixture of Intermediate 38 (4.37 g, 11.83 mmol) and tetrabutylammonium difluorotriphenylsilicate (7.02 g, 13.01 mmol) in anhydrous THF (100 mL) was cooled to −50° C. (Trifluoromethyl)trimethylsilane (2.02 g, 14.2 mmol) was added and the mixture was stirred at −50° C. for 2.5 h. Saturated aqueous ammonium chloride solution (15 mL) was added and the reaction mixture was allowed to warm to r.t. The solvent was removed in vacuo and the residue was partitioned between DCM (100 mL) and water (100 mL). The organic phase was washed with brine (100 mL), dried (phase separator) and evaporated in vacuo. The residue was purified by column chromatography (SiO$_2$, 35-100% EtOAc in hexane) to give the title compound (3.14 g, 60%) as a white foam. $\delta_H$ (DMSO-$d_6$) 8.94 (s, 1H), 8.77-8.81 (m, 2H), 8.00-8.09 (m, 2H), 7.62-7.70 (m, 2H), 6.62 (d, J 8.5 Hz, 1H), 5.05 (quint, J 8.1 Hz, 1H), 2.60 (d, J 2.3 Hz, 3H), 1.15 (s, 9H). LCMS (ES+) 440 (M+H)$^+$, RT 2.56 minutes.

Intermediate 40

(R)-1-[7-Fluoro-8-methyl-2-(pyridin-3-yl)quinolin-3-yl]-2,2,2-trifluoroethylamine Prepared according to the procedure described for Intermediate 4, utilising Intermediate 39 (3.14 g, 7.15 mmol), a 4N solution of HCl in 1,4-dioxane (6 mL, 24.0 mmol) and methanol (30 mL). The title compound (2.40 g, quantitative) was obtained as a yellow oil. $\delta_H$ (DMSO-$d_6$) 8.82-8.85 (m, 2H), 8.74 (dd, J 4.9, 1.7 Hz, 1H), 8.00-8.08 (m, 2H), 7.57-7.64 (m, 2H), 4.69 (q, J 7.7 Hz, 1H), 2.79-2.97 (m, 2H), 2.60 (d, J 2.4 Hz, 3H). LCMS (ES+) 336 (M+H)$^+$, RT 2.20 minutes.

Intermediate 41

7-Fluoro-8-methyl-2-(2-methylpyridin-3-yl)quinoline-3-carbaldehyde

A mixture of 2-chloro-7-fluoro-8-methylquinoline-3-carbaldehyde (8.0 g, 35.77 mmol), 2-methylpyridin-3-ylboronic acid pinacol ester (9.58 g, 39.35 mmol), tetrakis-(triphenylphosphine)palladium(0) (207 mg, 18 mmol) and Na$_2$CO$_3$ (5.69 g, 53.66 mmol) in water (50 mL) and DME (100 mL) was degassed and flushed three times with nitrogen gas, then heated at 90° C. for 24 h. The mixture was allowed to cool to room temperature. The reaction mixture was diluted with DCM (150 mL) and washed with water (150 mL). The aqueous phase was extracted with DCM (2×100 mL) and the combined organic fractions were washed with brine (150 mL), then dried (phase separator) and evaporated in vacuo. The crude material was triturated in hexane (50 mL), then the solid was filtered off and dried under vacuum to give the title compound (9.07 g, 90%) as a pale yellow solid. $\delta_H$ (DMSO-$d_6$) 9.94 (s, 1H), 9.09 (1H, s), 8.61 (dd, J 4.9, 1.7 Hz, 1H), 8.26 (dd, J 8.9, 6.4 Hz, 1H), 7.78 (dd, J 7.7, 1.7 Hz, 1H), 7.69 (t, J 9.2 Hz, 1H), 7.40 (dd, J 7.7, 4.9 Hz, 1H), 2.61 (d, J 2.4 Hz, 3H), 2.34 (s, 3H). LCMS (ES+) 281 (M+H)$^+$, RT 2.26 minutes.

Intermediate 42

2-Methylpropane-2(S)-sulfinic acid N-[7-fluoro-8-methyl-2-(2-methylpyridin-3-yl)-quinolin-3-yl]-meth-(E)-ylideneamide Prepared according to the procedure described for Intermediate 2, utilising Intermediate 41 (5.0 g, 17.84 mmol), titanium(IV) isopropoxide (10.14 g, 35.68 mmol), (S)-2-methyl-2-propanesulfinamide (2.38 g, 19.63 mmol) and anhydrous THF (100 mL). The crude material was triturated in diethyl ether (20 mL), and the solid was filtered off and dried under vacuum to give the title compound (5.14 g, 75%) as a pale yellow solid. $\delta_H$ (DMSO-$d_6$) 9.16 (s, 1H), 8.61 (dd, J 4.9, 1.7 Hz, 1H), 8.37 (s, 1H), 8.22 (dd, J 8.9, 6.4 Hz, 1H), 7.74 (dd, J 7.7, 1.7 Hz, 1H), 7.67 (t, J 9.0 Hz, 1H), 7.40 (dd, J 7.5, 4.9 Hz, 1H), 2.60 (d, J 2.4 Hz, 3H), 2.29 (s, 3H), 1.11 (s, 9H). LCMS (ES+) 384 (M+H)$^+$, RT 2.59 minutes.

Intermediate 43

2-Methylpropane-2(S)-sulfinic acid {(R)-1-[7-fluoro-8-methyl-2-(2-methylpyridin-3-yl)-quinolin-3-yl]-2,2,2-trifluoroethyl}amide Prepared according to the procedure described for Intermediate 39, utilising Intermediate 42 (5.13 g, 13.38 mmol), tetrabutylammonium difluorotriphenylsilicate (7.95 g, 14.72 mmol), (trifluoromethyl)trimethylsilane (4.56 g, 32.12 mmol) and anhydrous THF (100 mL). The title compound (2.64 g, 43%) was obtained as an off-white foam. $\delta_H$ (DMSO-$d_6$, 400 MHz, 110° C.) 8.90 (s, 1H), 8.63 (dd, J 4.8, 1.5 Hz, 1H), 8.00 (dd, J 9.1, 6.3 Hz, 1H), 7.65-7.76 (m, 1H), 7.58 (t, J 9.3 Hz, 1H), 7.40 (dd, J 7.6, 5.1 Hz, 1H), 6.00-6.11 (m, 1H), 4.74-4.87 (m, 1H), 2.59 (d, J 2.5 Hz, 3H), 2.32 (s, 3H), 1.18 (s, 9H). LCMS (ES+) 454 (M+H)$^+$, RT 2.55 minutes.

Intermediate 44

(R)-1-[7-Fluoro-8-methyl-2-(2-methylpyridin-3-yl) quinolin-3-yl]-2,2,2-trifluoroethylamine To a solution of Intermediate 43 (2.64 g, 5.82 mmol) in methanol (25 mL) was added a 4N solution of HCl in 1,4-dioxane (5.0 mL, 20.0 mmol). The mixture was stirred at r.t. overnight. The solvent was removed in vacuo and the residue was dissolved in water (10 mL) and washed with DCM (3×10 mL). The aqueous phase was then basified with 10% aqueous NaOH solution (10 mL) and extracted with DCM (4×25 mL). The combined organic fractions were then dried (phase separator) and evaporated in vacuo to give the title compound (1.76 g, 87%) as a pale yellow solid. $\delta_H$ (DMSO-$d_6$, 400 MHz, 110° C.) 8.75 (s, 1H), 8.60 (dd, J 4.8, 1.8 Hz, 1H), 7.99 (dd, J 8.8, 6.1 Hz, 1H), 7.67-7.71 (m, 1H), 7.53 (t, J 9.3 Hz, 1H), 7.34-7.39 (m, 1H), 4.34-4.46 (m, 1H), 2.60 (d, J 2.5 Hz, 3H), 2.31 (s, 3H). LCMS (ES+) 350 (M+H)$^+$, RT 2.22 minutes.

Intermediate 45

7-Fluoro-8-methyl-2-(5-methylpyridin-3-yl)quinoline-3-carbaldehyde

Prepared according to the procedure described for Intermediate 41, utilising 2-chloro-7-fluoro-8-methylquinoline-3-carbaldehyde (5.0 g, 22.36 mmol), 5-methylpyridin-3-yl-boronic acid (6.95 g, 50.75 mmol), tetrakis(triphenylphosphine)palladium(0) (258 mg, 0.22 mmol) and $Na_2CO_3$ (3.55 g, 33.54 mmol) in water (30 mL) and DME (60 mL). The crude material was triturated in diethyl ether (75 mL), and the solid was filtered off and dried under vacuum to give the title compound (5.0 g, 80%) as a brown solid. $\delta_H$ (DMSO-$d_6$) 10.12 (s, 1H), 9.06 (s, 1H), 8.72 (d, J 1.9 Hz, 1H), 8.60 (d, J 1.5 Hz, 1H), 8.24 (dd, J 9.0, 6.4 Hz, 1H), 7.99 (d, J 0.6 Hz, 1H), 7.68 (t, J 9.2 Hz, 1H), 2.66 (d, J 2.4 Hz, 3H), 2.44 (s, 3H). LCMS (ES+) 281 (M+H)$^+$, RT 1.66 minutes.

Intermediate 46

2-Methylpropane-2(S)-sulfinic acid N-[7-fluoro-8-methyl-2-(5-methylpyridin-3-yl)-quinolin-3-yl]meth-(E)-ylideneamide Prepared according to the procedure described for Intermediate 2, utilising Intermediate 45 (4.99 g, 17.80 mmol), titanium(IV) isopropoxide (10.12 g, 35.60 mmol), (S)-2-methyl-2-propanesulfinamide (2.38 g, 19.6 mmol) and anhydrous THF (100 mL). The title compound (5.63 g, 82%) was obtained as a dark brown solid. $\delta_H$ (DMSO-$d_6$) 9.13 (s, 1H), 8.62 (dd, J 7.7, 1.9 Hz, 2H), 8.59 (s, 1H), 8.22 (dd, J 9.0, 6.4 Hz, 1H), 7.88-7.91 (m, 1H), 7.65 (t, J 9.2 Hz, 1H), 2.65 (d, J 2.4 Hz, 3H), 2.42 (s, 3H), 1.21 (s, 9H). LCMS (ES+) 384 (M+H)$^+$, RT 2.76 minutes.

Intermediate 47

2-Methylpropane-2(S)-sulfinic acid {(R)-1-[7-fluoro-8-methyl-2-(5-methylpyridin-3-yl)-quinolin-3-yl]-2,2,2-trifluoroethyl}amide Prepared according to the procedure described for Intermediate 39, utilising Intermediate 46 (5.63 g, 14.68 mmol), tetrabutylammonium difluorotriphenylsilicate (8.72 g, 16.15 mmol), (trifluoromethyl)trimethylsilane (10.04 g, 70.60 mmol) and anhydrous THF (100 mL). The title compound (3.48 g, 52%) was obtained as a beige solid. $\delta_H$ (DMSO-$d_6$) 8.91 (s, 1H), 8.58-8.68 (m, 2H), 8.05 (dd, J 9.0, 6.4 Hz, 1H), 7.83-7.87 (m, 1H), 7.65 (t, J 9.2 Hz, 1H), 6.62 (d, J 8.3 Hz, 1H), 4.97-5.10 (m, 1H), 2.60 (d, J 2.4 Hz, 3H), 2.44 (s, 3H), 1.17 (s, 9H). LCMS (ES+) 454 (M+H)$^+$, RT 2.66 minutes.

Intermediate 48

(R)-1-[7-fluoro-8-methyl-2-(5-methylpyridin-3-yl)quinolin-3-yl]-2,2,2-trifluoroethylamine Prepared according to the procedure described for Intermediate 44, utilising Intermediate 47 (3.42 g, 7.54 mmol), a 4N solution of HCl in 1,4-dioxane (5.0 mL, 20.0 mmol) and methanol (25 mL). The title compound (2.41 g, 92%) was obtained as a pale yellow solid. $\delta_H$ (DMSO-$d_6$) 8.82 (s, 1H), 8.60 (d, J 1.9 Hz, 1H), 8.57 (dd, J 2.1, 0.6 Hz, 1H), 8.02 (dd, J 8.9, 6.2 Hz, 1H), 7.85 (td, J 2.1, 0.6 Hz, 1H), 7.59 (t, J 9.2 Hz, 1H), 4.60-4.75 (m, 1H), 2.80 (d, J 7.0 Hz, 2H), 2.59 (d, J 2.4 Hz, 3H), 2.43 (s, 3H). LCMS (ES+) 350 (M+H)$^+$, RT 2.39 minutes.

Intermediate 49

2-Amino-3-(trifluoromethyl)benzaldehyde

Manganese dioxide (27 g, 0.32 mol) was added to a solution of [2-amino-3-(trifluoromethyl)phenyl]methanol (12.0 g, 0.063 mol) in DCM (150 mL) and the mixture was stirred for 18 h at room temperature. After this time, more manganese dioxide (27 g, 0.32 mol) was added, and the reaction mixture was left for a further 18 h. The reaction mixture was filtered through Celite, then the solvent was removed in vacuo to afford the title compound (9.5 g, 80%) as an orange oil. $\delta_H$ (DMSO-$d_6$) 9.93 (s, 1H), 7.68 (m, 2H), 6.82 (m, 3H).

Intermediate 50

2-(Pyridin-3-yl)-8-(trifluoromethyl)-1,2-dihydroquinoline-3-carbaldehyde 2,5-Dimethylpyrrolidine hydrochloride (100 mg) was added to a solution of Intermediate 49 (4.1 g, 0.022 mol) and 3-(pyridin-3-yl)acrolein (2.9 g, 0.022 mol) in chloroform (100 mL). The reaction mixture was heated at reflux, with stirring, for 7 days. The reaction mixture was concentrated in vacuo before purification by column chromatography (SiO$_2$, 10-100% EtOAc/DCM), to afford the title compound (3.4 g, 51%) as a pale brown oil. LCMS (ES+) 301.2 (M+H)$^+$, RT 1.29 minutes.

Intermediate 51

2-(Pyridin-3-yl)-8-(trifluoromethyl)quinoline-3-carbaldehyde

Manganese dioxide (4.8 g, 0.056 mol) was added to a solution of Intermediate 50 (3.4 g, 0.011 mol) in chloroform (100 mL) and the reaction mixture was stirred for 18 h. More manganese dioxide (2.0 g) was added, and the mixture was stirred for a further 2 h. The reaction mixture was then filtered through Celite, washing with THF. The filtrate was dried (Na$_2$SO$_4$) and concentrated in vacuo, and was then purified by column chromatography (SiO$_2$, diethyl ether) to afford title compound (505 mg, 15%) as an orange solid. LCMS (ES+) 303.2 (M+H)$^+$, RT 1.29 minutes.

Intermediate 52

2-Methylpropane-2(S)-sulfinic acid N-[2-(pyridin-3-yl)-8-(trifluoromethyl)quinolin-3-yl]-meth-(E)-ylideneamide Titanium(IV) isopropoxide (909 mg, 3.2 mmol) was added to a solution of Intermediate 51 (485 mg, 1.60 mmol) in anhydrous THF (30 mL). The mixture was stirred at r.t. for 10 minutes. (S)-2-Methyl-2-propanesulfinamide (213 mg, 1.76 mmol) was added and the mixture was stirred at r.t. for 18 h. The reaction mixture was then poured onto brine (50 mL) and filtered through Celite, washing with EtOAc. The filtrate was washed with brine, dried (Na$_2$SO$_4$) and concentrated in vacuo. Purification by column chromatography (SiO$_2$, 40-100% EtOAc in hexane) gave the title compound (395 mg, 61%). LCMS (ES+) 406 (M+H)$^+$, RT 1.64 minutes.

Intermediate 53

2-Methylpropane-2(S)-sulfinic acid {(R)-1-[2-(pyridin-3-yl)-8-(trifluoromethyl)quinolin-3-yl]-2,2,2-trifluoroethyl}amide A mixture of Intermediate 52 (320 mg, 0.79 mmol) and tetrabutylammonium difluorotriphenylsilicate (405 mg, 0.75 mmol) in anhydrous THF (20 mL) was cooled to −78° C. (Trifluoromethyl)trimethylsilane (123 mg, 0.87 mmol) was added, and the mixture was allowed to warm to −35° C. and stirred for 30 minutes at that temperature. More (trifluoromethyl)trimethylsilane (123 mg, 0.87 mmol) was added and the mixture was stirred for a further 2 h with the temperature maintained below −35° C. Saturated aqueous ammonium chloride solution (5 mL) was then added and the reaction mixture was allowed to warm to r.t. The solvent was removed in vacuo and the residue was partitioned between EtOAc and water. The aqueous phase was extracted with further EtOAc and the combined organic fractions were washed with brine, dried ($Na_2SO_4$) and evaporated in vacuo. The residue was purified by column chromatography ($SiO_2$, 10-100% EtOAc in DCM) to give the title compound (270 mg, 72%) as a yellow gum. LCMS (ES+) 476 (M+H)$^+$, RT 1.70 minutes.

Intermediate 54

(R)-1-[2-(Pyridin-3-yl)-8-(trifluoromethyl)quinolin-3-yl]-2,2,2-trifluoroethylamine To a solution of Intermediate 53 (243 mg, 0.51 mmol) in methanol (20 mL) was added a 4N solution of HCl in 1,4-dioxane (4 mL, 16.0 mmol). The mixture was stirred at r.t. for 1 h. The solvent was removed in vacuo and the residue was then partitioned between DCM and saturated aqueous $NaHCO_3$ solution and evaporated in vacuo to give the title compound (180 mg, 95%) as a pale yellow gum. LCMS (ES+) 372.2 (M+H)$^+$, RT 1.56 minutes.

Intermediate 55

2-[(Hydroxy)(6-methylpyridin-3-yl)methyl]acrylic acid ethyl ester

To a solution of 6-methylpyridine-3-carbaldehyde (5.0 g, 41 mmol) in ethyl acrylate (10 mL) at room temperature was added DABCO (1.0 g, 9 mmol), and the mixture was stirred overnight. The reaction mixture was concentrated in vacuo and the residue purified by column chromatography ($SiO_2$, hexane to 40% ethyl acetate), to give the title compound (5.6 g, 62%) as a yellow oil. LCMS (ES+) 222.2 (M+H)$^+$, RT 0.98 minutes.

Intermediate 56

2-(6-Methylpyridin-3-yl)-5,6,8-trifluoro-1,4-dihydroquinoline-3-carboxylic acid ethyl ester To a solution of Intermediate 55 (4.2 g, 19.09 mmol), 2,4,5-trifluoro-6-bromo-aniline (4.3 g, 19.09 mmol) and tri(o-tolyl)phosphine (590 mg, 10 mol %) in propionitrile (50 mL) was added triethylamine (9.6 mL, 60 mmol). The reaction mixture was degassed and purged with nitrogen gas before addition of palladium(II) acetate (215 mg, 5 mol %). The reaction mixture was heated to 100° C. overnight. The reaction mixture was diluted with ethyl acetate and the organic phase was washed twice with water. The organic phase was passed through a phase separator and concentrated. The resulting brown gum was purified using column chromatography ($SiO_2$, EtOAc/hexane gradient, 40-80% EtOAc) to give the title compound (3 g, 45%) as an orange oil. LCMS pH 10 (ES+) 349 (M+H)$^+$, RT 1.40 minutes.

Intermediate 57

2-(6-Methylpyridin-3-yl)-5,6,8-trifluoroquinoline-3-carboxylic acid ethyl ester

To a solution of Intermediate 56 (2.8 g, 8.02 mmol) in DCM was added manganese dioxide (2.8 g, 28.73 mmol). The reaction mixture was stirred at r.t. overnight. The reaction mixture was filtered through a celite pad, and the filtrate was concentrated to give the title compound (2.8 g, 100%) as a yellow solid. LCMS pH 10 (ES+) 347 (M+H)$^+$, RT 1.38 minutes.

Intermediate 58

[2-(6-Methylpyridin-3-yl)-5,6,8-trifluoroquinolin-3-yl]methanol

To a solution of Intermediate 57 (2.8 g, 8.1 mmol) in toluene at −78° C. was added DIBAL-H over 20 minutes. The resulting solution was stirred at −78° C. for 60 minutes. The reaction was quenched with 2M NaOH and the resulting solid was removed by filtration. The filtrate was partitioned between EtOAc and water and the aqueous phase was extracted with EtOAc. The combined organic phases were dried, filtered and evaporated to give the title compound (2.5 g, 97%) as an off white solid. LCMS (ES+) 305 (M+H)$^+$.

Intermediate 59

2-(6-Methylpyridin-3-yl)-5,6,8-trifluoroquinoline-3-carbaldehyde

A mixture of Intermediate 58 (2.5 g, 8.2 mmol) and manganese dioxide (3.5 g, 41 mmol) in dichloromethane was stirred at room temperature for 20 h. The reaction mixture was filtered through celite and the resulting yellow solution was concentrated to give the title compound (1.1 g, 44%) as a yellow solid. LCMS (ES+) 303 (M+H)$^+$.

Intermediate 60

2-Methylpropane-2(S)-sulfinic acid N-[2-(6-methylpyridin-3-yl)-5,6,8-trifluoroquinolin-3-yl]meth-(E)-ylideneamide Titanium(IV) isopropoxide (2.1 g, 7.2 mmol) was added to a suspension of Intermediate 59 (1.1 g, 3.6 mmol) in anhydrous THF (30 mL). The mixture was stirred at r.t. for 10 minutes. (S)-2-Methyl-2-propanesulfinamide (480 mg, 3.9 mmol) was added and the mixture was stirred at 60° C. for 1 h. The reaction mixture was concentrated and the residue was purified by column chromatography ($SiO_2$, 40-80% EtOAc in hexane) to give the title compound (1.1 g) as a tan solid. LCMS (ES+) 406 (M+H)$^+$, RT 1.526 minutes.

Intermediate 61

2-Methylpropane-2(S)-sulfinic acid {(R)-1-[2-(6-methylpyridin-3-yl)-5,6,8-trifluoroquinolin-3-yl]-2,2,2-trifluoroethyl}amide A mixture of Intermediate 60 (2.24 g, 6.03 mmol) and tetrabutylammonium difluorotriphenylsilicate (3.58 g, 6.64 mmol) in anhydrous THF (40 mL) was cooled to −40° C. (Trifluoromethyl)trimethylsilane (1.03 g, 7.24 mmol) was added and the mixture was stirred at −40° C. for 1 h. Saturated aqueous ammonium chloride solution (5 mL) was added and the reaction mixture was allowed to warm to r.t. The solvent was removed in vacuo and the residue was partitioned between EtOAc and water. The aqueous phase was extracted with further EtOAc and the combined organic fractions were washed with brine, then dried ($Na_2SO_4$) and evaporated in vacuo. The residue was purified by column chromatography ($SiO_2$, 40-100% EtOAc in hexane) to give the title compound (1.78 g, 67%) as a yellow gum. LCMS (ES+) 476 (M+H)$^+$, RT 1.509 minutes.

Intermediate 62

(R)-1-[2-(6-Methylpyridin-3-yl)-5,6,8-trifluoro quinolin-3-yl]-2,2,2-trifluoroethylamine To a solution of Intermediate 61 (400 mg, 0.84 mmol) in methanol (10 mL) was added a 4N solution of HCl in 1,4-dioxane (10 mL). The mixture was stirred at r.t. for 1 h. The solvent was removed in vacuo and the residue was then partitioned between DCM and saturated aqueous $NaHCO_3$ solution. The aqueous phase was extracted with DCM then dried ($Na_2SO_4$) and evaporated in vacuo to give the title compound (160 mg) as a yellow solid. LCMS (ES+) 372 (M+H)$^+$, RT 1.394 minutes.

Intermediate 63

2-Methylpropane-2(R)-sulfinic acid N-[8-chloro-2-(pyridin-3-yl)quinolin-3-yl]meth-(E)-ylideneamide Titanium(IV) isopropoxide (3.6 g, 12.6 mmol) was added to a suspension of Intermediate 1 (1.7 g, 6.33 mmol) in anhydrous THF (20 mL). The mixture was stirred at r.t. for 10 minutes. (R)-2-Methyl-2-propanesulfinamide (0.84 g, 6.96 mmol) was added and the mixture was stirred at 50° C. for 3 h. The reaction mixture was allowed to cool to r.t. then poured onto brine (50 mL) and filtered through Celite, washing with EtOAc. The filtrate was washed with brine, dried ($Na_2SO_4$) and concentrated in vacuo. Purification by column chromatography ($SiO_2$, 30-100% EtOAc in hexane) gave the title compound (1.88 g, 91%) as a tan solid. $δ_H$ (DMSO-$d_6$) 9.20 (s, 1H), 8.85 (d, J 1.7 Hz, 1H), 8.77 (dd, J 4.9, 1.7 Hz, 1H), 8.61 (s, 1H), 8.29 (dd, J 8.3, 1.1 Hz, 1H), 8.13 (dd, J 7.5, 1.3 Hz, 1H), 8.12-8.08 (m, 1H), 7.72 (dd, J 8.1, 7.7 Hz, 1H), 7.64 (ddd, J 7.7, 4.9, 0.8 Hz, 1H), 1.21 (s, 9H). LCMS (ES+) 372 (M+H)$^+$, RT 2.30 minutes.

Intermediate 64

2-Methylpropane-2(R)-sulfinic acid {(S)-1-[8-chloro-2-(pyridin-3-yl)quinolin-3-yl]-2,2,2-trifluoroethyl}amide A mixture of Intermediate 63 (0.69 g, 1.86 mmol) and tetrabutylammonium difluorotriphenylsilicate (1.1 g, 2.04 mmol) in anhydrous THF (20 mL) was cooled to −78° C. (Trifluoromethyl)trimethylsilane (0.32 g, 2.23 mmol) was added and the mixture stirred at −78° C. to r.t. for 4 h. Saturated aqueous ammonium chloride solution (5 mL) was added. The mixture was partitioned between EtOAc and water. The aqueous phase was extracted with further EtOAc and the combined organic fractions were washed with brine, then dried ($Na_2SO_4$) and evaporated. The residue was purified by column chromatography ($SiO_2$, 65-90% EtOAc in hexane) and then with a second column ($SiO_2$, 20-80% EtOAc in hexane) to give the title compound (0.42 g, 51%) as a pale brown gum. $δ_H$ (DMSO-$d_6$) 9.02 (s, 1H), 8.80 (dd, J 4.9, 1.7 Hz, 1H), 8.78 (dd, J 2.3, 0.6 Hz, 1H), 8.15-8.09 (m, 2H), 8.04-7.99 (m, 1H), 7.77-7.71 (m, 1H), 7.67 (ddd, J 7.9, 4.9, 0.8 Hz, 1H), 6.65 (d, J 8.5 Hz, 1H), 5.12-5.00 (m, 1H), 1.15 (s, 9H). LCMS (ES+) 442 (M+H)$^+$, RT 2.37 minutes.

Intermediate 65

(S)-1-[8-Chloro-2-(pyridin-3-yl)quinolin-3-yl]-2,2,2-trifluoroethylamine

To a solution of Intermediate 64 (0.42 g, 0.952 mmol) in methanol (10 mL) was added a 4N solution of HCl in 1,4-dioxane (1 mL, 4.0 mmol). The mixture was stirred at r.t. for 1 h. The solvent was removed in vacuo and the residue triturated with diethyl ether (×2). The residue was then partitioned between DCM and saturated aqueous $NaHCO_3$ solution. The aqueous phase was extracted with further DCM and the combined organic fractions were washed with brine, then dried ($Na_2SO_4$) and evaporated in vacuo to give the title compound (0.184 g, 57%) as a yellow gum. LCMS (ES+) 338 (M+H)$^+$, RT 1.52 minutes.

Intermediate 66

N—{(S)-1-[8-Chloro-2-(pyridin-3-yl)quinolin-3-yl]-2,2,2-trifluoroethyl}acetamide A solution of Intermediate 65 (0.50 g, 1.48 mmol) in acetic acid (10 mL) was heated at 60° C. for 16 h. The solvent was removed in vacuo and the residue partitioned between DCM and saturated aqueous $NaHCO_3$ solution. The aqueous phase was extracted with further DCM and the combined organic fractions were washed with brine, then dried ($Na_2SO_4$) and evaporated in vacuo to give the title compound (0.55 g, 98%) as a yellow gum. LCMS (ES+) 380.2 (M+H)$^+$, RT 1.27 minutes.

Intermediate 67

N—{(S)-1-[8-Chloro-2-(1-oxypyridin-3-yl)quinolin-3-yl]-2,2,2-trifluoroethyl}acetamide A stirred solution of Intermediate 66 (550 mg, 1.45 mmol) in DCM (30 mL) was cooled to 0° C. MCPBA (650 mg, 2.90 mmol) was added and the mixture was allowed to warm slowly to r.t. over 3 h. The reaction mixture was partitioned between DCM and saturated aqueous $NaHCO_3$ solution. The aqueous phase was extracted with further DCM and the combined organic fractions were washed with brine, dried ($Na_2SO_4$) and evaporated in vacuo. The residue was purified by column chromatography ($SiO_2$, 0-15% MeOH in EtOAc) to give the title compound (506 mg, 88%) as a colourless gum. LCMS (ES+) 396 (M+H)$^+$, RT 1.75 minutes.

Intermediate 68

(S)-1-[8-Chloro-2-(1-oxypyridin-3-yl)quinolin-3-yl]-2,2,2-trifluoroethylamine

A mixture of Intermediate 67 (0.506 g, 1.28 mmol), and conc. HCl (5 mL) in water (5 mL) and ethanol (10 mL) was heated at 70° C. for 40 h. The solvent was removed in vacuo and the residue was partitioned between DCM and saturated aqueous NaHCO$_3$ solution. The aqueous phase was extracted with further DCM and the combined organic fractions were washed with brine, then dried (Na$_2$SO$_4$) and evaporated in vacuo to give the title compound (0.344 g, 76%) as a tan solid. LCMS (ES+) 354.0 (M+H)$^+$, RT 1.41 minutes.

Intermediate 69

2-(Pyridin-3-yl)quinoline-3-carbaldehyde

A mixture of 2-chloroquinoline-3-carbaldehyde (5.0 g, 26.1 mmol), Na$_2$CO$_3$ (4.15 g, 39.1 mmol) and diethyl(3-pyridyl)borane (4.22 g, 28.7 mmol) in DME (100 mL) and water (30 mL) was degassed by bubbling nitrogen gas through it for 5 minutes. Tetrakis-(triphenylphosphine)palladium(0) (0.30 g, 0.261 mmol) was added and the mixture was heated at 90° C. for 5 h. The mixture was allowed to cool to room temperature. The resultant precipitate was filtered off and washed with water (5×50 mL) and diethyl ether (5×50 mL) to give the title compound (4.3 g, 70%) as a pale green solid. LCMS (ES+) 235 (M+H)$^+$, RT 1.53 minutes.

Intermediate 70

2-Methylpropane-2(S)-sulfinic acid N-[2-(pyridin-3-yl)quinolin-3-yl]meth-(E)-ylideneamide Titanium(IV) isopropoxide (6.07 g, 21.4 mmol) was added to a suspension of Intermediate 69 (2.5 g, 10.7 mmol) in anhydrous THF (80 mL). The mixture was stirred at r.t. for 10 minutes. (S)-2-Methyl-2-propanesulfinamide (1.42 g, 11.7 mmol) was added and the mixture was stirred at 50° C. for 3 h. The reaction mixture was allowed to cool to r.t. then poured onto brine (50 mL) and filtered through Celite, washing with EtOAc. The filtrate was washed with brine, dried (Na$_2$SO$_4$) and concentrated in vacuo to give the title compound (3.6 g, 99%) as a tan solid. LCMS (ES+) 338 (M+H)$^+$, RT 2.01 minutes.

Intermediate 71

2-Methylpropane-2(S)-sulfinic acid {(R)-1-[2-(pyridin-3-yl)quinolin-3-yl]-2,2,2-trifluoro-ethyl}amide A mixture of Intermediate 70 (3.6 g, 10.7 mmol) and tetrabutylammonium difluorotriphenylsilicate (6.35 g, 11.8 mmol) in anhydrous THF (60 mL) was cooled to −40° C. (Trifluoromethyl)trimethylsilane (2.28 g, 16.1 mmol) was added and the mixture was stirred at −40° C. for 1 h. Saturated aqueous ammonium chloride solution (5 mL) was added and the reaction mixture was allowed to warm to r.t. The solvent was removed in vacuo and the residue was partitioned between EtOAc and water. The aqueous phase was extracted with further EtOAc and the combined organic fractions were washed with brine, then dried (Na$_2$SO$_4$) and concentrated in vacuo. The residue was purified by column chromatography (SiO$_2$, 60-100% EtOAc in hexane) to give the title compound (1.9 g, 44%) as a yellow gum. LCMS (ES+) 408 (M+H)$^+$, RT 1.80 minutes.

Intermediate 72

(R)-1-[2-(Pyridin-3-yl)quinolin-3-yl]-2,2,2-trifluoroethylamine

To a solution of Intermediate 71 (0.90 g, 2.21 mmol) in methanol (10 mL) was added a 4N solution of HCl in 1,4-dioxane (2 mL, 8.0 mmol). The mixture was stirred at r.t. for 2 h. The solvent was removed in vacuo and the residue was triturated with diethyl ether (×2). The residue was then partitioned between DCM and saturated aqueous NaHCO$_3$ solution. The aqueous phase was extracted with further DCM and the combined organic fractions were washed with brine, then dried (Na$_2$SO$_4$) and evaporated in vacuo to give the title compound (0.86 g, quantitative) as a yellow gum. LCMS (ES+) 304 (M+H)$^+$, RT 1.57 minutes.

Intermediate 73

8-Chloro-2-(6-chloropyridin-3-yl)quinoline-3-carbaldehyde

A mixture of 2,8-dichloroquinoline-3-carbaldehyde (2.6 g, 11.5 mmol), Na$_2$CO$_3$ (1.83 g, 17.3 mmol) and 2-chloropyridin-5-ylboronic acid (1.81 g, 11.5 mmol) in 1,4-dioxane (40 mL) and water (20 mL) was degassed by bubbling nitrogen gas through it for 5 minutes. Tetrakis(triphenylphosphine)palladium(0) (0.13 g, 0.115 mmol) was added and the mixture was heated at 90° C. for 16 h. The mixture was allowed to cool to room temperature. The resultant precipitate was filtered off and washed with water (5×50 mL) and diethyl ether (5×50 mL) to give the title compound (4.3 g, 70%) as a tan solid. LCMS (ES+) 305 (M+H)$^+$, RT 1.54 minutes.

Intermediate 74

2-Methylpropane-2(S)-sulfinic acid N-[8-chloro-2-(6-chloropyridin-3-yl)quinolin-3-yl]meth-(E)-ylideneamide Titanium(IV) isopropoxide (5.04 g, 17.8 mmol) was added to a suspension of Intermediate 73 (2.69 g, 8.88 mmol) in anhydrous THF (80 mL). The mixture was stirred at r.t. for 10 minutes. (S)-2-Methyl-2-propanesulfinamide (1.18 g, 9.77 mmol) was added and the mixture was stirred at 50° C. for 3 h. The reaction mixture was allowed to cool to r.t. then poured onto brine (50 mL) and filtered through Celite, washing with EtOAc. The filtrate was washed with brine, dried (Na$_2$SO$_4$) and concentrated in vacuo. The residue was purified by column chromatography (SiO$_2$, 25-80% EtOAc in hexane) to give the title compound (1.98 g, 55%) as a pale yellow solid. LCMS (ES+) 406.2 (M+H)$^+$, RT 1.68 minutes.

Intermediate 75

2-Methylpropane-2(S)-sulfinic acid {(R)-1-[8-chloro-2-(6-chloropyridin-3-yl)quinolin-3-yl]-2,2,2-trifluoroethyl}amide A mixture of Intermediate 74 (1.97 g, 4.85 mmol) and tetrabutylammonium acetate (1.61 g, 5.34 mmol) in anhydrous THF (50 mL) was cooled to −40° C. (Trifluoro-methyl)trimethylsilane (1.38 g, 9.70 mmol) was added and the mixture was stirred at −40° C. for 2 h. Saturated aqueous ammonium chloride solution (5 mL) was added and the reaction mixture was allowed to warm to r.t. The solvent was removed in vacuo and the residue was partitioned between EtOAc and water. The aqueous phase was extracted with further EtOAc and the combined organic fractions were washed with brine, then dried (Na$_2$SO$_4$) and evaporated in vacuo. The residue was purified by column chromatography (SiO$_2$, 15-65% EtOAc in hexane) to give the title compound (0.50 g, 22%) as a yellow gum. LCMS (ES+) 476 (M+H)$^+$, RT 2.67 minutes.

Intermediate 76

(R)-1-[8-Chloro-2-(6-chloropyridin-3-yl)quinolin-3-yl]-2,2,2-trifluoroethylamine To a solution of Intermediate 75 (0.50 g, 1.05 mmol) in methanol (20 mL) was added a 4N solution of HCl in 1,4-dioxane (5 mL, 20.0 mmol). The mixture was stirred at r.t. for 2 h. The solvent was removed in vacuo and the residue partitioned between DCM and saturated aqueous $NaHCO_3$ solution. The aqueous phase was extracted with further DCM and the combined organic fractions were washed with brine, then dried ($Na_2SO_4$) and evaporated in vacuo. The residue was purified by column chromatography ($SiO_2$, 30-70% EtOAc in hexane) to give the title compound (0.37 g, 95%) as a yellow gum. LCMS (ES+) 372.2 (M+H)$^+$, RT 1.56 minutes.

Intermediate 77

2-[(Hydroxy)(2-methylpyridin-3-yl)methyl]acrylic acid ethyl ester

To 2-methylpyridine-3-carbaldehyde (5 g, 0.04 mol) in ethyl acrylate (10 mL) were added DABCO (1 g, 0.01 mol) and methanol (1 mL). The reaction mixture was stirred at 45° C. for 3 days. The reaction mixture was then concentrated and purified by column chromatography ($SiO_2$, 60-100% EtOAc/DCM) to give the title compound (62%) as a colourless oil. $\delta_H$ (DMSO-$d_6$) 8.32 (dd, J 4.8, 1.7 Hz, 1H), 7.51 (dd, J 7.7, 1.7 Hz, 1H), 7.17 (dd, J 7.7, 4.8 Hz, 1H), 6.28 (t, J 1.3 Hz, 1H), 5.91 (t, J 1.6 Hz, 1H), 5.78 (d, J 5.0 Hz, 1H), 5.62 (d, J 5.0 Hz, 1H), 4.10-4.00 (m, 2H), 3.29 (s, 3H), 1.10 (t, J 7.0 Hz, 3H). LCMS (ES+) 222 (M+H)$^+$, RT 1.11 minutes.

Intermediate 78

2-(2-Methylpyridin-3-yl)-8-(trifluoromethyl)quinoline-3-carboxylic acid ethyl ester To a degassed mixture of 2-amino-3-bromobenzotrifluoride (3.2 g, 17 mmol), Intermediate 77 (3.3 g, 15 mmol), tri(o-tolyl)phosphine (256 mg) and triethylamine (4 mL) in propionitrile (40 mL) at room temperature was added palladium(II) acetate (120 mg, 5 mol %). The mixture was again degassed and heated to 110° C. for 2 h, then diluted with water (20 mL) and EtOAc (100 mL). The aqueous layer was separated and extracted into EtOAc (100 mL). The combined organic fractions were washed with brine (10 mL), dried ($Na_2SO_4$), filtered and concentrated in vacuo to give a yellow oil. The resulting crude material was dissolved in chlorobenzene (30 mL), treated with $MnO_2$ (6 g) and heated at 60° C. for 2 h, then at 100° C. for 4 h. The mixture was filtered through a celite plug (at 70° C.), washed with DCM and concentrated in vacuo. The resulting dark oil was purified by column chromatography ($SiO_2$, hexane to 40% EtOAc) to give the title compound (3.3 g, 66%) as a brown oil. $\delta_H$ (DMSO-$d_6$) 8.87 (s, 1H), 8.59 (dd, J 4.9, 1.7 Hz, 1H), 8.18 (m, 2H), 7.70 (t, J 7.7 Hz, 1H), 7.59 (dd, J 7.7, 1.7 Hz, 1H), 7.23 (dd, J 7.6, 4.9 Hz, 1H), 4.18 (q, J 7.1 Hz, 2H), 2.48 (s, 3H), 1.06 (t, J 7.1 Hz, 3H). LCMS (ES+) 361.2 (M+H)$^+$.

Intermediate 79

2-(2-Methylpyridin-3-yl)-8-(trifluoromethyl)quinoline-3-carbaldehyde

To a cold (−50° C.) solution of Intermediate 79 (3.3 mL, 9.3 mmol) in toluene (50 mL) was added DIBAL-H (27.6 mL of a 1M solution in DCM) dropwise. The mixture was allowed to warm to room temperature over 2 h, stirred at this temperature for a further 30 minutes, then cooled to −78° C., before the dropwise addition of 1M aqueous NaOH solution (45 mL), during which time the temperature was allowed to rise to ambient temperature. The organic phase was separated and the aqueous phase extracted into EtOAc (30 mL). The combined organic fractions were washed with 2M aqueous NaOH solution (3×50 mL), water (50 mL) and brine (50 mL), then dried ($Na_2SO_4$), filtered and concentrated in vacuo to give a pale brown solid (3.1 g). The mixture was treated with $MnO_2$ (1.7 g), heated at 70° C. for 4 h, filtered through a celite plug, washed with DCM and concentrated in vacuo. The resulting crude solid material was washed with diethyl ether to yield the title compound (2.3 g, 78%) as a white powder. $\delta_H$ (DMSO-$d_6$) 9.97 (s, 1H), 9.23 (s, 1H), 8.63 (m, 2H), 8.41 (d, J 7.0 Hz, 1H), 7.92 (t, J 7.8 Hz, 1H), 7.82 (dd, J 7.7, 1.7 Hz, 1H), 7.41 (dd, J 7.5, 5.0 Hz, 1H), 2.39 (s, 3H). LCMS (ES+) 317.2 (M+H)$^+$.

Intermediate 80

2-Methylpropane-2-(S)-sulfinic acid N-[2-(2-methylpyridin-3-yl)-8-(trifluoromethyl)-quinolin-3-yl]meth-(E)-ylideneamide To a solution of Intermediate 79 (2.0 g, 6.3 mmol) in THF (15 mL) at room temperature was added titanium(IV) isopropoxide (3.5 mL). The mixture was stirred for 15 minutes prior to the addition of (S)-2-methyl-2-propanesulfinamide (0.91 g, 7.5 mmol) and then heated at 50° C. for 2 h. After cooling to room temperature, water (10 mL) was added and the resulting precipitate filtered through a celite plug. The filtrate was concentrated in vacuo to give the title compound (2.2 g, 83%) as a pale yellow oil. $\delta_H$ ($CDCl_3$) 8.96 (s, 1H), 8.66 (dd, J 4.9, 1.7 Hz, 1H), 8.58 (s, 1H), 8.22 (d, J 7.9 Hz, 2H), 7.73 (t, J 7.8 Hz, 1H), 7.59 (dd, J 7.7, 1.6 Hz, 1H), 7.30 (m, 1H), 2.06 (s, 3H), 1.26 (s, 9H). LCMS (ES+) 420 (M+H)$^+$.

Intermediate 81

2-Methylpropane-2-(S)-sulfinic acid {(R)-1-[2-(2-methylpyridin-3-yl)-8-(trifluoro-methyl)quinolin-3-yl]-2,2,2-trifluoroethyl}amide To a solution of Intermediate 80 (2.2 g, 5.2 mmol) in THF (25 mL) was added tetrabutylammonium acetate (1.9 g) and the mixture was cooled to −30° C. before the dropwise addition of (trifluoromethyl)trimethylsilane (1.7 mL). After stirring for 1.5 h, brine (25 mL) was added, the mixture was allowed to warm to room temperature, and stirring was continued for a further 15 minutes. EtOAc (50 mL) was added, then the organic fraction was separated, washed with brine (20 mL), water (20 mL) and brine (20 mL), dried ($Na_2SO_4$), filtered and concentrated in vacuo. The resulting pale yellow solid was subjected to column chromatography ($SiO_2$, hexane to 40% EtOAc) to give the title compound (0.90 g, 35%) as a pale yellow oil. $\delta_H$ ($CDCl_3$) 8.52 (dd, J 4.9, 1.6 Hz, 1H), 8.35 (s, 1H), 8.01 (m, 1H), 7.96 (d, J 8.3 Hz, 1H), 7.77 (dd, J 7.6, 1.4 Hz, 1H), 7.54 (t, J 7.6 Hz, 1H), 7.23 (dd, J 7.6, 5.0 Hz, 1H), 4.85 (t, J 7.4 Hz, 1H), 3.83 (d, J 7.7 Hz, 1H), 2.28 (s, 3H), 1.13 (s, 9H). LCMS (ES+) 490.2 (M+H)$^+$.

Intermediate 82

(R)-1-[2-(2-Methylpyridin-3-yl)-8-(trifluoromethyl)quinolin-3-yl]-2,2,2-trifluoroethylamine To a solution of Intermediate 81 (0.86 g, 1.8 mmol) in DCM (10 mL) was added HCl (1.25 mL of a 4M solution in 1,4-dioxane). To the resulting solid suspension was added MeOH (10 mL) and stirring was continued for 10 minutes. The mixture was partitioned between DCM (20 mL) and saturated aqueous NaHCO$_3$ solution (20 mL). The organic phase was separated and the aqueous phase extracted into DCM (10 mL). The combined organic phases were dried (Na$_2$SO$_4$), filtered and concentrated in vacuo to give the title compound (664 mg, >95%) as a pale yellow oil. $\delta_H$ (CDCl$_3$) 8.68 (d, J 4.7 Hz, 1H), 8.62 (s, 1H), 8.16 (m, 2H), 7.71 (t, J 7.9 Hz, 2H), 7.34 (m, 1H), 4.50 (m, 1H), 3.82 (s, 2H), 2.45 (d, J 26.8 Hz, 3H). LCMS (ES+) 386.2 (M+H)$^+$.

Intermediate 83

N—{(R)-1-[2-(2-Methylpyridin-3-yl)-8-(trifluoromethyl)quinolin-3-yl]-2,2,2-trifluoro-ethyl}acetamide Intermediate 82 (660 mg, 1.7 mmol) was dissolved in AcOH (8 mL) and heated at 60° C. overnight and then at 70° C. for 2 h. The mixture was concentrated in vacuo and the residue was purified by column chromatography (SiO$_2$, hexane to 100% EtOAc) to give the title compound (550 mg, 76%) as a white foam. $\delta_H$ (CDCl$_3$) 8.69 (m, 1H), 8.49 (m, 1H), 8.19 (m, 2H), 8.14 (m, 1H), 7.73 (t, J 7.7 Hz, 1H), 7.47 (m, 1H), 6.65 (m, 1H), 5.85 (m, 1H), 2.53 (s, 3H), 2.17 (s, 3H). LCMS (ES+) 428.2 (M+H)$^+$.

Intermediate 84

(R)-1-[2-(2-Methyl-1-oxypyridin-3-yl)-8-(trifluoromethyl)quinolin-3-yl]-2,2,2-trifluoroethylamine To a solution of Intermediate 83 (0.50 g, 1.2 mmol) in DCM (10 mL) at room temperature was added MCPBA (0.46 g) in one portion. After 1.5 h the mixture was partitioned between DCM (50 mL) and 1N aqueous NaOH solution (30 mL). The aqueous layer was acidified with citric acid (10% aqueous) and extracted into DCM (2×20 mL), dried (phase separator) and concentrated in vacuo. The resulting white powder was treated with EtOH (5 mL) and conc. HCl (5 mL) and heated at 55° C. overnight. The mixture was cooled and concentrated in vacuo, and the residue was partitioned between water (10 mL) and DCM (10 mL). Saturated aqueous NaHCO$_3$ solution was added until the aqueous layer was pH 5 and this was extracted into DCM (4×10 mL). The combined organic layers were dried (phase separator) and concentrated in vacuo. The resulting yellow oil was purified by column chromatography (SiO$_2$, 23:2 EtOAc:MeOH) to give the title compound (365 mg, 76%) as a clear oil. $\delta_H$ (CDCl$_3$) 8.57 (s, 1H), 8.43 (d, J 6.1 Hz, 1H), 8.06 (m, 2H), 7.62 (td, J 7.8, 3.6 Hz, 1H), 7.29 (m, 2H), 4.48 (m, 1H), 2.30 (d, J 5.9 Hz, 3H). LCMS (ES+) 402.2 (M+H)$^+$.

Intermediate 85

2-Bromo-6-(methanesulphonyl)phenylamine

2-Bromo-6-(methylsulphanyl)phenylamine (2 g, 10.7 mmol) in DCM (100 mL) was treated with MCPBA (4 g, 23.2 mmol) at r.t. and stirred for 30 minutes. The reaction mixture was washed with saturated aqueous sodium hydrogencarbonate solution, dried over sodium sulphate, filtered and concentrated in vacuo to give the title compound. $\delta_H$ (DMSO-d$_6$) 7.77 (dd, J 7.8, 1.4 Hz, 1H), 7.63 (dd, J 8.0, 1.4 Hz, 1H), 6.73 (t, J 7.9 Hz, 1H), 6.03 (s, 2H), 3.18 (s, 3H). LCMS (ES+) 250 (M+H)$^+$, RT 1.175 minutes.

Intermediate 86

8-(Methanesulfonyl)-2-(2-methylpyridin-3-yl)-1,4-dihydroquinoline-3-carboxylic acid ethyl ester Intermediate 85 (1.2 g, 4.9 mmol), Intermediate 77 (1.2 g, 5.4 mmol), palladium(II) acetate (54.0 mg, 0.05 mmol), tri(o-tolyl)phosphine (149.0 mg, 0.1 mmol) and triethylamine (1.33 mL, 2.0 mmol) in acetonitrile (10 mL) were degassed and heated at 100° C. for 16 h. The reaction mixture was then concentrated in vacuo and purified by column chromatography (SiO$_2$, 60% ethyl acetate/hexanes) to give the title compound (57%) as a pale solid. $\delta_H$ (DMSO-d$_6$) 8.50 (dd, J 4.9, 1.7 Hz, 1H), 8.19 (s, 1H), 7.67-7.60 (dt, J 7.6, 1.7 Hz, 2H), 7.53 (d, J 7.6 Hz, 1H), 7.29 (dd, J 7.6, 4.9 Hz, 1H), 7.16 (t, J 7.7 Hz, 1H), 3.89 (s, 2H), 3.85-3.77 (m, 2H), 3.24 (s, 3H), 2.42 (s, 3H), 0.81 (t, J 7.1 Hz, 3H). LCMS (ES+) 373 (M+H)$^+$, RT 1.49 minutes.

Intermediate 87

8-(Methanesulfonyl)-2-(2-methylpyridin-3-yl)quinoline-3-carboxylic acid ethyl ester Intermediate 86 (880 mg, 2.46 mmol) in DCM (40 mL) was treated portionwise with manganese dioxide (1.0 g) and stirred at 45° C. for 4 h. The reaction mixture was filtered and concentrated in vacuo to give the title compound (79%) as a pale solid. $\delta_H$ (DMSO-d$_6$) 9.24 (s, 1H), 8.63 (dd, J 8.3, 1.4 Hz, 1H), 8.58-8.54 (m, 2H), 7.96 (dd, J 8.1, 7.5 Hz, 1H), 7.68 (dd, J 7.7, 1.7 Hz, 1H), 7.36 (dd, J 7.6, 4.9 Hz, 1H), 4.18-4.11 (q, J 7.1 Hz, 2H), 3.51 (s, 3H), 2.33 (s, 3H), 1.02 (t, J 7.1 Hz, 3H). LCMS (ES+) 371 (M+H)$^+$, RT 1.35 minutes.

Intermediate 88

[8-(Methanesulfonyl)-2-(2-methylpyridin-3-yl)quinolin-3-yl]methanol

Intermediate 87 (1.9 g, 5.3 mmol) in toluene (20 mL) was cooled to −78° C. and treated with DIBAL-H (1M in DCM, 16 mL, 16 mmol). After stirring for 1 h the reaction mixture was quenched with 1M aqueous NaOH solution, extracted into ethyl acetate, dried over sodium sulphate and concentrated in vacuo. The crude material was purified by column chromatography (SiO$_2$, 2% methanol/EtOAc) to give the title compound (59%) as a pale solid. $\delta_H$ (DMSO-d$_6$) 8.71 (s, 1H), 8.59 (dd, J 4.9, 1.7 Hz, 1H), 8.49 (dd, J 8.1, 1.3 Hz, 1H), 8.40 (dd, J 7.4, 1.4 Hz, 1H), 7.85 (dd, J 8.1, 7.4 Hz, 1H), 7.77 (dd, J 7.7, 1.7 Hz, 1H), 7.38 (m, 1H), 5.53 (t, J 5.1 Hz, 1H), 4.52-4.43 (br s, 1H), 4.36 (d, J 4.4 Hz, 1H), 3.49 (s, 3H), 2.26 (s, 3H). LCMS (ES+) 329 (M+H)$^+$, RT 1.10 minutes.

Intermediate 89

8-(Methanesulfonyl)-2-(2-methylpyridin-3-yl)quinoline-3-carbaldehyde

Intermediate 88 (1.8 g, 5.3 mmol) in DCM (80 mL) was treated portionwise with manganese dioxide (2.0 g) and stirred at room temperature for 4 h. The reaction mixture was filtered, concentrated in vacuo and purified by column chromatography (SiO$_2$, EtOAc) to give the title compound (83%) as a pale solid. $\delta_H$ (DMSO-d$_6$) 9.98 (s, 1H), 9.27 (s, 1H), 8.70-8.60 (m, 3H), 7.98 (dd, J 8.1, 7.5 Hz, 1H), 7.82 (dd, J 7.7, 1.7 Hz, 1H), 7.42 (dd, J 7.7, 4.9 Hz, 1H), 3.52 (s, 3H), 2.39 (s, 3H). LCMS (ES+) 327 (M+H)+, RT 1.18 minutes.

Intermediate 90

2-Methylpropane-2(S)-sulphinic acid N-[8-(methanesulphonyl)-2-(2-methylpyridin-3-yl)-quinolin-3-yl]meth-(E)-ylideneamide Intermediate 89 (1.1 g, 3.3 mmol) and (S)-2-methyl-2-propanesulfinamide (436 mg, 6.6 mmol) were mixed and stirred for 10 minutes in anhydrous THF. Titanium(IV) isopropoxide (1.95 mL, 6.6 mmol) was added and the reaction mixture was warmed to 45° C. for 12 h. The reaction mixture was poured onto water, extracted into ethyl acetate, dried over sodium sulphate and concentrated to give the title compound (94%) as a pale solid. LCMS (ES+) 430.0 (M+H)+, RT 1.33 minutes.

Intermediate 91

2-Methylpropane-2(S)-sulfinic acid [(R)-1-(8-methanesulphonyl)-2-(2-methylpyridin-3-yl)quinolin-3-yl)-2,2,2-trifluoroethyl]amide Intermediate 90 (1.4 g, 3.3 mmol) in anhydrous THF was cooled to −40° C. Tetrabutylammonium acetate (1.0 g, 3.6 mmol) was added and the reaction mixture was stirred for 10 minutes. (Trifluoromethyl)trimethylsilane (0.94 g, 6.6 mmol) was then added and the reaction mixture was stirred for 1 h. Saturated aqueous ammonium chloride solution (15 mL) was added and the reaction mixture was allowed to warm to r.t. The solvent was removed in vacuo and the residue was partitioned between DCM and water. The organic phase was washed with brine (30 mL), dried (phase separator) and evaporated in vacuo. The residue was purified by column chromatography (SiO$_2$, 60-100% EtOAc in hexane) to give the title compound (53%) as a white foam. $\delta_H$ (DMSO-d$_6$; 1:1 mixture of rotamers) 9.08 (m, 1H), 8.58 (m, 1H), 8.45 (m, 2H), 7.85 (m, 1H), 7.87 (m, 0.5H), 7.57 (m, 0.5H), 7.34 (m, 1H), 6.53 (m, 1H), 4.64 (m, 1H), 3.40 (s, 3H), 2.29 (s, 1.5H), 2.20 (s, 1.5H), 1.10 (s, 4.5H), 1.04 (s, 4.5H).

Intermediate 92

(R)-1-[8-(Methanesulfonyl)-2-(2-methylpyridin-3-yl)quinolin-3-yl]-2,2,2-trifluoroethylamine Intermediate 91 (1.2 g, 2.5 mmol) in DCM (5 mL) was treated with 4M HCl in 1,4-dioxane (20 mL) and stirred at r.t. for 30 minutes. Methanol (5 mL) was added and the reaction mixture was stirred for a further 30 minutes. The reaction mixture was concentrated and partitioned between DCM and saturated sodium hydrogencarbonate solution. The organic phase was dried and concentrated to give the title compound (96%) as a pale solid. LCMS (ES+) 396.0 (M+H)+, RT 1.25 minutes.

Intermediate 93

2-[(Hydroxy)(pyridin-3-yl)methyl]acrylic acid ethyl ester

To a solution of nicotinaldehyde (10.0 g, 93.4 mmol) in ethyl acrylate (20 mL, ~200 mmol) at room temperature was added DABCO (0.5 g, 4.5 mmol) and the mixture was stirred overnight. Excess ethyl acrylate was removed in vacuo. The resulting crude solid was washed with hexane to give the title compound (18.5 g, 95%) as an off-white solid. $\delta_H$ (CDCl$_3$) 8.62 (d, J 1.7 Hz, 1H), 8.53 (dd, J 4.8, 1.3 Hz, 1H), 7.81 (d, J 7.9 Hz, 1H), 7.28 (s, 1H), 6.42 (s, 1H), 5.93 (s, 1H), 5.63 (s, 1H), 4.18 (m, 2H), 3.20 (br s, 1H), 1.27 (t, J 7.1 Hz, 3H). LCMS (ES+) 208.2 (M+H)+.

Intermediate 94

8-(Methanesulphonyl)-2-(pyridin-3-yl)-1,4-dihydroquinoline-3-carboxylic acid ethyl ester Intermediate 85 (500 mg, 2.0 mmol), Intermediate 93 (455 mg, 2.2 mmol), palladium(II) acetate (22.5 mg, 0.01 mmol), tri(o-tolyl)phosphine (60 mg, 0.02 mmol) and triethylamine (0.56 mL, 4.0 mmol) in acetonitrile (5 mL) were degassed and heated at 120° C. for 3 h. The reaction mixture was concentrated in vacuo and chromatographed (SiO$_2$, 0-100% DCM-ethyl acetate) to give the title compound (440 mg). $\delta_H$ (DMSO-d$_6$) 9.18 (s, 1H), 8.88 (d, J 1.9 Hz, 1H), 8.73 (dd, J 4.8, 1.6 Hz, 1H), 8.61 (dd, J 8.2, 1.3 Hz, 1H), 8.55 (dd, J 7.4, 1.4 Hz, 1H), 8.10 (m, 1H), 7.95 (m, 1H), 7.60 (ddd, J 7.8, 4.8, 0.5 Hz, 1H), 4.27 (q, J 7.1 Hz, 2H), 3.60 (s, 3H), 1.15 (t, J 7.1 Hz, 3H). LCMS (ES+) 359 (M+H)+, RT 1.331 minutes.

Intermediate 95

8-(Methanesulphonyl)-2-(pyridin-3-yl)quinoline-3-carboxylic acid ethyl ester

Intermediate 94 (440 mg, 1.23 mmol) in DCM (20 mL) was treated portionwise with manganese dioxide (500 mg) and stirred at room temperature for 2 h. The reaction mixture was filtered and concentrated in vacuo to give the title compound (355 mg, 80%). $\delta_H$ (DMSO-d$_6$) 9.18 (s, 1H), 8.88 (d, J 1.9 Hz, 1H), 8.73 (dd, J 4.8, 1.6 Hz, 1H), 8.61 (dd, J 8.2, 1.3 Hz, 1H), 8.55 (dd, J 7.4, 1.4 Hz, 1H), 8.10 (m, 1H), 7.95 (m, 1H), 7.60 (m, 1H), 4.27 (q, J 7.1 Hz, 2H), 3.60 (s, 3H), 1.15 (t, J 7.1 Hz, 3H). LCMS (ES+) 357 (M+H)+, RT 1.237 minutes.

Intermediate 96

8-(Methanesulphonyl)-2-(pyridin-3-yl)quinoline-3-carbaldehyde

Intermediate 95 (1.9 g, 5.3 mmol) in toluene (20 mL) was cooled to −78° C. and treated with 1M DIBAL-H (16 mL, 16 mmol) in DCM. After stirring for 1 h, the reaction mixture was quenched with Rochelle salt, extracted into ethyl acetate, dried over sodium sulphate and concentrated in vacuo. The resulting material (1.67 g, 5.3 mmol) was suspended in DCM and treated with manganese dioxide (2 g). After stirring at r.t. for 90 minutes, the reaction mixture was filtered and the residual solid washed with 1:1 methanol-DCM. The filtrate was concentrated in vacuo, then purified by column chromatography (SiO$_2$, DCM-ethyl acetate) to give the title compound (1.0 g). $\delta_H$ (DMSO-d$_6$) 10.19 (s, 1H), 9.25 (s, 1H), 9.01 (dd, J 2.2, 0.6 Hz, 1H), 8.79 (dd, J 4.8, 1.7 Hz, 1H), 8.68 (dd, J 8.2, 1.3 Hz, 1H), 8.59 (dd, J 7.4, 1.4 Hz, 1H), 8.25 (m, 1H), 7.97 (dd, J 8.1, 7.5 Hz, 1H), 7.66 (ddd, J 7.9, 4.8, 0.7 Hz, 1H), 3.62 (s, 3H). LCMS (ES+) 313 (M+H)+, RT 1.084 minutes.

Intermediate 97

2-Methylpropane-2(S)-sulphinic acid N-[8-(methanesulphonyl)-2-(pyridin-3-yl)quinolin-3-yl]meth-(E)-ylideneamide Intermediate 96 (1 g, 3.3 mmol) and (S)-2-methyl-2-propanesulfinamide (436 mg, 6.6 mmol) were mixed and stirred for 10 minutes in THF. Titanium(IV) isopropoxide (1.95 mL, 6.6 mmol) was added and the reaction mixture was warmed to 50° C. for 3 h. The reaction mixture was poured onto water, extracted into ethyl acetate, dried over sodium sulphate, concentrated and chromatographed (SiO$_2$, hexane-DCM) to give the title compound (1.4 g). δ$_H$ (DMSO-d$_6$) 9.32 (s, 1H), 8.92 (d, J 2.0 Hz, 1H), 8.80 (dd, J 4.8, 1.5 Hz, 1H), 8.67 (m, 2H), 8.55 (dd, J 7.3, 1.2 Hz, 1H), 8.16 (dt, J 7.9, 1.9 Hz, 1H), 7.95 (t, J 7.8 Hz, 1H), 7.68 (dd, J 7.7, 4.8 Hz, 1H), 3.62 (s, 3H), 1.25 (s, 9H). LCMS (ES+) 416 (M+H)$^+$, RT 1.311 minutes.

Intermediate 98

2-Methylpropane-2(S)-sulfinic acid {(R)-1-[8-(methanesulfonyl)-2-(pyridin-3-yl)-quinolin-3-yl]-2,2,2-trifluoroethyl}amide Intermediate 97 (1.37 g, 3.3 mmol) in THF was cooled to −40° C. Tetrabutylammonium difluorotriphenylsilicate (1.96 g, 3.63 mmol) was added and the reaction mixture was stirred for 10 minutes. (Trifluoromethyl)trimethylsilane (0.94 g, 6.6 mmol) was added and the reaction mixture was stirred for 1 h. The reaction mixture was poured onto a saturated aqueous solution of Rochelle salt, then extracted into DCM, dried over sodium sulphate and concentrated in vacuo. Chromatography (60% water; 40% methanol) on reverse phase silica gave the title compound (1.2 g). δ$_H$ (DMSO-d$_6$) 9.14 (s, 1H), 8.84 (m, 2H), 8.53 (m, 2H), 8.08 (m, 1H), 7.96 (dd, J 8.1, 7.5 Hz, 1H), 7.70 (ddd, J 7.8, 4.9, 0.6 Hz, 1H), 6.68 (d, J 8.4 Hz, 1H), 5.16 (t, J 8.0 Hz, 1H), 3.57 (s, 3H), 1.17 (s, 9H). LCMS (ES+) 486 (M+H)$^+$, RT 1.341 minutes.

Intermediate 99

(R)-1-[8-(Methanesulfonyl)-2-(pyridin-3-yl)quinolin-3-yl]-2,2,2-trifluoroethylamine Intermediate 98 (1.2 g, 2.47 mmol) in DCM (5 mL) was treated with 4M HCl in 1,4-dioxane (20 mL) and stirred at r.t. for 30 minutes. Methanol (5 mL) was added and the reaction mixture was stirred for a further 30 minutes. The reaction mixture was concentrated and partitioned between DCM and saturated aqueous sodium hydrogencarbonate solution, dried and concentrated to give the title compound (870 mg). δ$_H$ (DMSO-d$_6$) 9.05 (s, 1H), 8.89 (d, J 1.8 Hz, 1H), 8.78 (dd, J 4.8, 1.6 Hz, 1H), 8.50 (m, 2H), 8.12 (m, 1H), 7.92 (m, 1H), 7.66 (m, 1H), 4.79 (m, 1H), 3.61 (s, 3H). LCMS (ES+) 382 (M+H)$^+$, RT 1.171 minutes.

Intermediate 100

N—{(R)-1-[8-Chloro-2-(pyridin-3-yl)quinolin-3-yl]-2,2,2-trifluoroethyl}acetamide Acetic anhydride (4.44 mL, 46.9 mmol) was added to a solution of Intermediate 4 (15.08 g, 44.7 mmol) in THF (150 mL). The reaction mixture was stirred at room temperature for 2 h, and then concentrated to approximately 50 mL volume. The mixture was diluted with EtOAc (200 mL), and the organic solution was washed with saturated aqueous NaHCO$_3$ (3×200 mL) and brine (200 mL), then dried (MgSO$_4$) and evaporated in vacuo to give the title compound (17.0 g, >99%) as a yellow/orange foaming gum. δ$_H$ (DMSO-d$_6$) 9.40 (d, J 8.9 Hz, 1H), 8.85 (s, 1H), 8.79 (dd, J 2.3, 0.6 Hz, 1H), 8.77 (dd, J 4.9, 1.7 Hz, 1H), 8.12 (dd, J 4.5, 1.1 Hz, 1H), 8.09 (dd, J 3.9, 1.1 Hz, 1H), 8.03 (ddd, J 7.8, 1.9, 1.9 Hz, 1H), 7.73 (dd, J 7.9, 7.9 Hz, 1H), 7.62 (ddd, J 7.8, 4.8, 0.7 Hz, 1H), 6.01 (dq, J 8.1, 8.1 Hz, 1H), 1.95 (s, 3H). LCMS (pH 3) (ES+) 380 (M+H)$^+$, RT 1.58 minutes.

Intermediate 101

N—{(R)-1-[8-Chloro-2-(1-oxypyridin-3-yl)quinolin-3-yl]-2,2,2-trifluoroethyl}acetamide 3-Chloroperoxybenzoic acid (13.5 g, 60.4 mmol) was added to a solution of Intermediate 100 (17.0 g, 44.7 mmol) in DCM (250 mL) at 0° C. The reaction mixture was allowed to warm slowly to room temperature over 20 h. The mixture was treated with saturated aqueous NaHCO$_3$ solution (200 mL) and stirred for 3 h. It was then acidified to pH 8 with 10% aqueous HCl, and the organic layer was separated. The aqueous layer was extracted with DCM (2×100 mL), and the combined organic phases were washed with saturated aqueous NaHCO$_3$ (200 mL) and brine (100 mL), then dried (MgSO$_4$) and evaporated in vacuo to give the title compound (17.7 g, >99%) as an orange foaming gum. δ$_H$ (DMSO-d$_6$) 9.36 (d, J 8.7 Hz, 1H), 8.82 (s, 1H), 8.44-8.43 (s, 1H), 8.40 (ddd, J 6.4, 1.7, 0.9 Hz, 1H), 8.15-8.09 (m, 2H), 7.75 (dd, J 7.9, 7.9 Hz, 1H), 7.64-7.59 (m, 1H), 7.54-7.50 (m, 1H), 5.97 (qd, J 8.3, 8.3 Hz, 1H), 1.93 (s, 3H). LCMS (ES+) 396 (M+H)$^+$, RT 1.12 minutes.

Intermediate 102

(R)-1-[8-Chloro-2-(1-oxypyridin-3-yl)quinolin-3-yl]-2,2,2-trifluoroethylamine

A mixture of concentrated HCl (100 mL) and water (65 mL) was added to a solution of Intermediate 101 (17.7 g, 44.7 mmol) in ethanol (165 mL). The reaction mixture was heated to 80° C. and stirred for 3 days. The mixture was cooled to room temperature and concentrated in vacuo to approximately 100 mL volume, and basified to pH 8 with saturated aqueous NaHCO$_3$ solution. The aqueous solution was extracted with 10% methanol/DCM (5×100 mL) and the combined organic layers were passed through a phase separator cartridge, then evaporated. The residue was purified by column chromatography [SiO$_2$, 2-20% (9:1 methanol:28% NH$_4$OH) in DCM], followed by a second column (aminopropyl-SiO$_2$, EtOAc), to give the title compound (13.2 g, 83%) as a foaming brown gum. δ$_H$ (DMSO-d$_6$) 8.93 (s, 1H), 8.48-8.47 (m, 1H), 8.41-8.38 (m, 1H), 8.13 (dd, J 8.3, 1.2 Hz, 1H), 8.07 (dd, J 7.5, 1.2 Hz, 1H), 7.71 (dd, J 7.8, 7.8 Hz, 1H), 7.62 (dd, J 7.7, 6.8 Hz, 1H), 7.56 (ddd, J 7.8, 1.3, 1.3 Hz, 1H), 4.72 (tq, J 7.4, 7.4 Hz, 1H), 2.84 (d, J 6.9 Hz, 2H). LCMS (ES+) 354 (M+H)$^+$, RT 1.31 minutes.

Example 1

N—{(R)-1-[8-Chloro-2-(pyridin-3-yl)quinolin-3-yl]-2,2,2-trifluoroethyl}pyrido[3,2-d]-pyrimidin-4-ylamine A mixture of Intermediate 4 (0.62 g, 1.85 mmol), 4-chloropyrido[3,2-d]-pyrimidine (0.37 g, 2.22 mmol) and DMAP (0.32 g, 2.59 mmol) in DCM (15 mL) was heated under microwave irradiation at 140° C. for 1 h. The reaction mixture was partitioned between DCM and water. The aqueous phase was extracted with further DCM and the combined organic fractions were washed with brine, then dried (Na$_2$SO$_4$) and evaporated in vacuo. The residue was purified by column chromatography (SiO$_2$, 0-20% MeOH in EtOAc) to give the title compound (232 mg, 27%) as a brown gum. δ$_H$ (DMSO-d$_6$) 9.50 (br s, 1H), 9.35 (s, 1H), 8.92 (dd, J 4.3, 1.5 Hz, 1H), 8.77 (d, J 1.8 Hz, 1H), 8.68 (dd, J 4.8, 1.5 Hz, 1H), 8.48 (s, 1H), 8.21 (dd, J 8.3, 1.5 Hz, 1H), 8.13 (dd, J 8.3, 1.0 Hz, 1H), 8.08 (dd, J 7.6, 1.3 Hz, 1H), 8.07-8.04 (m, 1H), 7.92 (dd, J 8.3, 4.0 Hz, 1H), 7.74-7.70 (m, 1H), 7.52 (ddd, J 7.8, 5.1, 0.8 Hz, 1H), 6.81-6.74 (m, 1H). LCMS (ES+) 467 (M+H)$^+$, RT 2.39 minutes.

Example 2

N—{(R)-1-[8-Chloro-2-(1-oxypyridin-3-yl)quinolin-3-yl]-2,2,2-trifluoroethyl}pyrido[3,2-d]-pyrimidin-4-ylamine A stirred solution of Example 1 (144 mg, 0.308 mmol) in DCM (10 mL) was cooled to −10° C. MCPBA (56 mg, 0.325 mmol) was added and the mixture was allowed to warm slowly to r.t. over 3 h. The reaction mixture was partitioned between DCM and saturated aqueous NaHCO$_3$ solution. The aqueous phase was extracted with further DCM and the combined organic fractions were washed with brine, dried (Na$_2$SO$_4$) and evaporated in vacuo. The residue was purified by column chromatography (SiO$_2$, 5-35% MeOH in EtOAc) to give the title compound (54 mg, 36%) as a yellow solid. δ$_H$ (DMSO-d$_6$) 9.55 (d, J 9.0 Hz, 1H), 9.27 (s, 1H), 8.90 (dd, J 4.1, 1.5 Hz, 1H), 8.54 (s, 1H), 8.49 (t, J 1.5 Hz, 1H), 8.26 (ddd, J 6.4, 1.5, 0.9 Hz, 1H), 8.21 (dd, J 8.5, 1.5 Hz, 1H), 8.17-8.07 (m, 2H), 7.91 (dd, J 8.5, 4.1 Hz, 1H), 7.76-7.70 (m, 1H), 7.47-7.51 (m, 1H), 7.37-7.43 (m, 1H), 6.73-6.87 (m, 1H). LCMS (ES+) 483 (M+H)$^+$, RT 2.08 minutes.
Alternative Procedure A mixture of Intermediate 102 (13.1 g, 37 mmol), Intermediate 30 (10.8 g, 44 mmol) and p-toluenesulfonic acid monohydrate (0.70 g, 3.7 mmol) in chloroform (200 mL) was heated to 70° C. under nitrogen for 20 h. The solution was cooled to room temperature, diluted with DCM (200 mL), washed with saturated aqueous NaHCO$_3$ solution (3×200 mL) and brine (200 mL), then dried (MgSO$_4$) and evaporated in vacuo. The residue was dissolved in DCM (30 mL) and filtered to remove an insoluble solid. The filtrate was purified by column chromatography (SiO$_2$, 2-20% MeOH in EtOAc), followed by a second column (aminopropyl-SiO$_2$, EtOAc), to give the title compound (13.45 g, 62%) as a cream-coloured powder.

Example 3

N—[(R)-1-(8-Chloro-2-phenylquinolin-3-yl)-2,2,2-trifluoroethyl]pyrido[3,2-d]pyrimidin-4-ylamine A mixture of Intermediate 8 (0.55 g, 1.63 mmol) and 4-chloropyrido[3,2-d]-pyrimidine (0.31 g, 1.87 mmol) in acetonitrile (5 mL) was stirred at 80° C. for 2.5 h. The reaction mixture was partitioned between DCM and brine. The aqueous phase was extracted with further DCM and the combined organic fractions were washed with brine, then dried (MgSO$_4$) and evaporated in vacuo. The residue was purified by column chromatography (SiO$_2$, 30% EtOAc in hexane) and the product was freeze-dried to give the title compound (35 mg, 2.3%) as a white lyophilised solid. δ$_H$ (DMSO-d$_6$) 9.44 (d, J 9.3 Hz, 1H), 9.37 (s, 1H), 8.93 (dd, J 4.2, 1.5 Hz, 1H), 8.51 (s, 1H), 8.21 (dd, J 8.5, 1.5 Hz, 1H), 8.04-8.11 (m, 2H), 7.92 (dd, J 8.5, 4.2 Hz, 1H), 7.69 (t, J 8.9 Hz, 1H), 7.47-7.61 (m, 5H), 6.88 (m, 1H). LCMS (ES+) 466 (M+H)$^+$, RT 2.78 minutes.

Example 4

N—{(R)-1-[8-Chloro-2-(4-methylpyridin-3-yl)quinolin-3-yl]-2,2,2-trifluoroethyl}pyrido[3,2-d]pyrimidin-4-ylamine A mixture of Intermediate 12 (216 mg, 0.615 mmol) and Intermediate 30 (180 mg, 0.738 mmol) in DCM (15 mL) was heated under microwave irradiation at 140° C. for 1 h. The reaction mixture was diluted with DCM and washed with brine, then dried (MgSO$_4$) and evaporated in vacuo. The residue was purified by column chromatography (SiO$_2$, 0-6% MeOH in EtOAc) to give the title compound (90 mg, 30%) as a brown gum. δ$_H$ (DMSO-d$_6$) 9.54 (br s, 1H), 9.27 (br s, 1H), 8.90 (m, J 4.3, 1H), 8.62 (m, 1H), 8.47 (m, 1H), 8.31 (m, 1H), 8.18-8.24 (m, 3H), 8.08 (m, 1H), 7.91 (m, 1H), 7.20 (m, 1H), 6.57 (m, 1H), 3.35-3.55 (br s, 3H). LCMS (ES+) 481 (M+H)$^+$, RT 1.93 minutes.

Example 5

N—{(R)-1-[8-Chloro-2-(4-methyl-1-oxypyridin-3-yl)quinolin-3-yl]-2,2,2-trifluoroethyl}-pyrido[3,2-d]pyrimidin-4-ylamine A solution of Example 4 (90 mg, 0.187 mmol) in DCM (5 mL) was stirred in an ice-bath under nitrogen, MCPBA (42 mg, 0.187 mmol) was added, and the mixture was allowed to warm slowly to room temperature over 3 h. The reaction mixture was diluted with DCM, then washed with saturated aqueous NaHCO$_3$ solution, dried (MgSO$_4$) and evaporated in vacuo. The residue was purified by column chromatography (SiO$_2$, 6-20% MeOH in EtOAc) then freeze-dried to give the title compound (33 mg, 35%) as a white lyophilised solid. δ$_H$ (DMSO-d$_6$) 9.51-9.60 (m, 1H), 9.02-9.36 (m, 1H), 8.82-8.95 (m, 1H), 8.52-8.56 (m, 1H), 8.05-8.28 (m, 4H), 7.86-7.96 (m, 2H), 7.70-7.78 (m, 1H), 6.52-6.80 (m, 2H), 1.60 (br s, 3H). LCMS (ES+) 497 (M+H)$^+$, RT 1.77 minutes.

Example 6

N—{(R)-1-[8-Chloro-2-(2-methylpyridin-3-yl)quinolin-3-yl]-2,2,2-trifluoroethyl}pyrido[3,2-d]pyrimidin-4-ylamine A mixture of Intermediate 15 (1.38 g, 3.93 mmol), and Intermediate 30 (1.1 g, 4.51 mmol) in DCM (15 mL) was heated under microwave irradiation at 140° C. for 1 h. The reaction mixture was diluted with DCM and washed with brine, then dried (MgSO$_4$) and evaporated in vacuo. The residue was purified by column chromatography (SiO$_2$, 0-5% MeOH in EtOAc) to give the title compound (1.1 g, 58%) as a brown syrup. δ$_H$ (DMSO-d$_6$) 9.51 (m, 1H), 9.29 (m, 1H), 8.91 (m, 1H), 8.51 (m, 1.5H), 8.20 (m, 2.5H), 8.09 (m, 1H), 7.88 (m, 1.5H), 7.72 (m, 1H), 7.61 (m, 0.5H), 7.42 (m, 0.5H), 7.10 (m, 0.5H), 6.57 (m, 1H), 2.22 (s, 1H), 1.99 (s, 2H). LCMS (ES+) 481 (M+H)$^+$, RT 1.47 minutes.

Example 7

N—{(R)-1-[8-Chloro-2-(2-methyl-1-oxypyridin-3-yl)quinolin-3-yl]-2,2,2-trifluoroethyl}-pyrido[3,2-d]pyrimidin-4-ylamine A solution of Example 6 (0.55 g, 1.145 mmol) in DCM (8 mL) was stirred in an ice-bath under nitrogen and 77% MCPBA (0.256 g, 1.143 mmol) was added and stirred overnight. The reaction mixture was diluted with DCM, then washed with saturated aqueous NaHCO$_3$ solution, dried (MgSO$_4$) and evaporated in vacuo. The residue was purified by column chromatography (SiO$_2$, 6-14% MeOH in EtOAc) to give the title compound (300 mg, 53%) as a white foam. $\delta_H$ (DMSO-d$_6$) 9.56 (m, 0.5H), 9.54 (m, 0.5H), 9.28 (m, 0.5H), 9.21 (m, 0.5H), 8.89 (m, 0.5H), 8.86 (m, 0.5H), 8.29-8.35 (m, 2H), 8.17-8.23 (m, 2H), 8.10 (m, 1H), 7.90 (m, 1H), 7.76 (m, 1H), 7.47 (m, 1H), 7.15 (m, 0.5H), 7.08 (m, 0.5H), 6.63 (m, 0.5H), 6.56 (m, 0.5H), 2.19 (s, 1H), 1.59 (s, 2H). LCMS (ES+) 497 (M+H)$^+$, RT 1.31 minutes.

Example 8

N—{(R)-1-[8-Chloro-2-(5-methylpyridin-3-yl) quinolin-3-yl]-2,2,2-trifluoroethyl}-pyrido[3,2-d] pyrimidin-4-ylamine A mixture of Intermediate 18 (0.9 g, 2.56 mmol) and Intermediate 30 (0.75 g, 3.07 mmol) in DCM (15 mL) was heated under microwave irradiation at 140° C. for 1 h. The reaction mixture was diluted with DCM and washed with brine, then dried (MgSO$_4$) and evaporated in vacuo. The residue was purified by column chromatography (SiO$_2$, 0-5% MeOH in EtOAc) to give the title compound (0.48 g, 39%) as a yellow syrup. $\delta_H$ (DMSO-d$_6$) 9.53 (d, J 9.2 Hz, 1H), 9.30 (s, 1H), 8.79-8.94 (m, 1H), 8.42-8.56 (m, 2H), 8.23 (d, J 1.5 Hz, 1H), 8.21 (d, J 1.5 Hz, 1H), 8.06-8.16 (m, 2H), 7.90-7.94 (m, 1H), 7.70-7.83 (m, 2H), 6.74-6.79 (m, 1H), 2.22 (s, 3H). LCMS (ES+) 481 (M+H)$^+$, RT 1.51 minutes.

Example 9

N—{(R)-1-[8-Chloro-2-(5-methyl-1-oxypyridin-3-yl)quinolin-3-yl]-2,2,2-trifluoroethyl}-pyrido[3,2-d] pyrimidin-4-yl-amine A solution of Example 8 (0.48 g, 1 mmol) in DCM (8 mL) was stirred in an ice-bath under nitrogen and 77% MCPBA (0.22 g, 0.98 mmol) was added and stirred overnight. The reaction mixture was diluted with DCM, then washed with saturated aqueous NaHCO$_3$ solution, dried (MgSO$_4$) and evaporated in vacuo. The residue was purified by column chromatography (SiO$_2$, 6-10% MeOH in EtOAc), followed by crystallization from 2-propanol, to give the title compound (155 mg, 31%) as a white crystalline solid. $\delta_H$ (DMSO-d$_6$) 9.53 (d, J 9.0 Hz, 1H), 9.19 (s, 1H), 8.90 (dd, J 4.2, 1.4 Hz, 1H), 8.55 (s, 1H), 8.33 (s, 1H), 8.22 (dd, J 8.5, 1.5 Hz, 1H), 8.17 (dd, J 8.2, 0.9 Hz, 1H), 8.08 (m, 2H), 7.91 (dd, J 8.5, 4.2 Hz, 1H), 7.73 (m, 1H), 7.20 (s, 1H), 6.79 (m, 1H), 2.00 (s, 3H). LCMS (ES+) 497 (M+H)$^+$, RT 1.34 minutes.

Example 10

N—{(R)-1-[8-Chloro-2-(pyrazin-2-yl)quinolin-3-yl]-2,2,2-trifluoroethyl}pyrido[3,2-d]-pyrimidin-4-ylamine A mixture of Intermediate 22 (150 mg, 0.443 mmol) and Intermediate 30 (130 mg, 0.53 mmol) in DCM (4 mL) was heated under microwave irradiation at 140° C. for 1 h. The reaction mixture was diluted with DCM and washed with brine, then dried (MgSO$_4$) and evaporated in vacuo. The residue was purified by column chromatography (SiO$_2$, 60-75% EtOAc in hexane) then freeze-dried to give the title compound (135 mg, 65%) as an off-white lyophilised solid. $\delta_H$ (DMSO-d$_6$) 9.59 (d, J 9.4 Hz, 1H), 9.36 (s, 1H), 9.27 (d, J 1.4 Hz, 1H), 8.91 (dd, J 4.2, 1.3 Hz, 1H), 8.84 (dd, J 2.5, 1.6 Hz, 1H), 8.81 (d, J 2.6 Hz, 1H), 8.41 (s, 1H), 8.15 (m, 3H), 7.90 (dd, J 8.5, 4.2 Hz, 1H), 7.75 (t, J 7.9 Hz, 2H). LCMS (ES+) 468 (M+H)$^+$, RT 1.56 minutes.

Example 11

N—{(R)-1-[8-Chloro-2-(6-methoxypyrazin-2-yl) quinolin-3-yl]-2,2,2-trifluoroethyl}-pyrido[3,2-d] pyrimidin-4-ylamine To a solution of Intermediate 25 (120 mg, 0.25 mmol) in DCM (2 mL) was added a 4N solution of HCl in 1,4-dioxane (5 mL). The mixture was stirred at room temperature for 10 minutes. The solvent was removed in vacuo and the residue was then partitioned between DCM and saturated aqueous NaHCO$_3$ solution. The aqueous phase was extracted with further DCM and the combined organic fractions were dried (MgSO$_4$) and evaporated. A mixture of the resulting material and Intermediate 30 (88 mg, 0.36 mmol) in DCM (4 mL) was heated under microwave irradiation at 140° C. for 1 h. The reaction mixture was diluted with DCM and washed with brine, then dried (MgSO$_4$) and evaporated in vacuo. The residue was twice purified by column chromatography (SiO$_2$, 50% EtOAc in hexane) then freeze-dried to give the title compound (30 mg, 24%) as an off-white lyophilised solid. $\delta_H$ (DMSO-d$_6$) 9.41 (m, 2H), 8.92 (dd, J 4.2, 1.5 Hz, 1H), 8.89 (s, 1H), 8.46 (s, 1H), 8.42 (s, 1H), 8.18 (m, 4H), 7.91 (m, 1H), 7.74 (m, 1H), 4.12 (s, 3H). LCMS (ES+) 498 (M+H)$^+$, RT 1.63 minutes.

Example 12

N—{(R)-1-[8-Chloro-2-(6-methylpyridin-3-yl) quinolin-3-yl]-2,2,2-trifluoroethyl}-pyrido[3,2-d] pyrimidin-4-amine A mixture of Intermediate 28 (614 mg, 1.75 mmol) and Intermediate 30 (469 mg, 1.92 mmol) in DCM (10 mL) was heated under microwave irradiation at 140° C. for 4 h. The reaction mixture was partitioned between DCM and water. The aqueous phase was extracted with further DCM and the combined organic fractions were washed with brine, then dried (MgSO$_4$) and evaporated in vacuo. The residue was purified by column chromatography (SiO$_2$, 0.5-10% MeOH in EtOAc) to give the title compound (679 mg, 81%) as a brown, foaming gum. $\delta_H$ (DMSO-d$_6$) 9.51 (d, J 9.2 Hz, 1H), 9.31 (s, 1H), 8.92 (dd, J 4.1, 1.5 Hz, 1H), 8.63 (d, J 1.9 Hz, 1H), 8.50 (s, 1H), 8.22 (dd, J 8.5, 1.7 Hz, 1H), 8.12 (dd, J 8.3, 1.3 Hz, 1H), 8.06 (dd, J 7.5, 1.3 Hz, 1H), 7.93-7.89 (m, 2H), 7.70 (dd, J 7.9, 7.9 Hz, 1H), 7.34 (d, J 7.9 Hz, 1H), 6.85-6.73 (m, 1H), 2.54 (s, 3H). LCMS (ES+) 481 (M+H)$^+$, RT 2.36 minutes.

Example 13

N—{(R)-1-[8-Chloro-2-(6-methyl-1-oxypyridin-3-yl)quinolin-3-yl]-2,2,2-trifluoroethyl}-pyrido[3,2-d] pyrimidin-4-amine Prepared according to the procedure described for Example 2, utilising Example 12 (679 mg, 1.41 mmol), MCPBA (317 mg, 1.41 mmol) and DCM (30 mL). The title compound (458 mg, 65%) was obtained as a cream-coloured solid. $\delta_H$ (DMSO-d$_6$) 9.51 (d, J 9.0 Hz, 1H), 9.21 (s, 1H), 8.89 (dd, J 4.3, 1.5 Hz, 1H), 8.51 (s, 2H), 8.21 (dd, J 8.5, 1.7 Hz, 1H), 8.15 (dd, J 8.3, 1.1 Hz, 1H), 8.08 (dd, J 7.5, 1.1 Hz, 1H), 7.90 (dd, J 8.5, 4.1 Hz, 1H), 7.73 (dd, J 7.9, 7.9 Hz, 1H), 7.41-7.34 (m, 2H), 6.88-6.77 (m, 1H), 2.35 (s, 3H). LCMS (ES+) 495 (M+H)⁺, RT 2.03 minutes.

Example 14

N—{(R)-1-[8-Methyl-2-(pyridin-3-yl)quinolin-3-yl]-2,2,2-trifluoroethyl}pyrido[3,2-d]-pyrimidin-4-amine Prepared according to the procedure described for Example 1, utilising Intermediate 36 (0.61 g, 1.92 mmol), 4-chloropyrido[3,2-d]pyrimidine (0.38 g, 2.31 mmol) and DMAP (0.59 g, 4.82 mmol) in DCM (15 mL). The title compound (93 mg, 10%) was obtained as a yellow gum. $\delta_H$ (DMSO-$d_6$) 9.52 (d, J 8.9 Hz, 1H), 9.25 (s, 1H), 8.93 (dd, J 4.1, 1.5 Hz, 1H), 8.79 (d, J 1.7 Hz, 1H), 8.69 (dd, J 4.7, 1.5 Hz, 1H), 8.50 (s, 1H), 8.21 (dd, J 8.5, 1.3 Hz, 1H), 8.07 (ddd, J 7.9, 1.9, 1.9 Hz, 1H), 7.94 (d, J 8.7 Hz, 1H), 7.92 (dd, J 8.5, 4.1 Hz, 1H), 7.74 (d, J 6.8 Hz, 1H), 7.62 (dd, J 8.1, 7.5 Hz, 1H), 7.54 (ddd, J 7.9, 4.9, 0.8 Hz, 1H), 6.78 (qd, J 7.7, 7.7 Hz, 1H), 2.69 (s, 3H). LCMS (ES+) 447 (M+H)⁺, RT 2.42 minutes.

Example 15

N—{(R)-1-[8-Methyl-2-(1-oxypyridin-3-yl)quinolin-3-yl]-2,2,2-trifluoroethyl}pyrido[3,2-d]pyrimidin-4-amine Prepared according to the procedure described for Example 2, utilising Example 14 (93 mg, 0.21 mmol), MCPBA (47 mg, 0.21 mmol) and DCM (10 mL). The title compound (45 mg, 47%) was obtained as a cream-coloured solid. $\delta_H$ (DMSO-$d_6$) 9.55 (d, J 9.0 Hz, 1H), 9.20 (s, 1H), 8.91 (dd, J 4.3, 1.5 Hz, 1H), 8.55 (s, 1H), 8.49 (m, 1H), 8.29 (ddd, J 6.4, 1.7, 1.1 Hz, 1H), 8.21 (dd, J 8.5, 1.5 Hz, 1H), 7.95 (d, J 7.9 Hz, 1H), 7.91 (dd, J 8.5, 4.1 Hz, 1H), 7.76-7.73 (m, 1H), 7.64 (dd, J 8.1, 7.3 Hz, 1H), 7.56-7.52 (m, 1H), 7.46 (dd, J 7.7, 6.6 Hz, 1H), 6.79 (qd, J 8.1, 8.1 Hz, 1H), 2.69 (s, 3H). LCMS (ES+) 463 (M+H)⁺, RT 2.02 minutes.

Example 16

N—{(R)-1-[7-Fluoro-8-methyl-2-(pyridin-3-yl)quinolin-3-yl]-2,2,2-trifluoroethyl}-pyrido[3,2-d]pyrimidin-4-amine To a suspension of 4-chloropyrido[3,2-d]pyrimidine (0.66 g, 3.98 mmol) and DMAP (0.49 g, 4.01 mmol) in DCM (14 mL) was added Intermediate 40 (1.12 g, 3.34 mmol). The mixture was heated under microwave irradiation at 140° C. for 1 h. The resulting material was purified by column chromatography (SiO₂, 0-10% MeOH in EtOAc) to give the title compound (626 mg, 40%) as a brown gum. $\delta_H$ (DMSO-$d_6$) 9.50 (d, J 9.0 Hz, 1H), 9.30 (s, 1H), 8.92 (dd, J 4.3, 1.5 Hz, 1H), 8.78-8.81 (m, 1H), 8.69 (dd, J 4.9, 1.7 Hz, 1H), 8.50 (s, 1H), 8.21 (dd, J 8.5, 1.3 Hz, 1H), 8.01-8.10 (m, 2H), 7.92 (dd, J 8.5, 4.1 Hz, 1H), 7.63 (t, J 9.2 Hz, 1H), 7.54 (dd, J 7.9, 4.9 Hz, 1H), 6.70-6.84 (m, 1H), 2.58 (d, J 2.4 Hz, 3H). LCMS (ES+) 465 (M+H)⁺, RT 2.55 minutes.

Example 17

N—{(R)-1-[7-Fluoro-8-methyl-2-(1-oxypyridin-3-yl)quinolin-3-yl]-2,2,2-trifluoroethyl}-pyrido[3,2-d]pyrimidin-4-amine A stirred solution of Example 16 (351 mg, 0.76 mmol) in DCM (10 mL) was cooled to 0° C. MCPBA (131 mg, 0.76 mmol) was added and the mixture was allowed to warm slowly to r.t. over 4 h. The reaction mixture was diluted with DCM (15 mL), washed with saturated aqueous NaHCO₃ solution (25 mL) and brine (25 mL), dried (phase separator) and evaporated in vacuo. The residue was purified by column chromatography (SiO₂, 0-20% MeOH in EtOAc), and the resulting material was freeze-dried from acetonitrile/water, to give the title compound (152 mg, 43%) as a pale yellow solid. $\delta_H$ (DMSO-$d_6$) 9.53 (d, J 8.9 Hz, 1H), 9.24 (s, 1H), 8.91 (dd, J 4.1, 1.5 Hz, 1H), 8.55 (s, 1H), 8.48-8.51 (m, 1H), 8.27-8.31 (m, 1H), 8.21 (dd, J 8.5, 1.5 Hz, 1H), 8.06 (d, J 9.2, 6.6 Hz, 1H), 7.91 (dd, J 8.5, 4.1 Hz, 1H), 7.66 (t, J 9.2 Hz, 1H), 7.51-7.56 (m, 1H), 7.42-7.48 (m, 1H), 6.71-6.85 (m, 1H), 2.59 (d, J 2.3 Hz, 3H). LCMS (ES+) 481 (M+H)⁺, RT 2.07 minutes.

Example 18

N—{(R)-1-[7-Fluoro-8-methyl-2-(2-methylpyridin-3-yl)quinolin-3-yl]-2,2,2-trifluoro-ethyl}pyrido[3,2-d]pyrimidin-4-amine Prepared according to the procedure described for Example 16, utilising Intermediate 44 (0.50 g, 1.43 mmol), 4-chloropyrido[3,2-d]pyrimidine (285 mg, 1.72 mmol) and DMAP (210 mg, 1.72 mmol) in DCM (10 mL). The title compound (307 mg, 45%) was obtained as a yellow foam. $\delta_H$ (DMSO-$d_6$, 400 MHz, 110° C.) 9.13 (s, 1H), 8.87 (dd, J 4.0, 1.5 Hz, 1H), 8.55 (dd, J 4.8, 1.5 Hz, 1H), 8.42 (s, 1H), 8.17 (dd, J 8.3, 1.5 Hz, 1H), 8.05 (dd, J 9.1, 6.3 Hz, 1H), 7.87 (dd, J 8.6, 4.3 Hz, 1H), 7.69 (dd, J 7.6, 1.3 Hz, 1H), 7.56 (t, J 9.1 Hz, 1H), 7.20-7.32 (m, 1H), 6.52 (q, J 8.1 Hz, 1H), 2.58 (d, J 2.5 Hz, 3H), 2.04-2.25 (m, 3H). LCMS (ES+) 479 (M+H)⁺, RT 2.94 minutes.

Example 19

N—{(R)-1-[7-Fluoro-8-methyl-2-(2-methyl-1-oxy-pyridin-3-yl)quinolin-3-yl]-2,2,2-trifluoroethyl}pyrido[3,2-d]pyrimidin-4-amine Prepared according to the procedure described for Example 17, utilising Example 18 (304 mg, 0.64 mmol), MCPBA (110 mg, 0.64 mmol) and anhydrous DCM (10 mL). The title compound (94 mg, 30%) was obtained as a white solid. $\delta_H$ (DMSO-$d_6$, 400 MHz, 110° C.) 9.14 (s, 1H), 8.84-8.90 (m, 1H), 8.35-8.60 (m, 1H), 8.33 (d, J 7.6 Hz, 1H), 8.18 (dd, J 8.6, 1.5 Hz, 1H), 8.07 (dd, J 9.1, 6.3 Hz, 1H), 7.87 (dd, J 8.6, 4.3 Hz, 1H), 7.60 (t, J 9.1 Hz, 1H), 7.10-7.50 (m, 2H), 6.58 (q, J 8.1 Hz, 1H), 2.58 (d, J 2.5 Hz, 3H), 1.64-2.34 (m, 3H). LCMS (ES+) 495 (M+H)⁺, RT 2.08 minutes.

Example 20

N—{(R)-1-[7-Fluoro-8-methyl-2-(5-methylpyridin-3-yl)quinolin-3-yl]-2,2,2-trifluoro-ethyl}pyrido[3,2-d]pyrimidin-4-amine A mixture of Intermediate 48 (500 mg, 1.43 mmol) and Intermediate 30 (420 mg, 1.72 mmol) in DCM (10 mL) was heated under microwave irradiation at 160° C. for 30 minutes. The reaction mixture was diluted with DCM (40 mL) and washed with water (2×50 mL). The aqueous phase was extracted with further DCM (50 mL) and the combined organic fractions were dried (phase separator) and evaporated in vacuo. The residue was purified by column chromatography (SiO₂, 0-10% MeOH in EtOAc) to give the title compound (302 mg, 44%) as a dark blue solid. $\delta_H$ (DMSO-$d_6$) 9.48 (d, J 9.2 Hz, 1H), 9.26 (s, 1H), 8.92 (dd, J 4.3, 1.7 Hz, 1H), 8.58 (d, J 2.1 Hz, 1H), 8.52 (s, 1H), 8.47-8.50 (m, 1H), 8.22 (dd, J 8.5, 1.5 Hz, 1H), 8.05 (dd, J 8.9, 6.2 Hz, 1H), 7.92 (dd, J 8.5, 4.3 Hz, 1H), 7.76-7.80 (m, 1H), 7.63 (t, J 9.0 Hz, 1H), 6.69-6.83 (m, 1H), 2.58 (d, J 2.3 Hz, 3H), 2.26 (s, 3H). LCMS (ES+) 479 (M+H)$^+$, RT 2.63 minutes.

Example 21

N—{(R)-1-[7-Fluoro-8-methyl-2-(5-methyl-1-oxy-pyridin-3-yl)quinolin-3-yl]-2,2,2-trifluoroethyl}pyrido[3,2-d]pyrimidin-4-amine Prepared according to the procedure described for Example 17, utilising Example 20 (300 mg, 0.63 mmol), MCPBA (85 mg, 0.49 mmol) and anhydrous DCM (10 mL). The title compound (101 mg, 32%) was obtained as a white solid. $\delta_H$ (DMSO-$d_6$) 9.50 (d, J 9.0 Hz, 1H), 9.18 (s, 1H). 8.91 (dd, J 4.1, 1.5 Hz, 1H), 8.56 (s, 1H), 8.32 (s, 1H), 8.22 (dd, J 8.7, 1.7 Hz, 1H), 8.05-8.14 (m, 2H), 7.91 (dd, J 8.5, 4.1 Hz, 1H), 7.66 (t, J 9.2 Hz, 1H), 7.26 (s, 1H), 6.71-6.84 (m, 1H), 2.58 (d, J 2.3 Hz, 3H), 2.08 (s, 3H). LCMS (ES+) 495 (M+H)$^+$, RT 2.17 minutes.

Example 22

N—{(R)-1-[2-(Pyridin-3-yl)-8-(trifluoromethyl)quinolin-3-yl]-2,2,2-trifluoroethyl}-pyrido[3,2-d]pyrimidin-4-amine A mixture of Intermediate 54 (180 mg, 0.49 mmol) and Intermediate 30 (179 mg, 0.74 mmol) in DCM (5 mL) was heated under microwave irradiation at 140° C. for 1 h. The reaction mixture was purified by column chromatography (SiO$_2$, EtOAc) to give the title compound (41 mg, 17%) as a brown gum. LCMS (ES+) 501.2 (M+H)$^+$, RT 1.65 minutes.

Example 23

N—{(R)-1-[2-(1-Oxypyridin-3-yl)-8-(trifluoromethyl)quinolin-3-yl]-2,2,2-trifluoroethyl}-pyrido[3,2-d]pyrimidin-4-amine A stirred solution of Example 22 (33 mg, 0.07 mmol) in DCM (5 mL) was cooled (ice bath) and MCPBA (11 mg, 0.05 mmol) was added. The mixture was allowed to stir for 5 h at below 5° C. After this time, the reaction mixture was partitioned between DCM and saturated aqueous Na$_2$CO$_3$ solution. The aqueous phase was extracted with further DCM and the combined organic fractions were dried Na$_2$SO$_4$) and evaporated in vacuo. The residue was purified by column chromatography (SiO$_2$, 0-20% MeOH in EtOAc) to give the title compound (21 mg, 58%) as a pale yellow powder. $\delta_H$ (DMSO-$d_6$) 8.81 (d, J 1.4 Hz, 1H), 8.77 (dd, J 1.5, 4.2 Hz, 1H), 8.63 (s, 1H), 8.53 (s, 1H), 8.30 (dd, J 6.5, 1.0 Hz, 1H), 8.14-8.01 (m, 3H), 7.86 (d, J 8.3 Hz, 1H), 7.76 (d, J 8.0 Hz, 1H), 7.70 (dd, J 4.2, 8.5 Hz, 1H), 7.61 (m, 1H), 7.40, (dd, J 6.7, 7.8 Hz, 1H), 6.56-6.47 (m, 1H). LCMS (ES+) 517.2 (M+H)$^+$, RT 2.06 minutes.

Example 24

N—{(R)-1-[2-(6-Methylpyridin-3-yl)-5,6,8-trifluoroquinolin-3-yl]-2,2,2-trifluoroethyl}-pyrido[3,2-d]pyrimidin-4-amine A mixture of Intermediate 62 (160 mg, 0.43 mmol) and Intermediate 30 (124 mg, 0.51 mmol) in DCM (5 mL) was heated under microwave irradiation at 140° C. for 3 h. The reaction mixture was purified directly using column chromatography (SiO$_2$, 0-5% MeOH in DCM) to give the title compound (210 mg, 93%) as a green solid. LCMS (ES+) 501 (M+H)$^+$, RT 1.481 minutes.

Example 25

N—{(R)-1-[2-(6-Methyl-1-oxypyridin-3-yl)-5,6,8-trifluoroquinolin-3-yl]-2,2,2-trifluoro-ethyl}pyrido[3,2-d]pyrimidin-4-amine A stirred solution of Example 24 (210 mg, 0.42 mmol) in DCM (20 mL) was cooled to 0° C. MCPBA (61 mg, 0.3 mmol) was added and the mixture was allowed to warm slowly to r.t. over 3 h. The reaction mixture was partitioned between DCM and saturated aqueous NaHCO$_3$ solution. The organic layer was extracted using DCM and passed through a phase separator. The resulting yellow solution was evaporated in vacuo. The residue was purified by column chromatography (SiO$_2$, 0-10% MeOH in DCM) to give the title compound (54 mg) as a white freeze-dried solid. $\delta_H$ (DMSO-$d_6$) 9.89 (d, J 9.5 Hz, 1H), 9.48 (s, 1H), 8.92 (dd, J 4.0 Hz, 1H), 8.55 (s, 1H), 8.53 (s, 1H), 8.23-8.13 (m, 2H) 7.93-7.89 (m, 1H), 7.49 (d, J 8.1 Hz, 1H), 7.42 (d, J 5.0 Hz, 1H), 6.92-6.68 (m, 1H), 2.49 (s, 3H). LCMS pH 3 (ES+) 517 (M+H)$^+$, RT 1.886 minutes; LCMS pH 10 (ES+) 517 (M+H)$^+$, RT 1.982 minutes.

Example 26

N—{(R)-1-[8-Chloro-2-(pyridin-3-yl)quinolin-3-yl]-2,2,2-trifluoroethyl}N-methylpyrido[3,2-d]pyrimidin-4-ylamine A stirred solution of Example 1 (92 mg, 0.197 mmol) in DMF (10 mL) was cooled to 0° C. NaH (60%; 9 mg, 0.217 mmol) was added and the mixture was stirred at 0° C. for 5 minutes. Methyl iodide (30 mg, 0.207 mmol) was added and the mixture was stirred at r.t. for 16 h. Water (0.5 mL) was added and the mixture was evaporated in vacuo. The residue was partitioned between DCM and water. The aqueous phase was extracted with further DCM, the combined organic fractions were washed with brine and dried Na$_2$SO$_4$), then the solvent was evaporated in vacuo. The residue was purified twice by column chromatography (SiO$_2$, 0-35% MeOH in EtOAc) to give the title compound (16 mg, 17%) as an off-white solid. $\delta_H$ (DMSO-$d_6$) 9.00 (d, J 1.7 Hz, 1H), 8.77 (dd, J 4.8, 1.6 Hz, 1H), 8.73-8.70 (m, 2H), 8.27 (dt, J 7.8, 1.8 Hz, 1H), 8.11 (dd, J 8.3, 1.2 Hz, 1H), 8.01 (s, 1H), 7.98 (dd, J 7.5, 1.2 Hz, 1H), 7.85 (dd, J 8.5, 1.2 Hz, 1H), 7.71 (dd, J 8.5, 4.4 Hz, 1H), 7.66-7.56 (m, 2H), 5.93 (q, J 7.7 Hz, 1H), 3.53 (s, 3H). LCMS (ES+) 481 (M+H)$^+$, RT 2.31 minutes.

Example 27

N—{(R)-1-[8-Chloro-2-(pyridin-3-yl)quinolin-3-yl]-2,2,2-trifluoroethyl}N-(1-oxypyrido-[3,2-d]pyrimidin-4-yl)amine A stirred solution of Example 1 (955 mg, 2.05 mmol) in DCM (40 mL) was cooled to 0° C. MCPBA (410 mg, 1.84 mmol) was added and the mixture was allowed to warm slowly to r.t. over 3 h. The reaction mixture was partitioned between DCM and saturated aqueous NaHCO$_3$ solution. The aqueous phase was extracted with further DCM and the combined organic fractions were washed with brine, dried Na₂SO₄) and evaporated in vacuo. The residue was purified by column chromatography (SiO₂, 3-60% MeOH in EtOAc) to give the title compound (39 mg, 4%) as a yellow solid. $\delta_H$ (DMSO-d₆) 9.64-9.52 (m, 1H), 9.30 (s, 1H), 9.06 (dd, J 4.2, 1.3 Hz, 1H), 8.78-8.71 (m, 2H), 8.67 (dd, J 4.9, 1.6 Hz, 1H), 8.64 (s, 1H), 8.16-8.01 (m, 4H), 7.75-7.69 (m, 1H), 7.52 (ddd, J 7.8, 4.9, 0.7 Hz, 1H), 6.65-6.52 (m, 1H). LCMS (ES+) 483 (M+H)⁺, RT 1.87 minutes.

Example 28

N—{(R)-1-[8-Chloro-2-(1-oxypyridin-3-yl)quinolin-3-yl]-2,2,2-trifluoroethyl}N-(1-oxy-pyrido[3,2-d]pyrimidin-4-yl)amine Prepared according to the procedure described for Example 27. Later fractions from the column gave the title compound (50 mg, 5%) as a yellow solid. $\delta_H$(DMSO-d₆) 9.79 (br s, 1H), 9.18 (s, 1H), 8.97 (m, 1H), 8.69-8.52 (m, 2H), 8.49 (s, 1H), 8.32-8.27 (m, 1H), 8.14 (dd, J 8.3, 1.2 Hz, 1H), 8.07 (dd, J 7.5, 1.1 Hz, 1H), 8.02-7.93 (m, 1H), 7.71 (t, J 7.9 Hz, 1H), 7.60-7.53 (m, 1H), 7.52-7.45 (m, 1H), 6.56-6.40 (m, 1H). LCMS (ES+) 499 (M+H)⁺, RT 1.53 minutes.

Example 29

N—{(S)-1-[8-Chloro-2-(pyridin-3-yl)quinolin-3-yl]-2,2,2-trifluoroethyl}pyrido[3,2-d]-pyrimidin-4-ylamine A mixture of Intermediate 65 (0.16 g, 0.46 mmol), 4-chloropyrido[3,2-d]-pyrimidine (0.076 g, 0.46 mmol) and DMAP (0.11 g, 0.92 mmol) in DCM (10 mL) was heated under microwave irradiation at 140° C. for 1 h. The reaction mixture was partitioned between DCM and water. The aqueous phase was extracted with further DCM and the combined organic fractions were washed with brine, then dried Na₂SO₄) and evaporated in vacuo. The residue was purified by column chromatography (SiO₂, 0-20% MeOH in EtOAc) and then further purified by preparative HPLC to give the title compound (15 mg, 7%) as an off-white solid. $\delta_H$ (DMSO-d₆) 9.54 (br s, 1H), 9.34 (s, 1H), 8.92 (dd, J 4.2, 1.4 Hz, 1H), 8.77 (d, J 1.7 Hz, 1H), 8.68 (dd, J 4.8, 1.6 Hz, 1H), 8.49 (s, 1H), 8.21 (dd, J 8.5, 1.5 Hz, 1H), 8.13 (dd, J 8.3, 1.0 Hz, 1H), 8.09-8.03 (m, 2H), 7.92 (dd, J 8.5, 4.2 Hz, 1H), 7.72 (t, J 7.9 Hz, 1H), 7.52 (ddd, J 7.7, 4.8, 0.4 Hz, 1H), 6.77 (q, J 7.7 Hz, 1H). LCMS (ES+) 467 (M+H)⁺, RT 2.28 minutes.

Example 30

N—{(S)-1-[8-Chloro-2-(1-oxypyridin-3-yl)quinolin-3-yl]-2,2,2-trifluoroethyl}pyrido[3,2-d]-pyrimidin-4-ylamine A mixture of Intermediate 68 (0.34 g, 0.98 mmol), Intermediate 30 (0.285 g, 1.17 mmol) and p-toluenesulfonic acid (0.019 g, 0.098 mmol) in chloroform (75 mL) was heated at reflux for 16 h. The reaction mixture was partitioned between DCM and water. The aqueous phase was extracted with further DCM and the combined organic fractions were washed with saturated aqueous NaHCO₃ solution and brine, then dried Na₂SO₄) and evaporated in vacuo. The residue was purified by column chromatography (SiO₂, 3-20% MeOH in EtOAc) to give the title compound (364 mg, 77%) as an off-white solid. $\delta_H$(DMSO-d₆) 9.57 (d, J 9.0 Hz, 1H), 9.27 (s, 1H), 8.90 (dd, J 4.2, 1.5 Hz, 1H), 8.54 (s, 1H), 8.50 (t, J 1.3 Hz, 1H), 8.28-8.07 (m, 4H), 7.91 (dd, J 8.5, 4.2 Hz, 1H), 7.78-7.70 (m, 1H), 7.51-7.46 (m, 1H), 7.40 (dd, J 7.6, 6.5 Hz, 1H), 6.86-6.74 (m, 1H). LCMS (ES+) 483 (M+H)⁺, RT 1.86 minutes.

Example 31

N—{(R)-1-[2-(Pyridin-3-yl)quinolin-3-yl]-2,2,2-trifluoroethyl}pyrido[3,2-d]pyrimidin-4-amine A mixture of Intermediate 72 (0.67 g, 2.21 mmol) and Intermediate 30 (0.65 g, 2.65 mmol) in DCM (12 mL) was heated under microwave irradiation at 140° C. for 1 h. The reaction mixture was partitioned between DCM and water. The aqueous phase was extracted with further DCM and the combined organic fractions were washed with brine, then dried Na₂SO₄) and evaporated in vacuo. The residue was purified by column chromatography (SiO₂, 0-20% MeOH in EtOAc) to give the title compound (291 mg, 30%) as a dark blue solid. $\delta_H$(DMSO-d₆) 9.52 (d, J 9.2 Hz, 1H), 9.28 (s, 1H), 8.92 (dd, J 4.2, 1.5 Hz, 1H), 8.74 (dd, J 2.2, 0.7 Hz, 1H), 8.67 (dd, J 4.8, 1.6 Hz, 1H), 8.48 (s, 1H), 8.21 (dd, J 8.5, 1.6 Hz, 1H), 8.13 (dd, J 8.2, 0.7 Hz, 1H), 8.08 (d, J 8.6 Hz, 1H), 8.05-8.00 (m, 1H), 7.94-7.86 (m, 2H), 7.77-7.71 (m, 1H), 7.51 (ddd, J 7.8, 4.9, 0.8 Hz, 1H), 6.74 (quint, J 8.3 Hz, 1H). LCMS (ES+) 433 (M+H)⁺, RT 1.99 minutes.

Example 32

N—{(R)-1-[2-(1-Oxypyridin-3-yl)quinolin-3-yl]-2,2,2-trifluoroethyl}pyrido[3,2-d]-pyrimidin-4-amine A stirred solution of Example 31 (273 mg, 0.632 mmol) in DCM (10 mL) was cooled to 0° C. MCPBA (98 mg, 0.569 mmol) was added and the mixture was allowed to warm slowly to r.t. over 3 h. The reaction mixture was partitioned between DCM and saturated aqueous NaHCO₃ solution. The aqueous phase was extracted with further DCM and the combined organic fractions were washed with brine, dried Na₂SO₄) and evaporated in vacuo. The residue was purified by column chromatography (SiO₂, 0-25% MeOH in EtOAc) to give the title compound (66 mg, 23%) as an off-white solid. $\delta_H$ (DMSO-d₆) 9.54 (d, J 9.1 Hz, 1H), 9.21 (s, 1H), 8.91 (dd, J 4.2, 1.6 Hz, 1H), 8.54 (s, 1H), 8.47 (t, J 1.3 Hz, 1H), 8.26-8.07 (m, 4H), 7.94-7.87 (m, 2H), 7.79-7.72 (m, 1H), 7.50-7.38 (m, 2H), 6.76 (quint, J 8.1 Hz, 1H). LCMS (ES+) 449 (M+H)⁺, RT 1.71 minutes.

Example 33

N—{(R)-1-[8-Chloro-2-(6-chloropyridin-3-yl)quinolin-3-yl]-2,2,2-trifluoroethyl}pyrido[3,2-d]pyrimidin-4-ylamine A mixture of Intermediate 76 (0.37 g, 0.995 mmol) and Intermediate 30 (0.27 g, 1.09 mmol) in DCM (5 mL) was heated under microwave irradiation at 140° C. for 30 minutes. The reaction mixture was partitioned between DCM and water. The aqueous phase was extracted with further DCM and the combined organic fractions were washed with brine, then dried Na₂SO₄) and evaporated in vacuo. The residue was purified by column chromatography (SiO₂, 40-100% EtOAc in hexane) to give the title compound (371 mg, 74%) as a yellow gum. $\delta_H$ (DMSO-d₆) 9.55 (d, J 9.0 Hz, 1H), 9.29 (s, 1H), 8.91 (dd, J 4.2, 1.5 Hz, 1H), 8.62 (dd, J 2.4, 0.4 Hz, 1H), 8.51 (s, 1H), 8.22 (dd, J 8.5, 1.5 Hz, 1H), 8.16-8.06 (m, 3H), 7.92 (dd, J 8.5, 4.2 Hz, 1H), 7.76-7.69 (m, 1H), 7.61 (dd, J 8.2, 0.5 Hz, 1H), 6.73 (quint, J 8.1 Hz, 1H). LCMS (ES+) 501 (M+H)+, RT 2.67 minutes.

Example 34

N—{(R)-1-[2-(2-Methyl-1-oxypyridin-3-yl)-8-(trifluoromethyl)quinolin-3-yl]-2,2,2-trifluoroethyl}pyrido[3,2-d]pyrimidin-4-amine A mixture of Intermediate 84 (395 mg, 1.0 mmol), Intermediate 30 (270 mg, 1.1 mmol) and p-toluenesulphonic acid (25 mg) in chloroform (5 mL) was heated at 70° C. overnight. The reaction mixture was cooled to room temperature, diluted with DCM (20 mL), washed with water (2×10 mL) and brine (10 mL), then dried Na$_2$SO$_4$), filtered and concentrated in vacuo. The resulting off-white foam was purified by column chromatography (SiO$_2$, EtOAc to 8% MeOH). The colourless glass thereby obtained was freeze-dried from MeCN/H$_2$O to give the title compound (255 mg, 48%) as a white solid. $\delta_H$ (DMSO-d$_6$; as an approximately 0.55:0.45 mixture of rotamers) 9.61 (d, J 9.2 Hz, 0.45H), 9.52 (d, J 9.2 Hz, 0.55H), 9.41 (s, 0.45H), 9.21 (s, 0.55H), 8.93 (dd, J 4.2, 1.5 Hz, 0.45H), 8.84 (dd, J 4.1, 1.4 Hz, 0.55H), 8.56 (m, 1H), 8.49 (d, J 7.9 Hz, 0.5H), 8.38 (d, J 6.3 Hz, 0.4H), 8.33 (m, 1.5H), 8.22 (m, 1.5H), 7.90 (m, 2H), 7.46 (m, 1.1H), 7.23 (m, 0.9H), 6.65 (m, 1H), 2.19 (s, 1.4H), 1.61 (s, 1.6H). LCMS (ES+) 531.2 (M+H)+.

Example 35

N—{(R)-1-[8-(Methanesulfonyl)-2-(2-methylpyridin-3-yl)quinolin-3-yl]-2,2,2-trifluoro-ethyl}pyrido[3,2-d]pyrimidin-4-amine Intermediate 92 (340 mg, 0.86 mmol) and Intermediate 30 (294 mg, 1.29 mmol) were suspended in DCM and heated under microwave irradiation at 140° C. for 1 h. The reaction mixture was cooled and partitioned between DCM and sodium hydrogensulphate solution, then dried over sodium sulphate and concentrated. The crude material was purified by column chromatography (SiO$_2$, EtOAc/5% MeOH) to give the title compound (62%) as a pale solid. $\delta_H$ (DMSO-d$_6$; 1:1 mixture of rotamers) 9.55 (m, 0.5H), 9.47 (s, 1H), 9.29 (s, 0.5H), 8.94-8.84 (m, 1H), 8.60 (m, 1H), 8.49-8.41 (m, 2.5H), 8.29-8.14 (m, 1.5H), 7.97-7.85 (m, 2.5H), 7.72 (m, 0.5H), 7.41 (m, 0.5H), 7.17 (m, 0.5H), 6.58 (m, 1H), 3.47 (s, 1.5H), 3.44 (s, 1.5H), 2.29 (s, 1.5H), 1.82 (s, 1.5H). LCMS (ES+) 525.0 (M+H)+, RT 1.88 minutes.

Example 36

N—{(R)-1-[8-(Methanesulfonyl)-2-(2-methyl-1-oxypyridin-3-yl)quinolin-3-yl]-2,2,2-trifluoroethyl}pyrido[3,2-d]pyrimidin-4-amine A stirred solution of Example 35 (500 mg, 0.95 mmol) in DCM (20 mL) was cooled to 0° C. MCPBA (150 mg, 0.76 mmol) was added and the mixture was allowed to warm slowly to r.t. over 4 h. The reaction mixture was diluted with DCM (15 mL) and washed with saturated aqueous NaHCO$_3$ solution (25 mL) and brine (25 mL), dried (phase separator) and evaporated in vacuo. The residue was purified by preparative HPLC to give the title compound (36%) as a pale solid. $\delta_H$ (DMSO-d$_6$; 1:1 mixture of rotamers) 9.60 (d, J 9.1 Hz, 0.5H), 9.56 (d, J 9.5 Hz, 0.5H), 9.44 (s, 0.5H), 9.27 (s, 0.5H), 8.92-8.84 (m, 1H), 8.64-8.56 (m, 1H), 8.54 (s, 0.5H), 8.54-8.50 (m, 1H), 8.38 (m, 0.5H), 8.31 (s, 0.5H), 8.25 (m, 0.5H), 8.24-8.17 (m, 1H), 7.99-7.95 (m, 1H), 7.95-7.86 (m, 1H), 7.53-7.46 (m, 1H), 7.28 (m, 0.5H), 7.17 (m, 0.5H), 6.72-6.59 (br m, 1H), 3.46 (s, 1.5H), 3.44 (s, 1.5H), 2.21 (s, 1.5H), 1.63 (s, 1.5H). LCMS (ES+) 541.0 (M+H)+, RT 1.62 and 1.66 minutes.

Example 37

N—{(R)-1-[8-(Methanesulfonyl)-2-(pyridin-3-yl)quinolin-3-yl]-2,2,2-trifluoroethyl}-pyrido[3,2-d]pyrimidin-4-amine Intermediate 99 (870 mg, 2.28 mmol) and Intermediate 30 (669 mg. 2.74 mmol) in DCM were heated under microwave irradiation at 140° C. for 1 h. The reaction mixture was cooled and partitioned between DCM and sodium hydrogencarbonate solution, then dried over sodium sulphate and concentrated. Chromatography (30-70% ethanol-water) on C-18 reverse phase silica yielded the title compound (350 mg). $\delta_H$ (DMSO-d$_6$) 9.60 (d, J 9.1 Hz, 1H), 9.46 (s, 1H), 8.93 (dd, J 4.2, 1.4 Hz, 1H), 8.85 (d, J 1.9 Hz, 1H), 8.70 (dd, J 4.8, 1.6 Hz, 1H), 8.51 (m, 3H), 8.22 (dd, J 8.5, 1.5 Hz, 1H), 8.15 (dt, J 7.8, 1.9 Hz, 1H), 7.94 (m, 2H), 7.56 (m, 1H), 6.85 (m, 1H), 3.54 (s, 3H). LCMS (ES+) 511 (M+H)+, RT 1.87 minutes.

The invention claimed is:

1. A compound of formula (I) or an N-oxide thereof, or a pharmaceutically acceptable salt thereof:

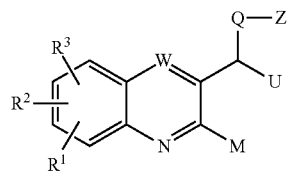

(I)

wherein
U represents —CF$_3$, —CHF$_2$ or —CH$_2$F;
Q represents oxygen, sulfur, N—R$^4$ or a covalent bond;
Z represents an optionally substituted bicyclic heteroaryl moiety consisting of two fused six-membered aromatic rings, the heteroaryl moiety Z containing at least one nitrogen atom and being linked to the remainder of the molecule through a carbon atom, wherein the substituents are independently halogen, cyano, nitro, C$_{1-6}$ alkyl, trifluoromethyl, hydroxy, oxo, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkyl-amino, arylamino, C$_{1-6}$ alkoxyaryl(C$_{1-6}$) alkylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl, C$_{2-6}$ alkoxycarbonylamino or (C$_{1-6}$)alkyl(C$_{3-6}$)heterocycloalkylcarbonyl;
M represents aryl or heteroaryl, either of which groups may be optionally substituted by one or more substituents, wherein the substituents are independently halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkyl-amino, C$_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, aminosulfonyl, $C_{1-6}$ alkylaminosulfonyl, di($C_{1-6}$)alkylaminosulfonyl, $C_{3-7}$ cycloalkyl, $C_{3-6}$ heterocycloalkyl, monocyclic aryl, monocyclic heteroaryl, $C_{2-6}$ alkoxycarbonylamino, or ($C_{1-6}$)alkyl($C_{3-6}$)heterocycloalkyl;

W represents C—$R^5$;

$R^1$, $R^2$ and $R^3$ independently represent hydrogen, halogen, cyano, nitro, $C_{1-6}$ alkyl, trifluoromethyl, $C_{3-7}$ cycloalkyl ($C_{1-6}$)alkyl, $C_{3-7}$ heterocycloalkyl($C_{1-6}$)alkyl, aryl($C_{1-6}$)-alkyl, heteroaryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^4$ represents hydrogen or $C_{1-6}$ alkyl; and $R^5$ represents hydrogen, halogen, $C_{1-6}$ alkyl or $C_{1-6}$ alkoxy.

2. The compound as claimed in claim 1 represented by formula (IIA), or a pharmaceutically acceptable salt thereof:

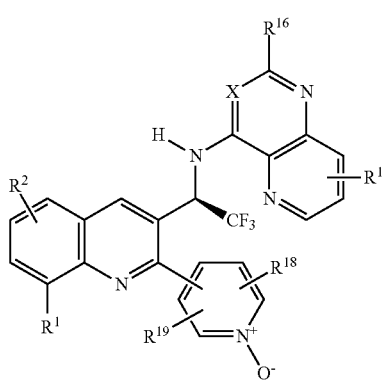

(IIA)

wherein X represents N or CH;

$R^{16}$ and $R^{17}$ independently represent hydrogen, halogen, cyano, $C_{1-6}$ alkyl, trifluoromethyl, amino, $C_{1-6}$ alkylamino or di($C_{1-6}$)alkylamino; and $R^{18}$ and $R^{19}$ independently represent hydrogen, halogen, cyano, $C_{1-6}$ alkyl, trifluoromethyl or aminocarbonyl.

3. The compound as claimed in claim 2 wherein X represents N.

4. The compound as claimed in claim 2 wherein $R^{16}$ represents hydrogen.

5. The compound as claimed in claim 2 wherein $R^{17}$ represents hydrogen.

6. The compound as claimed in claim 2 wherein $R^{18}$ represents hydrogen or $C_{1-6}$ alkyl.

7. The compound as claimed in claim 6 wherein $R^{18}$ represents hydrogen.

8. The compound as claimed in claim 7 wherein $R^{18}$ represents methyl.

9. The compound as claimed in claim 2 wherein $R^{19}$ represents hydrogen.

10. The compound as claimed in claim 9 represented by formula (IIB), or a pharmaceutically acceptable salt thereof:

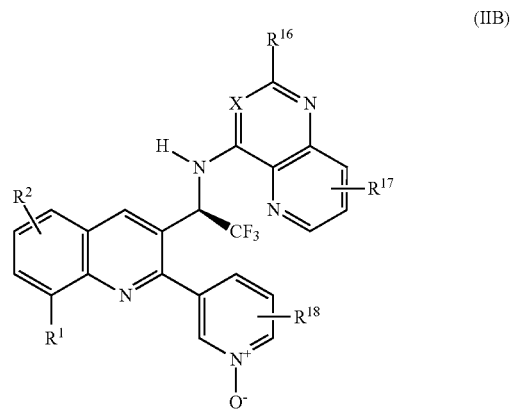

(IIB)

11. The compound as claimed in claim 10 wherein X represents N.

12. The compound as claimed in claim 10 wherein $R^{16}$ represents hydrogen.

13. The compound as claimed claim 10 wherein $R^{17}$ represents hydrogen.

14. The compound as claimed in claim 10 wherein $R^{18}$ represents hydrogen or $C_{1-6}$ alkyl.

15. The compound as claimed in claim 14 wherein $R^{18}$ represents hydrogen.

16. The compound as claimed in claim 14 wherein $R^{18}$ represents methyl.

17. The compound as claimed in claim 1 wherein M represents phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl or triazinyl, any of which groups may be optionally substituted by one or more substituents selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, $C_{3-7}$ cycloalkyl, $C_{3-6}$ heterocycloalkyl, ($C_{1-6}$)alkyl($C_{3-6}$)heterocycloalkyl, monocyclic aryl and monocyclic heteroaryl.

18. The compound as claimed in claim 17 wherein M represents phenyl, pyridinyl or pyrazinyl, any of which groups may be optionally substituted by one or more substituents independently selected from halogen, $C_{1-6}$ alkyl and $C_{1-6}$ alkoxy.

19. The compound as claimed in claim 18 wherein M represents pyridinyl.

20. The compound as claimed in claim 18 wherein M represents methylpyridinyl.

21. The compound as claimed in claim 1 wherein U represents —$CF_3$.

22. The compound as claimed in claim 21 wherein the carbon atom to which the -Q-Z and —$CF_3$ moieties are directly attached is in the (R) configuration.

23. The compound as claimed in claim 1 wherein Q represents N—$R^4$.

24. The compound as claimed in claim 23 wherein $R^4$ represents hydrogen or methyl.

25. The compound as claimed in claim 1 wherein Z represents quinolinyl, isoquinolinyl, cinnolinyl, quinazolinyl, quinoxalinyl, phthalazinyl, naphthyridinyl, pyrido-pyrimidinyl or pteridinyl, all of which groups are linked to the remainder of the molecule through a carbon atom, and any of which groups is optionally substituted by one or more substituents independently selected from halogen, cyano, nitro, $C_{1-6}$ alkyl, trifluoromethyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{1-6}$ alkoxyaryl($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, ($C_{1-6}$)alkyl-($C_{3-6}$)heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$) alkylaminosulfonyl.

26. The compound as claimed in claim 25 wherein Z represents pyrido[3,2-d]pyrimidin-4-yl.

27. The compound as claimed in claim 1 wherein $R^1$ represents hydrogen, halogen, $C_{1-6}$ alkyl, trifluoromethyl or $C_{1-6}$ alkylsulfonyl.

28. The compound as claimed in claim 27 wherein $R^1$ represents chloro.

29. The compound as claimed in claim 27 wherein $R^1$ represents trifluoromethyl.

30. The compound as claimed in claim 1 wherein $R^2$ represents hydrogen, halogen or $C_{1-6}$ alkyl.

31. The compound as claimed in claim 30 wherein $R^2$ represents hydrogen.

32. The compound as claimed in claim 1 which is an N-oxide or a pharmaceutically acceptable salt thereof.

33. The compound as claimed in claim 1 wherein $R^5$ represents hydrogen.

34. The compound as claimed in claim 1 wherein $R^3$ represents hydrogen.

35. The compound according to claim 1 which is
N—{(R)-1-[8-Chloro-2-(pyridin-3-yl)quinolin-3-yl]-2,2,2-trifluoroethyl}pyrido[3,2-d]pyrimidin-4-ylamine,
N—{(R)-1-[8-Chloro-2-(1-oxypyridin-3-yl)quinolin-3-yl]-2,2,2-trifluoroethyl}pyrido[3,2-d]pyrimidin-4-ylamine,
N—[(R)-1-(8-Chloro-2-phenylquinolin-3-yl)-2,2,2-trifluoroethyl]pyrido[3,2-d]pyrimidin-4-ylamine,
N—{(R)-1-[8-Chloro-2-(4-methylpyridin-3-yl)quinolin-3-yl]-2,2,2-trifluoroethyl}pyrido[3,2-d]pyrimidin-4-ylamine,
N—{(R)-1-[8-Chloro-2-(4-methyl-1-oxypyridin-3-yl)quinolin-3-yl]-2,2,2-trifluoroethyl}-pyrido[3,2-d]pyrimidin-4-ylamine,
N—{(R)-1-[8-Chloro-2-(2-methylpyridin-3-yl)quinolin-3-yl]-2,2,2-trifluoroethyl}pyrido[3,2-d]pyrimidin-4-ylamine,
N—{(R)-1-[8-Chloro-2-(2-methyl-1-oxypyridin-3-yl)quinolin-3-yl]-2,2,2-trifluoroethyl}-pyrido[3,2-d]pyrimidin-4-ylamine,
N—{(R)-1-[8-Chloro-2-(5-methylpyridin-3-yl)quinolin-3-yl]-2,2,2-trifluoroethyl}-pyrido[3,2-]pyrimidin-4-ylamine,
N—{(R)-1-[8-Chloro-2-(5-methyl-1-oxypyridin-3-yl)quinolin-3-yl]-2,2,2-trifluoroethyl}-pyrido[3,2-d]pyrimidin-4-yl-amine,
N—{(R)-1-[8-Chloro-2-(pyrazin-2-yl)quinolin-3-yl]-2,2,2-trifluoroethyl}pyrido[3,2-d]pyrimidin-4-ylamine,
N—{(R)-1-[8-Chloro-2-(6-methoxypyrazin-2-yl)quinolin-3-yl]-2,2,2-trifluoroethyl}-pyrido[3,2-d]pyrimidin-4-ylamine,
N—{(R)-1-[8-Chloro-2-(6-methylpyridin-3-yl)quinolin-3-yl]-2,2,2-trifluoroethyl}-pyrido[3,2-d]pyrimidin-4-amine,
N—{(R)-1-[8-Chloro-2-(6-methyl-1-oxypyridin-3-yl)quinolin-3-yl]-2,2,2-trifluoroethyl}-pyrido[3,2-d]pyrimidin-4-amine,
N—{(R)-1-[8-Methyl-2-(pyridin-3-yl)quinolin-3-yl]-2,2,2-trifluoroethyl}pyrido[3,2-d]-pyrimidin-4-amine,
N—{(R)-1-[8-Methyl-2-(1-oxypyridin-3-yl)quinolin-3-yl]-2,2,2-trifluoroethyl}pyrido[3,2-d]pyrimidin-4-amine,
N—{(R)-1-[7-Fluoro-8-methyl-2-(pyridin-3-yl)quinolin-3-yl]-2,2,2-trifluoroethyl}-pyrido[3,2-d]pyrimidin-4-amine,
N—{(R)-1-[7-Fluoro-8-methyl-2-(1-oxypyridin-3-yl)quinolin-3-yl]-2,2,2-trifluoroethyl}-pyrido[3,2-d]pyrimidin-4-amine,
N—{(R)-1-[7-Fluoro-8-methyl-2-(2-methylpyridin-3-yl)quinolin-3-yl]-2,2,2-trifluoro-ethyl}pyrido[3,2-d]pyrimidin-4-amine,
N—{(R)-1-[7-Fluoro-8-methyl-2-(2-methyl-1-oxypyridin-3-yl)quinolin-3-yl]-2,2,2-trifluoroethyl}pyrido[3,2-d]pyrimidin-4-amine,
N—{(R)-1-[7-Fluoro-8-methyl-2-(5-methylpyridin-3-yl)quinolin-3-yl]-2,2,2-trifluoro-ethyl}pyrido[3,2-d]pyrimidin-4-amine,
N—{(R)-1-[7-Fluoro-8-methyl-2-(5-methyl-1-oxypyridin-3-yl)quinolin-3-yl]-2,2,2-trifluoroethyl}pyrido[3,2-d]pyrimidin-4-amine,
N—{(R)-1-[2-(Pyridin-3-yl)-8-(trifluoromethyl)quinolin-3-yl]-2,2,2-trifluoroethyl}-pyrido[3,2-d]pyrimidin-4-amine,
N—{(R)-1-[2-(1-Oxypyridin-3-yl)-8-(trifluoromethyl)quinolin-3-yl]-2,2,2-trifluoroethyl}-pyrido[3,2-d]pyrimidin-4-amine,
N—{(R)-1-[2-(6-Methylpyridin-3-yl)-5,6,8-trifluoroquinolin-3-yl]-2,2,2-trifluoroethyl}-pyrido[3,2-d]pyrimidin-4-amine,
N—{(R)-1-[2-(6-Methyl-1-oxypyridin-3-yl)-5,6,8-trifluoroquinolin-3-yl]-2,2,2-trifluoro-ethyl}pyrido[3,2-d]pyrimidin-4-amine,
N—{(R)-1-[8-Chloro-2-(pyridin-3-yl)quinolin-3-yl]-2,2,2-trifluoroethyl}N-methylpyrido[3,2-d]pyrimidin-4-ylamine,
N—{(R)-1-[8-Chloro-2-(pyridin-3-yl)quinolin-3-yl]-2,2,2-trifluoroethyl}N-(1-oxypyrido-[3,2-d]pyrimidin-4-yl)amine,
N—{(R)-1-[8-Chloro-2-(1-oxypyridin-3-yl)quinolin-3-yl]-2,2,2-trifluoroethyl}N-(1-oxy-pyrido[3,2-d]pyrimidin-4-yl)amine,
N—{(S)-1-[8-Chloro-2-(pyridin-3-yl)quinolin-3-yl]-2,2,2-trifluoroethyl}pyrido[3,2-d]pyrimidin-4-ylamine,
N—{(S)-1-[8-Chloro-2-(1-oxypyridin-3-yl)quinolin-3-yl]-2,2,2-trifluoroethyl}pyrido[3,2d]pyrido[3,2-d]pyrimidin-4-ylamine,
N—{(R)-1-[2-(Pyridin-3-yl)quinolin-3-yl]-2,2,2-trifluoroethyl}pyrido[3,2-d]pyrimidin-4-amine,
N—{(R)-1-[2-(1-Oxypyridin-3-yl)quinolin-3-yl]-2,2,2-trifluoroethyl}pyrido[3,2-d]-pyrimidin-4-amine,
N—{(R)-1[8-Chloro-2-(6-chloropyridin-3-yl)quinolin-3-yl]-2,2,2-trifluoroethyl}pyrido[3,2-d]pyrimidin-4-ylamine, N—{(R)-1-[2-(2-Methyl-1-oxypyridin-3-yl)-8-(trifluoromethyl)quinolin-3-yl]-2,2,2-trifluoroethyl}pyrido[3,2-d]pyrimidin-4-amine, N—{(R)-1[8-(Methanesulfonyl)-2-(2-methylpyridin-3-yl)quinolin-3-yl]-2,2,2-trifluoro-ethyl}pyrido[3,2-d]pyrimidin-4-amine, N—{(R)-1[8-(Methanesulfonyl)-2-(2-methyl-1-oxypyridin-3-yl)quinolin-3-yl]-2,2,2-trifluoroethyl}pyrido[3,2-d]pyrimidin-4-amine, N—{(R)-1[8-(Methanesulfonyl)-2-(pyridin-3-yl)quinolin-3-yl]-2,2,2-trifluoroethyl}-pyrido[3,2-d]pyrimidin-4-amine, or a pharmaceutically acceptable salt thereof.

36. A pharmaceutical composition comprising a compound of formula (I) as defined in claim 1 or an N-oxide thereof, or a pharmaceutically acceptable salt thereof, in association with a pharmaceutically acceptable carrier.

37. A method for inhibiting phosphoinositide 3-kinase activity in a patient which comprises administering to a patient in need of such treatment an effective amount of a compound of formula (I) as defined in claim 1 or an N-oxide thereof, or a pharmaceutically acceptable salt thereof.

38. N—{(R)-1-[8-Chloro-2-(1-oxypyridin-3-yl)quinolin-3-yl]-2,2,2-trifluoroethyl}-pyrido[3,2-d]pyrimidin-4-ylamine.

39. A pharmaceutical composition comprising N—{(R)-1-[8-chloro-2-(1-oxypyridin-3-yl)quinolin-3-yl]-2,2,2-trifluoroethyl}pyrido[3,2-]pyrimidin-4-ylamine in association with a pharmaceutically acceptable carrier.

40. A method for inhibiting phosphoinositide 3-kinase activity in a patient which comprises administering to a patient in need of such treatment an effective amount of N—{(R)-1-[8-chloro-2-(1-oxypyridin-3-yl)quinolin-3-yl]-2,2,2-trifluoroethyl}pyrido[3,2-d]pyrimidin-4-ylamine.

\* \* \* \* \*